US012630626B2

(12) United States Patent
Du et al.

(10) Patent No.: US 12,630,626 B2
(45) Date of Patent: May 19, 2026

(54) ANTI-CLDN18.2 ANTIBODY AND USES THEREOF

(71) Applicant: SHANGHAI GENBASE BIOTECHNOLOGY CO., LTD., Shanghai (CN)

(72) Inventors: Liang Du, Shanghai (CN); Hongyan Zhang, Shanghai (CN); Wen Ling, Shanghai (CN); Jijun Yuan, Shanghai (CN)

(73) Assignee: SHANGHAI GENBASE BIOTECHNOLOGY CO., LTD., Shanghai (CN)

( * ) Notice: Subject to any disclaimer, the term of this patent is extended or adjusted under 35 U.S.C. 154(b) by 1292 days.

(21) Appl. No.: 17/287,946

(22) PCT Filed: Oct. 22, 2018

(86) PCT No.: PCT/CN2018/111201
§ 371 (c)(1),
(2) Date: Apr. 22, 2021

(87) PCT Pub. No.: WO2020/082209

PCT Pub. Date: Apr. 30, 2020

(65) Prior Publication Data

US 2021/0403552 A1 Dec. 30, 2021

(51) Int. Cl.

| | |
|---|---|
| *G01N 31/00* | (2006.01) |
| *A61K 39/395* | (2006.01) |
| *A61K 40/10* | (2025.01) |
| *A61K 40/11* | (2025.01) |
| *A61K 40/31* | (2025.01) |
| *A61K 40/42* | (2025.01) |
| *A61K 45/06* | (2006.01) |
| *A61K 47/68* | (2017.01) |
| *A61P 35/00* | (2006.01) |
| *C07K 16/28* | (2006.01) |
| *G01N 33/53* | (2006.01) |
| *A61K 39/00* | (2006.01) |

(52) U.S. Cl.
CPC .......... *C07K 16/28* (2013.01); *A61K 39/3955* (2013.01); *A61K 40/10* (2025.01); *A61K 40/11* (2025.01); *A61K 40/31* (2025.01); *A61K 40/4202* (2025.01); *A61K 45/06* (2013.01); *A61K 47/6849* (2017.08); *A61P 35/00* (2018.01); *A61K 2039/505* (2013.01); *C07K 2317/24* (2013.01); *C07K 2317/31* (2013.01); *C07K 2317/565* (2013.01); *C07K 2317/622* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

2021/0230272 A1 7/2021 Liu

FOREIGN PATENT DOCUMENTS

| | | |
|---|---|---|
| CN | 107667118 | 2/2018 |
| CN | 107960056 | 4/2018 |
| CN | 108047331 | 5/2018 |
| WO | WO2007/059997 | 5/2007 |
| WO | WO2013/167259 | 11/2013 |
| WO | WO2016/165762 | 10/2016 |
| WO | WO2016/166122 | 10/2016 |
| WO | WO2016/180468 | 11/2016 |
| WO | WO2016/180782 | 11/2016 |
| WO | 2016/198835 A1 | 12/2016 |
| WO | 2019/174617 A1 | 9/2019 |
| WO | 2019/242505 A1 | 12/2019 |
| WO | WO2020025792 | 2/2020 |
| WO | WO2021027850 | 2/2021 |

OTHER PUBLICATIONS

Hjelm et al (PLoS One, 2012, vol. 7, issue 12; e45817, internet pp. 1-12) (Year: 2012).*
He et al (PNAS, 2016, 113:11931-11986) (Year: 2016).*
Weitzman et al (Leukemia & Lymphoma, 2009, 50:1361-1368) (Year: 2009).*
Liu et al., "Fine mapping of the antigen-antibody interaction of scFv215, a recombinant antibody inhibiting RNA polymerase II from Drosophila melanogaster," J. Mol. Recognit., 12(2):103-11 (1999).
Rudikoff et al., "Single amino acid substitution altering antigen-binding specificity," Proceedings of the National Academy of Sciences, 79(6):1979-1983 (1982).
Wong et al., "Structural requirements for a specificity switch and for maintenance of affinity using mutational analysis of a phage-displayed anti-arsonate antibody of Fab heavy chain first complementarity-determining region," J. Immunol., 160(12):5990-5997 (1998).

* cited by examiner

*Primary Examiner* — Lisa V Cook
(74) *Attorney, Agent, or Firm* — Leason Ellis LLP; James F. Haley, Jr.; Kendra V. Johnson

(57) ABSTRACT

Provided are an anti-CLDN18.2 antibody or antigen-binding fragment thereof, a nucleic acid molecule encoding the same, an immunoconjugate, bispecific molecule, chimeric antigen receptor and pharmaceutical composition comprising the same. The antibody or antigen-binding fragment thereof is used for preventing and/or treating a tumor.

30 Claims, 7 Drawing Sheets

Specification includes a Sequence Listing.

ANTI-CLDN18.2 ANTIBODY AND USES THEREOF

CROSS-REFERENCE TO RELATED APPLICATIONS

This application is a United States National Phase Application filed under 35 U.S.C. § 371 from International Patent Application No. PCT/CN/2018/111201, filed on Oct. 22, 2018. The contents and disclosure of the International Patent Application is incorporated by reference herein in its entirety.

SEQUENCE LISTING

The instant application contains a Sequence Listing which has been submitted electronically as a text file in ASCII format and is hereby incorporated by reference in its entirety. Said ASCII copy, created on Apr. 16, 2025, is named 000362-0001-301-SL.txt and is 76,678 bytes in size.

TECHNICAL FIELD

The present invention relates to the field of disease treatment and immunology. In particular, the present invention relates to an anti-CLDN18.2 antibody or an antigen-binding fragment thereof, a nucleic acid molecule encoding the same, an immunoconjugate, a bispecific molecule, a chimera antigen receptor and a pharmaceutical composition containing the same, and their use for the prevention and/or treatment of a tumor.

BACKGROUND ART

Gastric cancer is one of the most common malignant tumors in the world, its 5-year survival rate is low and is at a level of 20% to 40% in most countries, and about 700,000 people die from the disease every year. The survival rate of gastric cancer in China is 35.9%. According to statistics, the number of new cases of gastric cancer reached 679.1/100,000 and the number of deaths was as high as 498.0/100,000 in China in 2015, and thus gastric cancer had become the second most common tumor with high morbidity and mortality after lung cancer. Gastric cancer has a high degree of malignancy, and because gastric cancer screening has not been widely carried out, patients are usually diagnosed at an advanced stage, so that the opportunity for radical surgery is missed and only chemotherapy remains as the main treatment method.

With the development of tumor molecular biology, the targeted drugs and immunotherapy are confirmed to have efficacy in treatment of hematoma, breast cancer and colorectal cancer, but their application in gastric cancer treatment is relatively halted. At present, the internationally approved targets for gastric cancer targeted therapy include human epidermal growth factor receptor 2 (HER2) and vascular endothelial growth factor (VEGF), and the approved gastric cancer immunotherapy target is programmed lethal protein 1 (PD-1). In September 2017, based on the large-scale phase III clinical trial of ATTRACTION-2, the Ministry of Health, Labour and Welfare of Japan approved the PD-1 antibody Opdivo for the treatment of patients with chemotherapy-resistant advanced gastric cancer: as compared with placebo, Opdivo could reduce the mortality rate by 37% and showed an effective rate of 11.2%. Based on the phase II clinical trial of Keynote 059, the US FDA has accelerated the approval of using PD-1 antibody Keytruda in treatment of chemotherapy-resistant PD-L1-positive advanced gastric cancer patients, showing an effective rate of 15.5%. In terms of targeted therapy, vascular endothelial growth factor (VEGF) not only promotes tumor angiogenesis, but also binds to receptors on the surface of tumor cells to activate downstream signaling pathways and directly participates in the formation, occurrence and migration of tumor stem cells. Both the VEGFR2 inhibitors apatinib and ramucirumab have been clinically confirmed to be safe and effective for VEFR-targeted therapy of advanced gastric cancer of second-line and above. HER2 gene amplification or protein overexpression occurs in about 6% to 35% of new cases of gastric cancer each year, thus HER2 is one of the important targets in anticancer treatment. The TOGA phase III clinical trial first demonstrated the advantages of trastuzumab in the first-line treatment of HER2 (+) advanced gastric cancer, and the OS of the group treated with trastuzumab combined with chemotherapy was significantly longer than that of the group treated with chemotherapy alone (13.8 months vs. 11 Months), and the secondary endpoints including PFS, ORR (objective response rate) and TTP (time to progression) were also improved significantly. However, the proportion of HER2-positive patients in China is only about 10%, therefore it is imperative to explore new therapeutic targets for gastric cancer.

Claudin is a transmembrane protein complex within the tight junctions of epithelia and endothelia and located on the top side of the gap between adjacent cells. Its distribution is tissue and organ specific, and its functions mainly include cell adhesion, maintaining cell polarity, regulating paracellular permeability, and participating in regulation of cell proliferation and differentiation. Claudin18 molecule is a tetraspanin with four transmembrane hydrophobic regions and two extracellular loops, and exists as two different splice variants CLDN18.1 and CLDN18.2. CLDN18.1 and CLDN18.2 differ in sequence at the N-terminus of intracellular region and the first extracellular loop, but share the same protein primary sequence at the other parts. The tissue distribution of CLDN18 shows that CLDN18.1 is only selectively expressed on lung cells, while CLDN18.2 is only expressed on gastric cells, and the expression of CLDN18.2 in normal stomach is limited to differentiated short-lived gastric epithelium cells. CLDN18.2 is frequently retained during the malignant transformation of gastric cells, and is therefore frequently displayed on the surface of human gastric cancer cells, and 60% to 80% of gastrointestinal adenomas are CLDN18.2-positive (Clinical Cancer Research 2008, 14 (23): 7624-34). In addition, CLDN18.2 is highly expressed in pancreatic duct cancer and metastatic pancreatic cancer, with a positive rate of 60-70%, and thus can be used as a diagnostic marker and therapeutic target for pancreatic duct/pancreatic cancer (Journal of Clinical Pathology 2012, 65: 431-436; World Journal of Gastroenterology 2014, 20 (31): 10813-10824; International Journal of Cancer 2014, 134: 731-739). There is no intensive research on ectopic activation of CLDN18.2 in other tumors, and currently available documents show that in addition to the aforementioned ectopic activation in pancreatic cancer, this protein is also expressed in esophageal cancer, bronchial cancer, non-small cell lung cancer (NSCLC), breast cancer, ENT tumor, ovarian cancer, colon cancer, liver cancer and metastases thereof, especially in gastric cancer metastases such as Krukenberg tumor, peritoneal metastases and lymph node metastases (Clinical Cancer Research 2008, 14 (23): 7624-34; International Journal of Cancer 2014, 134: 731-739; Cancer Letters 2017, 403: 66-73; International Journal of Cancer 2014, 135 (9): 2206-2214). CLDN18.2 is a tumor target with preventive and therapeutic value, and its differential expression between cancer cells and normal cells, its membrane localization, its absence from most toxicity-relevant normal tissues, and the restriction of its expression in the stomach to differentiated gastric cells that can be replenished by target-negative stem cells (or positionally inaccessible stem cells) of the stomach, make CLDN18.2 be as an attractive target for cancer immunotherapy. Therefore, it is urgent and necessary to develop anti-CLDN18.2 antibodies with higher specificity, lower toxic or side effects, and better clinical efficacy, which will provide more medication options for cancer patients.

Contents of the Present Invention

The antibody of the present invention can specifically recognize/bind human CLDN18.2, and can induce the killing of a cell (e.g., tumor cell) expressing CLDN18.2 through ADCC and/or CDC, and shows better functional characteristics in comparison with known anti-CLDN18.2 antibody. Therefore, the antibody of the present invention has the potential for preventing and/or treating a tumor, and has great clinical value.

Antibodies of the Present Invention

Therefore, in one aspect, the present invention provides an antibody or antigen-binding fragment thereof which is capable of specifically binding to CLDN18.2, comprising:

(a) a heavy chain variable region (VH) comprising the following three complementary determining regions (CDRs):

(i) VH CDR1, consisting of the following sequence: SEQ ID NO: 75, or a sequence having a substitution, deletion or addition of one or several amino acids (e.g., a substitution, deletion or addition of 1, 2 or 3 amino acids) compared to SEQ ID NO: 75, (ii) VH CDR2, consisting of the following sequence: SEQ ID NO: 76, or a sequence having a substitution, deletion or addition of one or several amino acids (e.g., a substitution, deletion or addition of 1, 2 or 3 amino acids) compared to SEQ ID NO: 76, and (iii) VH CDR3, consisting of the following sequence: SEQ ID NO: 77, or a sequence having a substitution, deletion or addition of one or several amino acids (e.g., a substitution, deletion or addition of 1, 2 or 3 amino acids) compared to SEQ ID NO: 77;

and/or (b) a light chain variable region (VL) comprising the following three complementary determining regions (CDRs):

(iv) VL CDR1, consisting of the following sequence: SEQ ID NO: 78, or a sequence having a substitution, deletion or addition of one or several amino acids (e.g., a substitution, deletion or addition of 1, 2 or 3 amino acids) compared to SEQ ID NO: 78, (v) VL CDR2, consisting of the following sequence: SEQ ID NO: 79, or a sequence having a substitution, deletion or addition of one or several amino acids (e.g., a substitution, deletion or addition of 1, 2 or 3 amino acids) compared to SEQ ID NO: 79, and (vi) VL CDR3, consisting of the following sequence: SEQ ID NO: 80, or a sequence having a substitution, deletion or addition of one or several amino acids (e.g., a substitution, deletion or addition of 1, 2 or 3 amino acids) compared to SEQ ID NO: 80.

In certain preferred embodiments, the substitution as recited in any one of (i) to (vi) is a conservative substitution;

In certain preferred embodiments, the VH of the antibody or antigen-binding fragment thereof comprises: VH CDR1 as shown in SEQ ID NO: 75, VH CDR2 as shown in SEQ ID NO: 76, VH CDR3 as shown in SEQ ID NO: 77; and the VL of the antibody or antigen-binding fragment thereof comprises: VL CDR1 as shown in SEQ ID NO: 78 or 96, VL CDR2 as shown in SEQ ID NO: 79, and VL CDR3 as shown in SEQ ID NO: 80.

The present invention also provides an antibody or antigen-binding fragment thereof which is capable of specifically binding CLDN18.2, comprising a heavy chain variable region and a light chain variable region, wherein, (a) the heavy chain variable region comprises the 3 CDRs of the heavy chain variable region as shown in SEQ ID NO: 73; and the light chain variable region comprises the 3 CDRs of the light chain variable region as shown in SEQ ID NO: 74; or (b) the heavy chain variable region comprises the 3 CDRs of the heavy chain variable region as shown in SEQ ID NO: 91; and the light chain variable region comprises the 3 CDRs of the light chain variable region as shown in SEQ ID NO: 92.

In certain preferred embodiments, the 3 CDRs of the heavy chain variable region, and/or the 3 CDRs of the light chain variable region, are determined using the Kabat, Chothia, or IMGT numbering system.

In certain preferred embodiments, the antibody or antigen-binding fragment thereof is 44F7 or an antigen-binding fragment thereof, a chimeric antibody thereof, or a humanized antibody thereof, or a variant thereof, wherein the variant substantially retains biological function of the antibody or antigen-binding fragment from which it is derived.

In certain preferred embodiments, the antibody or antigen-binding fragment thereof has one or more of the following biological functions:

(a) binding to human CLDN18.2 with an EC50 of 0.1 µg/ml or less (e.g., 0.05 µg/ml or less);

(b) binding to mouse CLDN18.2 with an EC50 of 0.1 µg/ml or less;

(c) not binding to human CLDN18.1;

(d) inducing the killing of a cell expressing human CLDN18.2 (e.g., a tumor cell, such as a tumor cell expressing CLDN18.2) through antibody-dependent cell-mediated cytotoxicity (ADCC);

(e) inducing the killing of a cell expressing human CLDN18.2 (e.g., a tumor cell, such as a tumor cell expressing CLDN18.2) through complement dependent cytotoxicity (CDC);

(f) preventing and/or treating a tumor (e.g., a tumor expressing CLDN18.2) in a subject.

In certain preferred embodiments, the antibody or antigen-binding fragment thereof comprises:

(1) VH CDR1 as shown in SEQ ID NO: 75, VH CDR2 as shown in SEQ ID NO: 76, VH CDR3 as shown in SEQ ID NO: 77; VL CDR1 as shown in SEQ ID NO: 78 or 96, VL CDR2 as shown in SEQ ID NO: 79, VL CDR3 as shown in SEQ ID NO: 80; or (2) (a) the 3 CDRs of the heavy chain variable region as shown in SEQ ID NO: 73; and the 3 CDRs of the light chain variable region as shown in SEQ ID NO: 74; or (b) the 3 CDRs of the heavy chain variable region as shown in SEQ ID NO: 91; and the 3 CDRs of the light chain variable region as shown in SEQ ID NO: 92.

In an exemplary embodiment, the antibody or antigen-binding fragment thereof comprises:

(a) a heavy chain variable region (VH) comprising an amino acid sequence selected from the group consisting of:

(i) the sequence as shown in SEQ ID NO: 73;

(ii) a sequence having a substitution, deletion or addition of one or several amino acids (e.g., a substitution, deletion or addition of 1, 2, 3, 4 or 5 amino acids) compared to the sequence as shown in SEQ ID NO: 73; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 73;

and/or, (b) a light chain variable region (VL) comprising an amino acid sequence selected from the group consisting of:

(iv) the sequence as shown in SEQ ID NO: 74;

(v) a sequence having a substitution, deletion or addition of one or several amino acids (e.g., a substitution, deletion or addition of 1, 2, 3, 4 or 5 amino acids) compared to the sequence as shown in SEQ ID NO: 74; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 74.

In certain preferred embodiments, the substitution as recited in (ii) or (v) is a conservative substitution.

In certain preferred embodiments, the antibody or antigen-binding fragment thereof comprises: a VH having a sequence as shown in SEQ ID NO: 73 and a VL having a sequence as shown in SEQ ID NO: 74.

In certain preferred embodiments, the antibody or antigen-binding fragment thereof is humanized.

In certain preferred embodiments, the VH of the antibody or antigen-binding fragment thereof comprises a heavy chain variable region (VH) framework region (FR) derived from a human immunoglobulin, and/or the VL of the antibody or antigen-binding fragment thereof comprises a light chain variable region (VL) framework region (FR) derived from a human immunoglobulin. In such embodiments, the heavy chain variable region FR and/or light chain variable region FR of the antibody or antigen-binding fragment thereof may comprise one or more non-human (e.g., murine) amino acid residues, for example, the heavy chain framework region FR and/or light chain framework region FR may comprise one or more amino acid back mutations, and the corresponding murine amino acid residues are contained in these back mutations.

In certain preferred embodiments, the antibody or antigen-binding fragment thereof comprises:

(a) a heavy chain framework region of a human immunoglobulin or a variant thereof, in which the variant has a conservative substitution of up to 20 amino acids (e.g., a conservative substitution of up to 15, up to 10, or up to 5 amino acids; e.g., a conservative substitution of 1, 2, 3, 4 or 5 amino acids) compared to the sequence from which it is derived; and/or (b) a light chain framework region of a human immunoglobulin or a variant thereof, in which the variant has a conservative substitution of up to 20 amino acids (e.g., a conservative substitution of up to 15, up to 10, or up to 5 amino acids; e.g., a conservative substitution of 1, 2, 3, 4 or 5 amino acids) compared to the sequence from which it is derived.

In certain preferred embodiments, the antibody or antigen-binding fragment thereof comprises a framework region of a human immunoglobulin, such as a framework region contained in an amino acid sequence encoded by a human germline antibody gene. In certain preferred embodiments, the antibody or antigen-binding fragment thereof comprises: a heavy chain framework region contained in an amino acid sequence encoded by a human heavy chain germline gene, and/or a light chain framework region contained in an amino acid sequence encoded by a human light chain germline gene.

In such embodiments, the framework region (heavy chain framework region and/or light chain framework region) of the antibody or antigen-binding fragment thereof may comprise one or more non-human (e.g., murine) amino acid residues. In certain preferred embodiments, the framework region (heavy chain framework region and/or light chain framework region) comprises one or more amino acid residues which are mutated back to the corresponding murine residues or a conservative amino acid substitution of the corresponding murine residues (such mutation is called back mutation).

Therefore, in certain preferred embodiments, the antibody or antigen-binding fragment thereof comprises a framework region of a human immunoglobulin (e.g., a framework region contained in an amino acid sequence encoded by a human germline antibody gene), the framework region optionally comprises one or more back mutations from human residues to murine residues.

In an exemplary embodiment, the antibody or antigen-binding fragment thereof comprises:

(a) a heavy chain variable region (VH) comprising an amino acid sequence selected from the group consisting of:

(i) the sequence as shown in SEQ ID NO: 91;

(ii) a sequence having a substitution, deletion or addition of one or several amino acids (e.g., a substitution, deletion or addition of 1, 2, 3, 4 or 5 amino acids) compared to the sequence as shown in SEQ ID NO: 91; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 91;

and/or, (b) a light chain variable region (VL) comprising an amino acid sequence selected from the group consisting of:

(iv) the sequence shown in SEQ ID NO: 92;

(v) a sequence having a substitution, deletion or addition of one or several amino acids (e.g., a substitution, deletion or addition of 1, 2, 3, 4 or 5 amino acids) compared to the sequence as shown in SEQ ID NO: 92; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 92.

In certain preferred embodiments, the substitution as recited in (ii) or (v) is a conservative substitution.

In certain preferred embodiments, the antibody or antigen-binding fragment thereof comprises: a VH having a sequence as shown in SEQ ID NO: 91, and a VL having a sequence as shown in SEQ ID NO: 92.

In an exemplary embodiment, the antibody or antigen-binding fragment thereof comprises:

(a) a heavy chain variable region (VH) comprising an amino acid sequence selected from the group consisting of:

(i) the sequence shown in SEQ ID NO: 99;

(ii) a sequence having a substitution, deletion or addition of one or several amino acids (e.g., a substitution, deletion or addition of 1, 2, 3, 4 or 5 amino acids) compared to the sequence as shown in SEQ ID NO: 99; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 99;

and/or, (b) a light chain variable region (VL) comprising an amino acid sequence selected from the group consisting of:

(iv) the sequence shown in SEQ ID NO: 100;

(v) a sequence having a substitution, deletion or addition of one or several amino acids (e.g., a substitution, deletion or addition of 1, 2, 3, 4 or 5 amino acids) compared to the sequence as shown in SEQ ID NO: 100; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 100.

In certain preferred embodiments, the substitution as recited in (ii) or (v) is a conservative substitution.

In certain preferred embodiments, the antibody or antigen-binding fragment thereof comprises: a VH having a sequence as shown in SEQ ID NO: 99 and a VL having a sequence as shown in SEQ ID NO: 100.

In an exemplary embodiment, the antibody or antigen-binding fragment thereof comprises:

(a) a heavy chain variable region (VH) comprising an amino acid sequence selected from the group consisting of:

(i) the sequence shown in SEQ ID NO: 101;

(ii) a sequence having a substitution, deletion or addition of one or several amino acids (e.g., a substitution, deletion or addition of 1, 2, 3, 4 or 5 amino acids) compared to the sequence as shown in SEQ ID NO: 101; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 101;

and/or, (b) a light chain variable region (VL) comprising an amino acid sequence selected from the group consisting of:

(iv) the sequence shown in SEQ ID NO: 102;

(v) a sequence having a substitution, deletion or addition of one or several amino acids (e.g., a substitution, deletion or addition of 1, 2, 3, 4 or 5 amino acids) as compared to the sequence as shown in SEQ ID NO: 102; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 102.

In certain preferred embodiments, the substitution as recited in (ii) or (v) is a conservative substitution.

In certain preferred embodiments, the antibody or antigen-binding fragment thereof comprises: a VH having a sequence as shown in SEQ ID NO: 101 and a VL having a sequence as shown in SEQ ID NO: 102.

In another aspect, the present invention provides an antibody or antigen-binding fragment thereof which is capable of specifically binding CLDN18.2, comprising:

(a) a heavy chain variable region (VH) comprising the following 3 complementary determining regions (CDRs):

(i) VH CDR1, consisting of the following sequence: SEQ ID NO: 3, or a sequence having a substitution, deletion or addition of one or several amino acids (e.g., a substitution, deletion or addition of 1, 2 or 3 amino acids) compared thereto;

(ii) VH CDR2, consisting of the following sequence: SEQ ID NO: 4, or a sequence having a substitution, deletion or addition of one or several amino acids (e.g., a substitution, deletion or addition of 1, 2 or 3 amino acids) compared thereto; and (iii) VH CDR3, consisting of the following sequence: SEQ ID NO: 5, or a sequence having a substitution, deletion or addition of one or several amino acids (e.g., a substitution, deletion or addition of 1, 2 or 3 amino acids) compared thereto;

and/or (b) a light chain variable region (VL) comprising the following 3 complementary determining regions (CDRs):

(iv) VL CDR1, consisting of the following sequence: SEQ ID NO: 6, or a sequence having a substitution, deletion or addition of one or several amino acids (e.g., a substitution, deletion or addition of 1, 2 or 3 amino acids) compared thereto, (v) VL CDR2, consisting of the following sequence: SEQ ID NO: 7, or a sequence having a substitution, deletion or addition of one or several amino acids (e.g., a substitution, deletion or addition of 1, 2 or 3 amino acids) compared thereto, and (vi) VL CDR3, consisting of the following sequence: SEQ ID NO: 8, or a sequence having a substitution, deletion or addition of one or several amino acids (e.g., a substitution, deletion or addition of 1, 2 or 3 amino acids) compared thereto.

In certain preferred embodiments, the substitution as recited in any one of (i) to (vi) is a conservative substitution.

In certain preferred embodiments, the VH of the antibody or antigen-binding fragment thereof comprises: VH CDR1 as shown in SEQ ID NO: 3, VH CDR2 as shown in SEQ ID NO: 4, and VH CDR3 as shown in SEQ ID NO: 5; and the VL of the antibody or antigen-binding fragment thereof comprises: VL CDR1 as shown in SEQ ID NO: 6, VL CDR2 as shown in SEQ ID NO: 7, and VL CDR3 as shown in SEQ ID NO: 8.

The present invention also provides an antibody or antigen-binding fragment thereof which is capable of specifically binding to CLDN18.2, comprising a heavy chain variable region and a light chain variable region, wherein the heavy chain variable region comprises the 3 CDRs of the heavy chain variable region as shown in SEQ ID NO: 1; and the light chain variable region comprises the 3 CDRs of the light chain variable region as shown in SEQ ID NO: 2.

In certain preferred embodiments, the 3 CDRs of the heavy chain variable region, and/or the 3 CDRs of the light chain variable region, are determined using the Kabat, Chothia, or IMGT numbering system.

In certain preferred embodiments, the antibody or antigen-binding fragment thereof is 1D10 or an antigen-binding fragment thereof, a chimeric antibody thereof, or a humanized antibody thereof, or a variant thereof, in which the variant substantially retains a biological function of the antibody or antigen-binding fragment from which it is derived.

In certain preferred embodiments, the antibody or antigen-binding fragment thereof has one or more of the following biological functions:

(a) binding to human CLDN18.2 with an EC50 of 0.1 µg/ml or less (e.g., 0.05 µg/ml, 0.02 g/ml or less);
  (b) binding to mouse CLDN18.2 with an EC50 of 1 µg/ml or less;
  (c) inducing the killing of a cell expressing human CLDN18.2 (e.g., a tumor cell, such as a tumor cell expressing CLDN18.2) through antibody-dependent cell-mediated cytotoxicity (ADCC);
  (d) inducing the killing of a cell expressing human CLDN18.2 (e.g., a tumor cell, such as a tumor cell expressing CLDN18.2) through complement-dependent cytotoxicity (CDC);
  (e) mediating internalization of CLDN18.2 into a cell (e.g., a tumor cell), for example with an internalization level of at least 10% (e.g., at least 15%, at least 20% or more) as measured by FACS or flow cytometry; the cell has CLDN18.2 expressed on the surface thereof,
  (f) preventing and/or treating a tumor (e.g., a tumor expressing CLDN18.2) in a subject.

In certain preferred embodiments, the antibody or antigen-binding fragment thereof comprises:

(1) VH CDR1 as shown in SEQ ID NO: 3, VH CDR2 as shown in SEQ ID NO: 4 and VH CDR3 as shown in SEQ ID NO: 5; VL CDR1 as shown in SEQ ID NO: 6; VL CDR2 as shown in SEQ ID NO: 7; VL CDR3 as shown in SEQ ID NO: 8; or
  (2) the 3 CDRs of the heavy chain variable region as shown in SEQ ID NO: 1; and the 3 CDRs of the light chain variable region as shown in SEQ ID NO: 2.

In an exemplary embodiment, the antibody or antigen-binding fragment thereof comprises:

(a) a heavy chain variable region (VH) comprising an amino acid sequence selected from the group consisting of:
  (i) the sequence as shown in SEQ ID NO: 1;
  (ii) a sequence having a substitution, deletion or addition of one or several amino acids (e.g., a substitution, deletion or addition of 1, 2, 3, 4, or 5 amino acids) compared to the sequence as shown in SEQ ID NO: 1; or
  (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 1;
  and/or,
  (b) a light chain variable region (VL) comprising an amino acid sequence selected from the group consisting of:
  (iv) the sequence as shown in SEQ ID NO: 2;
  (v) a sequence having a substitution, deletion or addition of one or several amino acids (e.g., a substitution, deletion or addition of 1, 2, 3, 4, or 5 amino acids) compared to the sequence as shown in SEQ ID NO: 2; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 2.

In certain preferred embodiments, the substitution as recited in (ii) or (v) is a conservative substitution.

In certain preferred embodiments, the antibody or antigen-binding fragment thereof comprises: a VH having a sequence as shown in SEQ ID NO: 1, and a VL having a sequence as shown in SEQ ID NO: 2.

In certain preferred embodiments, the antibody or antigen-binding fragment thereof is humanized.

In certain preferred embodiments, the VH of the antibody or antigen-binding fragment thereof comprises a heavy chain variable region (VH) framework region (FR) derived from a human immunoglobulin, and/or the VL of the antibody or antigen-binding fragment thereof comprises a light chain variable region (VL) framework region (FR) derived from a human immunoglobulin.

In such embodiments, the heavy chain variable region FR and/or light chain variable region FR of the antibody or antigen-binding fragment thereof may comprise one or more non-human (e.g., murine) amino acid residues, for example, the heavy chain framework region FR and/or light chain framework region FR may comprise one or more amino acid back mutations, and the corresponding murine amino acid residues are contained in these back mutations.

In another aspect, the present invention provides an antibody or antigen-binding fragment thereof which is capable of specifically binding CLDN18.2, comprising:

(a) a heavy chain variable region (VH) comprising the following 3 complementary determining regions (CDRs):
  (i) VH CDR1, consisting of the following sequence: SEQ ID NO: 11, or a sequence having a substitution, deletion or addition of one or several amino acids (e.g., a substitution, deletion or addition of 1, 2 or 3 amino acids) compared thereto,
  (ii) VH CDR2, consisting of the following sequence: SEQ ID NO: 12, or a sequence having a substitution, deletion or addition of one or several amino acids (e.g., a substitution, deletion or addition of 1, 2 or 3 amino acids) compared thereto, and
  (iii) VH CDR3, consisting of the following sequence: SEQ ID NO: 13, or a sequence having a substitution, deletion or addition of one or several amino acids (e.g., a substitution, deletion or addition of 1, 2 or 3 amino acids) compared thereto;
  and/or
  (b) a light chain variable region (VL) comprising the following 3 complementary determining regions (CDRs):
  (iv) VL CDR1, which consists of the following sequence: SEQ ID NO: 14, or a sequence having a substitution, deletion or addition of one or several amino acids (e.g., a substitution, deletion or addition of 1, 2 or 3 amino acids) compared thereto,
  (v) VL CDR2, which consists of the following sequence: SEQ ID NO: 15, or a sequence having a substitution, deletion or addition of one or several amino acids (e.g., a substitution, deletion or addition of 1, 2 or 3 amino acids) compared thereto, and
  (vi) VL CDR3, consisting of the following sequence: SEQ ID NO: 16, or a sequence having a substitution, deletion or addition of one or several amino acids (e.g., a substitution, deletion or addition of 1, 2 or 3 amino acids) compared thereto.

In certain preferred embodiments, the substitution as recited in any one of (i) to (vi) is a conservative substitution.

In certain preferred embodiments, the VH of the antibody or antigen-binding fragment thereof comprises: VH CDR1 as shown in SEQ ID NO: 11, VH CDR2 as shown in SEQ ID NO: 12, and VH CDR3 as shown in SEQ ID NO: 13; and the VL of the antibody or antigen-binding fragment thereof comprises: VL CDR1 as shown in SEQ ID NO: 14, VL CDR2 as shown in SEQ ID NO: 15, and VL CDR3 as shown in SEQ ID NO: 16.

The present invention also provides an antibody or antigen-binding fragment thereof which is capable of specifically binding to CLDN18.2, comprising a heavy chain variable region and a light chain variable region, wherein the heavy chain variable region comprises the 3 CDRs of the heavy chain variable region as shown in SEQ ID NO: 9; and the light chain variable region contains the 3 CDRs of the light chain variable region as shown in SEQ ID NO: 10.

In certain preferred embodiments, the 3 CDRs of the heavy chain variable region, and/or the 3 CDRs of the light chain variable region, are determined using the Kabat, Chothia, or IMGT numbering system.

In certain preferred embodiments, the antibody or antigen-binding fragment thereof is 2F12 or an antigen-binding fragment thereof, a chimeric antibody thereof, or a humanized antibody thereof, or a variant thereof, in which the variant substantially retains a biological function of the antibody or antigen-binding fragment from which it is derived.

In certain preferred embodiments, the antibody or antigen-binding fragment thereof has one or more of the following biological functions:

(a) binding to human CLDN18.2 with an EC50 of 0.1 μg/ml or less (e.g., 0.05 μg/ml or less);

(b) binding to mouse CLDN18.2 with an EC50 of 0.1 μg/ml or less;

(c) not binding to human CLDN18.1;

(d) inducing the killing of a cell expressing human CLDN18.2 (e.g., a tumor cell, such as a tumor cell expressing CLDN18.2) through antibody-dependent cell-mediated cytotoxicity (ADCC);

(e) inducing the killing of a cell expressing human CLDN18.2 (e.g., a tumor cell, such as a tumor cell expressing CLDN18.2) through complement dependent cytotoxicity (CDC);

(f) preventing and/or treating a tumor (e.g., a tumor expressing CLDN18.2) in a subject.

In certain preferred embodiments, the antibody or antigen-binding fragment thereof comprises:

(1) VH CDR1 as shown in SEQ ID NO: 11, VH CDR2 as shown in SEQ ID NO: 12, VH CDR3 as shown in SEQ ID NO: 13; VL CDR1 as shown in SEQ ID NO: 14; VL CDR2 as shown in SEQ ID NO: 15; VL CDR3 as shown in SEQ ID NO: 16; or (2) the 3 CDRs of the heavy chain variable region as shown in SEQ ID NO: 9; and the 3 CDRs of the light chain variable region as shown in SEQ ID NO: 10.

In an exemplary embodiment, the antibody or antigen-binding fragment thereof comprises:

(a) a heavy chain variable region (VH) comprising an amino acid sequence selected from the group consisting of:

(i) the sequence as shown in SEQ ID NO: 9;

(ii) a sequence having a substitution, deletion or addition of one or several amino acids (e.g., a substitution, deletion or addition of 1, 2, 3, 4 or 5 amino acids) compared to the sequence as shown in SEQ ID NO: 9; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO:9;

and/or, (b) a light chain variable region (VL) comprising an amino acid sequence selected from the group consisting of:

(iv) the sequence as shown in SEQ ID NO: 10;

(v) a sequence having a substitution, deletion or addition of one or several amino acids (e.g., a substitution, deletion or addition of 1, 2, 3, 4 or 5 amino acids) compared to the sequence as shown in SEQ ID NO: 10; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO:10.

In certain preferred embodiments, the substitution as recited in (ii) or (v) is a conservative substitution.

In certain preferred embodiments, the antibody or antigen-binding fragment thereof comprises: a VH having a sequence as shown in SEQ ID NO: 9, and a VL having a sequence as shown in SEQ ID NO: 10.

In certain preferred embodiments, the antibody or antigen-binding fragment thereof is humanized.

In certain preferred embodiments, the VH of the antibody or antigen-binding fragment thereof comprises a heavy chain variable region (VH) framework region (FR) derived from a human immunoglobulin, and/or the VL of the antibody or antigen-binding fragment thereof comprises a light chain variable region (VL) framework region (FR) derived from a human immunoglobulin.

In such embodiments, the heavy chain variable region FR and/or light chain variable region FR of the antibody or antigen-binding fragment thereof may comprise one or more non-human (e.g., murine) amino acid residues, for example, the heavy chain framework region FR and/or light chain framework region FR may comprise one or more amino acid back mutations, and the corresponding murine amino acid residues are contained in these back mutations.

In another aspect, the present invention provides an antibody or antigen-binding fragment thereof which is capable of specifically binding to CLDN18.2, comprising:

(a) a heavy chain variable region (VH) comprising the following 3 complementary determining regions (CDRs):

(i) VH CDR1, consisting of the following sequence: SEQ ID NO: 19, or a sequence having a substitution, deletion or addition of one or several amino acids (e.g., a substitution, deletion or addition of 1, 2 or 3 amino acids) compared thereto, (ii) VH CDR2, which consists of the following sequence: SEQ ID NO: 20, or a sequence having a substitution, deletion or addition of one or several amino acids (e.g., a substitution, deletion or addition of 1, 2 or 3 amino acids) compared thereto, and (iii) VH CDR3, which consists of the following sequence: SEQ ID NO: 21, or a sequence having a substitution, deletion or addition of one or several amino acids (e.g., a substitution, deletion or addition of 1, 2 or 3 amino acids) compared thereto; and/or (b) a light chain variable region (VL) comprising the following 3 complementary determining regions (CDRs):

(iv) VL CDR1, consisting of the following sequence: SEQ ID NO: 22, or a sequence having a substitution, deletion or addition of one or several amino acids (e.g., a substitution, deletion or addition of 1, 2 or 3 amino acids) compared thereto, (v) VL CDR2, which consists of the following sequence: SEQ ID NO: 23, or a sequence having a substitution, deletion or addition of one or several amino acids (e.g., a substitution, deletion or addition of 1, 2 or 3 amino acids) compared thereto, and (vi) VL CDR3, consisting of the following sequence: SEQ ID NO: 24, or a sequence having a substitution, deletion or addition of one or several amino acids (e.g., a substitution, deletion or addition of 1, 2 or 3 amino acids) compared thereto.

In certain preferred embodiments, the substitution as recited in any one of (i) to (vi) is a conservative substitution.

In certain preferred embodiments, the VH of the antibody or antigen-binding fragment thereof comprises: VH CDR1 as shown in SEQ ID NO: 19, VH CDR2 as shown in SEQ ID NO: 20, VH CDR3 as shown in SEQ ID NO: 21; and the VL of the antibody or antigen-binding fragment thereof comprises: VL CDR1 as shown in SEQ ID NO: 22, VL CDR2 as shown in SEQ ID NO: 23, and VL CDR3 as shown in SEQ ID NO: 24.

The present invention also provides an antibody or antigen-binding fragment thereof which is capable of specifically binding to CLDN18.2, comprising a heavy chain variable region and a light chain variable region, wherein the heavy chain variable region comprises the 3 CDRs of the heavy chain variable region as shown in SEQ ID NO: 17; and the light chain variable region comprises the 3 CDRs of the light chain variable region as shown in SEQ ID NO: 18.

In certain preferred embodiments, the 3 CDRs of the heavy chain variable region, and/or the 3 CDRs of the light chain variable region, are determined using the Kabat, Chothia, or IMGT numbering system.

In certain preferred embodiments, the antibody or antigen-binding fragment thereof is 3F2 or an antigen-binding fragment thereof, a chimeric antibody thereof, or a humanized antibody thereof, or a variant thereof, in which the variant substantially retains a biological function of the antibody or antigen-binding fragment from which it is derived.

In certain preferred embodiments, the antibody or antigen-binding fragment thereof has one or more of the following biological functions:

(a) binding to human CLDN18.2 with an EC50 of 0.1 μg/ml or less (e.g., 0.05 μg/ml or less); (b) binding to mouse CLDN18.2 with an EC50 of 0.1 μg/ml or less;

(c) not binding to human CLDN18.1;

(d) inducing the killing of a cell expressing human CLDN18.2 (e.g., a tumor cell, such as a tumor cell expressing CLDN18.2) through antibody-dependent cell-mediated cytotoxicity (ADCC);

(e) inducing the killing of a cell expressing human CLDN18.2 (e.g., a tumor cell, such as a tumor cell expressing CLDN18.2) through complement dependent cytotoxicity (CDC);

(f) preventing and/or treating a tumor (e.g., a tumor expressing CLDN18.2) in a subject.

In certain preferred embodiments, the antibody or antigen-binding fragment thereof comprises:

(1) VH CDR1 as shown in SEQ ID NO: 19, VH CDR2 as shown in SEQ ID NO: 20, VH CDR3 as shown in SEQ ID NO: 21; VL CDR1 as shown in SEQ ID NO: 22, VL CDR2 as shown in SEQ ID NO: 23, VL CDR3 as shown in SEQ ID NO: 24; or (2) the 3 CDRs of the heavy chain variable region as shown in SEQ ID NO: 17; and the 3 CDRs of the light chain variable region as shown in SEQ ID NO: 18.

In an exemplary embodiment, the antibody or antigen-binding fragment thereof comprises:

(a) a heavy chain variable region (VH) comprising an amino acid sequence selected from the group consisting of:

(i) the sequence as shown in SEQ ID NO: 17;

(ii) a sequence having a substitution, deletion or addition of one or several amino acids (e.g., a substitution, deletion or addition of 1, 2, 3, 4 or 5 amino acids) compared to the sequence as shown in SEQ ID NO: 17; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 17; and/or, (b) a light chain variable region (VL) comprising an amino acid sequence selected from the group consisting of:

(iv) the sequence as shown in SEQ ID NO: 18;

(v) a sequence having a substitution, deletion or addition of one or several amino acids (e.g., a substitution, deletion or addition of 1, 2, 3, 4 or 5 amino acids) compared to the sequence as shown in SEQ ID NO: 18; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 18.

In certain preferred embodiments, the substitution as recited in (ii) or (v) is a conservative substitution.

In certain preferred embodiments, the antibody or antigen-binding fragment thereof comprises: a VH having a sequence as shown in SEQ ID NO: 17, and a VL having a sequence as shown in SEQ ID NO: 18.

In certain preferred embodiments, the antibody or antigen-binding fragment thereof is humanized.

In certain preferred embodiments, the VH of the antibody or antigen-binding fragment thereof comprises a heavy chain variable region (VH) framework region (FR) derived from a human immunoglobulin, and/or the VL of the antibody or antigen-binding fragment thereof comprises a light chain variable region (VL) framework region (FR) derived from a human immunoglobulin.

In such embodiments, the heavy chain variable region FR and/or light chain variable region FR of the antibody or antigen-binding fragment thereof may comprise one or more non-human (e.g., murine) amino acid residues, for example, the heavy chain framework region FR and/or light chain framework region FR may comprise one or more amino acid back mutations, and the corresponding murine amino acid residues are contained in these back mutations.

In another aspect, the present invention provides an antibody or antigen-binding fragment thereof which is capable of specifically binding CLDN18.2, comprising:

(a) a heavy chain variable region (VH) comprising the following 3 complementary determining regions (CDRs):

(i) VH CDR1, consisting of the following sequence: SEQ ID NO: 27, or a sequence having a substitution, deletion or addition of one or several amino acids (e.g., a substitution, deletion or addition of 1, 2 or 3 amino acids) compared thereto;

(ii) VH CDR2, consisting of the following sequence: SEQ ID NO: 28, or a sequence having a substitution, deletion or addition of one or several amino acids (e.g., a substitution, deletion or addition of 1, 2 or 3 amino acids) compared thereto; and (iii) VH CDR3, consisting of the following sequence: SEQ ID NO: 29, or a sequence having a substitution, deletion or addition of one or several amino acids (e.g., a substitution, deletion or addition of 1, 2 or 3 amino acids) compared thereto;

and/or (b) a light chain variable region (VL) comprising the following 3 complementary determining regions (CDRs):

(iv) VL CDR1, consisting of the following sequence: SEQ ID NO: 30, or a sequence having a substitution, deletion or addition of one or several amino acids (e.g., a substitution, deletion or addition of 1, 2 or 3 amino acids) compared thereto, (v) VL CDR2, consisting of the following sequence: SEQ ID NO: 31, or a sequence having a substitution, deletion or addition of one or several amino acids (e.g., a substitution, deletion or addition of 1, 2 or 3 amino acids) compared thereto, and (vi) VL CDR3, consisting of the following sequence: SEQ ID NO: 32, or a sequence having a substitution, deletion or addition of one or several amino acids (e.g., a substitution, deletion or addition of 1, 2 or 3 amino acids) compared thereto.

In certain preferred embodiments, the substitution as recited in any one of (i) to (vi) is a conservative substitution.

In certain preferred embodiments, the VH of the antibody or antigen-binding fragment thereof comprises: VH CDR1 as shown in SEQ ID NO: 27, VH CDR2 as shown in SEQ ID NO: 28, VH CDR3 as shown in SEQ ID NO: 29; and, the VL of the antibody or antigen-binding fragment thereof comprises: VL CDR1 as shown in SEQ ID NO: 30, VL CDR2 as shown in SEQ ID NO: 31, and VL CDR3 as shown in SEQ ID NO: 32.

The present invention also provides an antibody or antigen-binding fragment thereof which is capable of specifically binding to CLDN18.2, comprising a heavy chain variable region and a light chain variable region, wherein the heavy chain variable region comprises the 3 CDRs of the heavy chain variable region as shown in SEQ ID NO: 25; and the light chain variable region comprises the 3 CDRs of the light chain variable region as shown in SEQ ID NO: 26.

In certain preferred embodiments, the 3 CDRs of the heavy chain variable region, and/or the 3 CDRs of the light chain variable region, are determined using the Kabat, Chothia, or IMGT numbering system.

In certain preferred embodiments, the antibody or antigen-binding fragment thereof is 5F9 or an antigen-binding fragment thereof, a chimeric antibody thereof, or a humanized antibody thereof, or a variant thereof, in which the variant substantially retains a biological function of the antibody or antigen-binding fragment from which it is derived.

In certain preferred embodiments, the antibody or antigen-binding fragment thereof has one or more of the following biological functions:

(a) binding to human CLDN18.2 with an EC50 of 0.5 µg/ml or less;

(b) binding to mouse CLDN18.2 with an EC50 of 0.2 µg/ml or less;

(c) inducing the killing of a cell expressing human CLDN18.2 (e.g., a tumor cell, such as a tumor cell expressing CLDN18.2) through antibody-dependent cell-mediated cytotoxicity (ADCC);

(d) inducing the killing of a cell expressing human CLDN18.2 (e.g., a tumor cell, such as a tumor cell expressing CLDN18.2) through complement-dependent cytotoxicity (CDC);

(e) mediating internalization of CLDN18.2 into a cell (e.g., a tumor cell), for example, with an internalization level of at least 10% (e.g., at least 15%, at least 20% or more) as measured by FACS or flow cytometry; the cell has CLDN18.2 expressed on the surface thereof, (f) preventing and/or treating a tumor (e.g., a tumor expressing CLDN18.2) in a subject.

In certain preferred embodiments, the antibody or antigen-binding fragment thereof comprises:

(1) VH CDR1 as shown in SEQ ID NO: 27, VH CDR2 as shown in SEQ ID NO: 28, VH CDR3 as shown in SEQ ID NO: 29; VL CDR1 as shown in SEQ ID NO: 30, VL CDR2 as shown in SEQ ID NO: 31, VL CDR3 as shown in SEQ ID NO: 32; or (2) the 3 CDRs of the heavy chain variable region as shown in SEQ ID NO: 25; and the 3 CDRs of the light chain variable region shown in SEQ ID NO: 26.

In an exemplary embodiment, the antibody or antigen-binding fragment thereof comprises:

(a) a heavy chain variable region (VH) comprising an amino acid sequence selected from the group consisting of:

(i) the sequence as shown in SEQ ID NO: 25;

(ii) a sequence having a substitution, deletion or addition of one or several amino acids (e.g., a substitution, deletion or addition of 1, 2, 3, 4, or 5 amino acids) compared to the sequence as shown in SEQ ID NO: 25; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 25;

and/or, (b) a light chain variable region (VL) comprising an amino acid sequence selected from the group consisting of:

(iv) the sequence as shown in SEQ ID NO: 26;

(v) a sequence having a substitution, deletion or addition of one or several amino acids (e.g., a substitution, deletion or addition of 1, 2, 3, 4, or 5 amino acids) compared to the sequence as shown in SEQ ID NO: 26; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 26.

In certain preferred embodiments, the substitution as recited in (ii) or (v) is a conservative substitution.

In certain preferred embodiments, the antibody or antigen-binding fragment thereof comprises: a VH having a sequence as shown in SEQ ID NO: 25, and a VL having a sequence as shown in SEQ ID NO: 26.

In certain preferred embodiments, the antibody or antigen-binding fragment thereof is humanized.

In certain preferred embodiments, the VH of the antibody or antigen-binding fragment thereof comprises a heavy chain variable region (VH) framework region (FR) derived from a human immunoglobulin, and/or the VL of the antibody or antigen-binding fragment thereof comprises a light chain variable region (VL) framework region (FR) derived from a human immunoglobulin.

In such embodiments, the heavy chain variable region FR and/or light chain variable region FR of the antibody or antigen-binding fragment thereof may comprise one or more non-human (e.g., murine) amino acid residues, for example, the heavy chain framework region FR and/or light chain framework region FR may comprise one or more amino acid back mutations, and the corresponding murine amino acid residues are contained in these back mutations.

In another aspect, the present invention provides an antibody or antigen-binding fragment thereof which is capable of specifically binding to CLDN18.2, comprising:

(a) a heavy chain variable region (VH) comprising the following 3 complementary determining regions (CDRs):

(i) VH CDR1, consisting of the following sequence: SEQ ID NO: 35, or a sequence having a substitution, deletion or addition of one or several amino acids (e.g., a substitution, deletion or addition of 1, 2 or 3 amino acids) compared thereto, (ii) VH CDR2, consisting of the following sequence: SEQ ID NO: 36, or a sequence having a substitution, deletion or addition of one or several amino acids (e.g., a substitution, deletion or addition of 1, 2 or 3 amino acids) compared thereto, and (iii) VH CDR3, consisting of the following sequence: SEQ ID NO: 37, or a sequence having a substitution, deletion or addition of one or several amino acids (e.g., a substitution, deletion or addition of 1, 2 or 3 amino acids) compared thereto;

and/or (b) a light chain variable region (VL) comprising the following 3 complementary determining regions (CDRs):

(iv) VL CDR1, which consists of the following sequence: SEQ ID NO: 38, or a sequence having a substitution, deletion or addition of one or several amino acids (e.g., a substitution, deletion or addition of 1, 2 or 3 amino acids) compared thereto, (v) VL CDR2, which consists of the following sequence: SEQ ID NO: 39, or a sequence having a substitution, deletion or addition of one or several amino acids (e.g., a substitution, deletion or addition of 1, 2 or 3 amino acids) compared thereto, and (vi) VL CDR3, consisting of the following sequence: SEQ ID NO: 40, or a sequence having a substitution, deletion or addition of one or several amino acids (e.g., a substitution, deletion or addition of 1, 2 or 3 amino acids) compared thereto.

In certain preferred embodiments, the substitution as recited in any one of (i) to (vi) is a conservative substitution.

In certain preferred embodiments, the VH of the antibody or antigen-binding fragment thereof comprises: VH CDR1 as shown in SEQ ID NO: 35, VH CDR2 as shown in SEQ ID NO: 36, VH CDR3 as shown in SEQ ID NO: 37; and the VL of the antibody or antigen-binding fragment thereof comprises: VL CDR1 as shown in SEQ ID NO: 38, VL CDR2 as shown in SEQ ID NO: 39, and VL CDR3 as shown in SEQ ID NO: 40.

The present invention also provides an antibody or antigen-binding fragment thereof which is capable of specifically binding to CLDN18.2, comprising a heavy chain variable region and a light chain variable region, wherein the heavy chain variable region comprises the 3 CDRs of the heavy chain variable region as shown in SEQ ID NO: 33; and the light chain variable region comprises the 3 CDRs of the light chain variable region as shown in SEQ ID NO: 34.

In certain preferred embodiments, the 3 CDRs of the heavy chain variable region, and/or the 3 CDRs of the light chain variable region, are determined using the Kabat, Chothia, or IMGT numbering system.

In certain preferred embodiments, the antibody or antigen-binding fragment thereof is 9F3 or an antigen-binding fragment thereof, a chimeric antibody thereof, or a humanized antibody thereof, or a variant thereof, in which the variant substantially retains a biological function of the antibody or antigen-binding fragment from which it is derived.

In certain preferred embodiments, the antibody or antigen-binding fragment thereof has one or more of the following biological functions:

(a) binding to human CLDN18.2 with an EC50 of 0.2 μg/ml or less;

(b) binding to mouse CLDN18.2 with an EC50 of 0.1 μg/ml or less;

(c) not binding to human CLDN18.1;

(d) inducing the killing of a cell expressing human CLDN18.2 (e.g., a tumor cell, such as a tumor cell expressing CLDN18.2) through antibody-dependent cell-mediated cytotoxicity (ADCC);

(e) inducing the killing of a cell expressing human CLDN18.2 (e.g., a tumor cell, such as a tumor cell expressing CLDN18.2) through complement dependent cytotoxicity (CDC);

(f) preventing and/or treating a tumor (e.g., a tumor expressing CLDN18.2) in a subject.

In certain preferred embodiments, the antibody or antigen-binding fragment thereof comprises:

(1) VH CDR1 as shown in SEQ ID NO: 35, VH CDR2 as shown in SEQ ID NO: 36, VH CDR3 as shown in SEQ ID NO: 37; VL CDR1 as shown in SEQ ID NO: 38, VL CDR2 as shown in SEQ ID NO: 39, VL CDR3 as shown in SEQ ID NO: 40; or (2) the 3 CDRs of the heavy chain variable region as shown in SEQ ID NO: 33; and the 3 CDRs of the light chain variable region as shown in SEQ ID NO: 34.

In an exemplary embodiment, the antibody or antigen-binding fragment thereof comprises:

(a) a heavy chain variable region (VH) comprising an amino acid sequence selected from the group consisting of:

(i) the sequence as shown in SEQ ID NO: 33;

(ii) a sequence having a substitution, deletion or addition of one or several amino acids (e.g., a substitution, deletion or addition of 1, 2, 3, 4 or 5 amino acids) compared to the sequence as shown in SEQ ID NO: 33; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 33; and/or, (b) a light chain variable region (VL) comprising an amino acid sequence selected from the group consisting of:

(iv) the sequence as shown in SEQ ID NO: 34;

(v) a sequence having a substitution, deletion or addition of one or several amino acids (e.g., a substitution, deletion or addition of 1, 2, 3, 4 or 5 amino acids) compared to the sequence as shown in SEQ ID NO: 34; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO:34.

In certain preferred embodiments, the substitution as recited in (ii) or (v) is a conservative substitution.

In certain preferred embodiments, the antibody or antigen-binding fragment thereof comprises: a VH having a sequence as shown in SEQ ID NO: 33, and a VL having a sequence as shown in SEQ ID NO: 34.

In certain preferred embodiments, the antibody or antigen-binding fragment thereof is humanized.

In certain preferred embodiments, the VH of the antibody or antigen-binding fragment thereof comprises a heavy chain variable region (VH) framework region (FR) derived from a human immunoglobulin, and/or the VL of the antibody or antigen-binding fragment thereof comprises a light chain variable region (VL) framework region (FR) derived from a human immunoglobulin.

In such embodiments, the heavy chain variable region FR and/or light chain variable region FR of the antibody or antigen-binding fragment thereof may comprise one or more non-human (e.g., murine) amino acid residues, for example, the heavy chain framework region FR and/or light chain framework region FR may comprise one or more amino acid back mutations, and the corresponding murine amino acid residues are contained in these back mutations.

In another aspect, the present invention provides an antibody or antigen-binding fragment thereof which is capable of specifically binding to CLDN18.2, comprising:

(a) a heavy chain variable region (VH) comprising the following 3 complementary determining regions (CDRs):

(i) VH CDR1, consisting of the following sequence: SEQ ID NO: 43, or a sequence having a substitution, deletion or addition of one or several amino acids (e.g., a substitution, deletion or addition of 1, 2 or 3 amino acids) compared thereto, (ii) VH CDR2, which consists of the following sequence: SEQ ID NO: 44, or a sequence having a substitution, deletion or addition of one or several amino acids (e.g., a substitution, deletion or addition of 1, 2 or 3 amino acids) compared thereto, and (iii) VH CDR3, which consists of the following sequence: SEQ ID NO: 45, or a sequence having a substitution, deletion or addition of one or several amino acids (e.g., a substitution, deletion or addition of 1, 2 or 3 amino acids) compared thereto; and/or (b) a light chain variable region (VL) comprising the following 3 complementary determining regions (CDRs):

(iv) VL CDR1, consisting of the following sequence: SEQ ID NO: 46, or a sequence having a substitution, deletion or addition of one or several amino acids (e.g., a substitution, deletion or addition of 1, 2 or 3 amino acids) compared thereto, (v) VL CDR2, which consists of the following sequence: SEQ ID NO: 47, or a sequence having a substitution, deletion or addition of one or several amino acids (e.g., a substitution, deletion or addition of 1, 2 or 3 amino acids) compared thereto, and (vi) VL CDR3, consisting of the following sequence: SEQ ID NO: 48, or a sequence having a substitution, deletion or addition of one or several amino acids (e.g., a substitution, deletion or addition of 1, 2 or 3 amino acids) compared thereto.

In certain preferred embodiments, the substitution as recited in any one of (i) to (vi) is a conservative substitution.

In certain preferred embodiments, the VH of the antibody or antigen-binding fragment thereof comprises: VH CDR1 as shown in SEQ ID NO: 43, VH CDR2 as shown in SEQ ID NO: 44, VH CDR3 as shown in SEQ ID NO: 45; and the VL of the antibody or antigen-binding fragment thereof comprises: VL CDR1 as shown in SEQ ID NO: 46, VL CDR2 as shown in SEQ ID NO: 47, and VL CDR3 as shown in SEQ ID NO: 48.

The present invention also provides an antibody or antigen-binding fragment thereof which is capable of specifically binding to CLDN18.2, comprising a heavy chain variable region and a light chain variable region, wherein the heavy chain variable region comprises the 3 CDRs of the heavy chain variable region as shown in SEQ ID NO: 41; and the light chain variable region comprises the 3 CDRs of the light chain variable region as shown in SEQ ID NO: 42.

In certain preferred embodiments, the 3 CDRs of the heavy chain variable region, and/or the 3 CDRs of the light chain variable region, are determined using the Kabat, Chothia, or IMGT numbering system.

In certain preferred embodiments, the antibody or antigen-binding fragment thereof is 10B11 or an antigen-binding fragment thereof, a chimeric antibody thereof, or a humanized antibody thereof, or a variant thereof, in which the variant substantially retains a biological function of the antibody or antigen-binding fragment from which it is derived.

In certain preferred embodiments, the antibody or antigen-binding fragment thereof has one or more of the following biological functions:

(a) binding to human CLDN18.2 with an EC50 of 0.1 µg/ml or less (e.g., 0.05 µg/ml or less); (b) binding to mouse CLDN18.2 with an EC50 of 0.1 µg/ml or less;

(c) not binding to human CLDN18.1;

(d) inducing the killing of a cell expressing human CLDN18.2 (e.g., a tumor cell, such as a tumor cell expressing CLDN18.2) through antibody-dependent cell-mediated cytotoxicity (ADCC);

(e) inducing the killing of a cell expressing human CLDN18.2 (e.g., a tumor cell, such as a tumor cell expressing CLDN18.2) through complement dependent cytotoxicity (CDC);

(f) preventing and/or treating a tumor (e.g., a tumor expressing CLDN18.2) in a subject.

In certain preferred embodiments, the antibody or antigen-binding fragment thereof comprises:

(1) VH CDR1 as shown in SEQ ID NO: 43, VH CDR2 as shown in SEQ ID NO: 44, VH CDR3 as shown in SEQ ID NO: 45; VL CDR1 as shown in SEQ ID NO: 46, VL CDR2 as shown in SEQ ID NO: 47, VL CDR3 as shown in SEQ ID NO: 48; or (2) the 3 CDRs of the heavy chain variable region as shown in SEQ ID NO: 41; and the 3 CDRs of the light chain variable region as shown in SEQ ID NO: 42.

In an exemplary embodiment, the antibody or antigen-binding fragment thereof comprises:

(a) a heavy chain variable region (VH) comprising an amino acid sequence selected from the group consisting of:

(i) the sequence as shown in SEQ ID NO: 41;

(ii) a sequence having a substitution, deletion or addition of one or several amino acids (e.g., a substitution, deletion or addition of 1, 2, 3, 4 or 5 amino acids) compared to the sequence as shown in SEQ ID NO: 41; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 41;

and/or, (b) a light chain variable region (VL) comprising an amino acid sequence selected from the group consisting of:

(iv) the sequence as shown in SEQ ID NO: 42;

(v) a sequence having a substitution, deletion or addition of one or several amino acids (e.g., a substitution, deletion or addition of 1, 2, 3, 4 or 5 amino acids) compared to the sequence as shown in SEQ ID NO: 42; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 42.

In certain preferred embodiments, the substitution as recited in (ii) or (v) is a conservative substitution.

In certain preferred embodiments, the antibody or antigen-binding fragment thereof comprises: a VH having a sequence as shown in SEQ ID NO: 41, and a VL having a sequence as shown in SEQ ID NO: 42.

In certain preferred embodiments, the antibody or antigen-binding fragment thereof is humanized.

In certain preferred embodiments, the VH of the antibody or antigen-binding fragment thereof comprises a heavy chain variable region (VH) framework region (FR) derived from a human immunoglobulin, and/or the VL of the antibody or antigen-binding fragment thereof comprises a light chain variable region (VL) framework region (FR) derived from a human immunoglobulin.

In such embodiments, the heavy chain variable region FR and/or light chain variable region FR of the antibody or antigen-binding fragment thereof may comprise one or more non-human (e.g., murine) amino acid residues, for example, the heavy chain framework region FR and/or light chain framework region FR may contain one or more amino acid back mutations, and the corresponding murine amino acid residues are contained in these back mutations.

In another aspect, the present invention provides an antibody or antigen-binding fragment thereof which is capable of specifically binding to CLDN18.2, comprising:

(a) a heavy chain variable region (VH) comprising the following 3 complementary determining regions (CDRs):

(i) VH CDR1, consisting of the following sequence: SEQ ID NO: 51, or a sequence having a substitution, deletion or addition of one or several amino acids (e.g., a substitution, deletion or addition of 1, 2 or 3 amino acids) compared thereto;

(ii) VH CDR2, consisting of the following sequence: SEQ ID NO: 52, or a sequence having a substitution, deletion or addition of one or several amino acids (e.g., a substitution, deletion or addition of 1, 2 or 3 amino acids) compared thereto; and (iii) VH CDR3, consisting of the following sequence: SEQ ID NO: 53, or a sequence having a substitution, deletion or addition of one or several amino acids (e.g., a substitution, deletion or addition of 1, 2 or 3 amino acids) compared thereto;

and/or (b) a light chain variable region (VL) comprising the following 3 complementary determining regions (CDRs):

(iv) VL CDR1, consisting of the following sequence: SEQ ID NO: 54, or a sequence having a substitution, deletion or addition of one or several amino acids (e.g., a substitution, deletion or addition of 1, 2 or 3 amino acids) compared thereto, (v) VL CDR2, consisting of the following sequence: SEQ ID NO: 55, or a sequence having a substitution, deletion or addition of one or several amino acids (e.g., a substitution, deletion or addition of 1, 2 or 3 amino acids) compared thereto, and (vi) VL CDR3, consisting of the following sequence: SEQ ID NO: 56, or a sequence having a substitution, deletion or addition of one or several amino acids (e.g., a substitution, deletion or addition of 1, 2 or 3 amino acids) compared thereto.

In certain preferred embodiments, the substitution as recited in any one of (i) to (vi) is a conservative substitution.

In certain preferred embodiments, the VH of the antibody or antigen-binding fragment thereof comprises: VH CDR1 as shown in SEQ ID NO: 51, VH CDR2 as shown in SEQ ID NO: 52, VH CDR3 as shown in SEQ ID NO: 53; and, the VL of the antibody or antigen-binding fragment thereof comprises: VL CDR1 as shown in SEQ ID NO: 54, VL CDR2 as shown in SEQ ID NO: 55, and VL CDR3 as shown in SEQ ID NO: 56.

The present invention also provides an antibody or antigen-binding fragment thereof which is capable of specifically binding to CLDN18.2, comprising a heavy chain variable region and a light chain variable region, wherein the heavy chain variable region comprises the 3 CDRs of the heavy chain variable region as shown in SEQ ID NO: 49; and the light chain variable region comprises the 3 CDRs of the light chain variable region shown in SEQ ID NO: 50.

In certain preferred embodiments, the 3 CDRs of the heavy chain variable region, and/or the 3 CDRs of the light chain variable region, are determined using the Kabat, Chothia, or IMGT numbering system.

In certain preferred embodiments, the antibody or antigen-binding fragment thereof is 27B5 or an antigen-binding fragment thereof, a chimeric antibody thereof, or a humanized antibody thereof, or a variant thereof, in which the variant substantially retaining a biological function of the antibody or antigen-binding fragment from which it is derived.

In certain preferred embodiments, the antibody or antigen-binding fragment thereof has one or more of the following biological functions:

(a) binding to human CLDN18.2 with an EC50 of 0.2 μg/ml or less;

(b) binding to mouse CLDN18.2 with an EC50 of 0.1 μg/ml or less;

(c) not binding to human CLDN18.1;

(d) inducing the killing of a cell expressing human CLDN18.2 (e.g., a tumor cell, such as a tumor cell expressing CLDN18.2) through antibody-dependent cell-mediated cytotoxicity (ADCC);

(e) inducing the killing of a cell expressing human CLDN18.2 (e.g., a tumor cell, such as a tumor cell expressing CLDN18.2) through complement-dependent cytotoxicity (CDC);

(f) preventing and/or treating a tumor (e.g., a tumor expressing CLDN18.2) in a subject.

In certain preferred embodiments, the antibody or antigen-binding fragment thereof comprises:

(1) VH CDR1 as shown in SEQ ID NO: 51, VH CDR2 as shown in SEQ ID NO: 52, VH CDR3 as shown in SEQ ID NO: 53; VL CDR1 as shown in SEQ ID NO: 54, VL CDR2 as shown in SEQ ID NO: 55, VL CDR3 as shown in SEQ ID NO: 56; or (2) the 3 CDRs of the heavy chain variable region as shown in SEQ ID NO: 49; and the 3 CDRs of the light chain variable region as shown in SEQ ID NO: 50.

In an exemplary embodiment, the antibody or antigen-binding fragment thereof comprises:

(a) a heavy chain variable region (VH) comprising an amino acid sequence selected from the group consisting of:

(i) the sequence as shown in SEQ ID NO: 49;

(ii) a sequence having a substitution, deletion or addition of one or several amino acids (e.g., a substitution, deletion or addition of 1, 2, 3, 4, or 5 amino acids) compared to the sequence as shown in SEQ ID NO: 49; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 49;

and/or, (b) a light chain variable region (VL) comprising an amino acid sequence selected from the group consisting of:

(iv) the sequence as shown in SEQ ID NO: 50;

(v) a sequence having a substitution, deletion or addition of one or several amino acids (e.g., a substitution, deletion or addition of 1, 2, 3, 4, or 5 amino acids) compared to the sequence as shown in SEQ ID NO: 50; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 50.

In certain preferred embodiments, the substitution as recited in (ii) or (v) is a conservative substitution.

In certain preferred embodiments, the antibody or antigen-binding fragment thereof comprises: a VH having a sequence as shown in SEQ ID NO: 49, and a VL having a sequence as shown in SEQ ID NO: 50.

In certain preferred embodiments, the antibody or antigen-binding fragment thereof is humanized.

In certain preferred embodiments, the VH of the antibody or antigen-binding fragment thereof comprises a heavy chain variable region (VH) framework region (FR) derived from a human immunoglobulin, and/or the VL of the antibody or antigen-binding fragment thereof comprises a light chain variable region (VL) framework region (FR) derived from a human immunoglobulin.

In such embodiments, the heavy chain variable region FR and/or light chain variable region FR of the antibody or antigen-binding fragment thereof may comprise one or more non-human (e.g., murine) amino acid residues, for example, the heavy chain framework region FR and/or light chain framework region FR may comprise one or more amino acid back mutations, and the corresponding murine amino acid residues are contained in these back mutations.

In another aspect, the present invention provides an antibody or antigen-binding fragment thereof which is capable of specifically binding to CLDN18.2, comprising:

(a) a heavy chain variable region (VH) comprising the following 3 complementary determining regions (CDRs):

(i) VH CDR1, consisting of the following sequence: SEQ ID NO: 59, or a sequence having a substitution, deletion or addition of one or several amino acids (e.g., a substitution, deletion or addition of 1, 2 or 3 amino acids) compared thereto;

(ii) VH CDR2, consisting of the following sequence: SEQ ID NO: 60, or a sequence having a substitution, deletion or addition of one or several amino acids (e.g., a substitution, deletion or addition of 1, 2 or 3 amino acids) compared thereto; and (iii) VH CDR3, consisting of the following sequence: SEQ ID NO: 61, or a sequence having a substitution, deletion or addition of one or several amino acids (e.g., a substitution, deletion or addition of 1, 2 or 3 amino acids) compared thereto;

and/or (b) a light chain variable region (VL) comprising the following 3 complementary determining regions (CDRs):

(iv) VL CDR1, consisting of the following sequence: SEQ ID NO: 62, or a sequence having a substitution, deletion or addition of one or several amino acids (e.g., a substitution, deletion or addition of 1, 2 or 3 amino acids) compared thereto, (v) VL CDR2, consisting of the following sequence: SEQ ID NO: 63, or a sequence having a substitution, deletion or addition of one or several amino acids (e.g., a substitution, deletion or addition of 1, 2 or 3 amino acids) compared thereto, and (vi) VL CDR3, consisting of the following sequence: SEQ ID NO: 64, or a sequence having a substitution, deletion or addition of one or several amino acids (e.g., a substitution, deletion or addition of 1, 2 or 3 amino acids) compared thereto.

In certain preferred embodiments, the substitution as recited in any one of (i) to (vi) is a conservative substitution.

In certain preferred embodiments, the VH of the antibody or antigen-binding fragment thereof comprises: VH CDR1 as shown in SEQ ID NO: 59, VH CDR2 as shown in SEQ ID NO: 60, VH CDR3 as shown in SEQ ID NO: 61; and, the VL of the antibody or antigen-binding fragment thereof comprises: VL CDR1 as shown in SEQ ID NO: 62, VL CDR2 as shown in SEQ ID NO: 63, and VL CDR3 as shown in SEQ ID NO: 64.

The present invention also provides an antibody or antigen-binding fragment thereof which is capable of specifically binding to CLDN18.2, comprising a heavy chain variable region and a light chain variable region, wherein the heavy chain variable region comprises the 3 CDRs of the heavy chain variable region as shown in SEQ ID NO: 57;

and the light chain variable region comprises the 3 CDRs of the light chain variable region shown in SEQ ID NO: 58.

In certain preferred embodiments, the 3 CDRs of the heavy chain variable region, and/or the 3 CDRs of the light chain variable region, are determined using the Kabat, Chothia, or IMGT numbering system.

In certain preferred embodiments, the antibody or antigen-binding fragment thereof is 37B1 or an antigen-binding fragment thereof, a chimeric antibody thereof, or a humanized antibody thereof, or a variant thereof, in which the variant substantially retaining a biological function of the antibody or antigen-binding fragment from which it is derived.

In certain preferred embodiments, the antibody or antigen-binding fragment thereof has one or more of the following biological functions:

(a) binding to human CLDN18.2 with an EC50 of 0.1 μg/ml or less (e.g., 0.05 μg/ml or less);
   (b) binding to mouse CLDN18.2 with an EC50 of 0.1 μg/ml or less;
   (c) not binding to human CLDN18.1;
   (d) inducing the killing of a cell expressing human CLDN18.2 (e.g., a tumor cell, such as a tumor cell expressing CLDN18.2) through antibody-dependent cell-mediated cytotoxicity (ADCC);
   (e) inducing the killing of a cell expressing human CLDN18.2 (e.g., a tumor cell, such as a tumor cell expressing CLDN18.2) through complement-dependent cytotoxicity (CDC);
   (f) preventing and/or treating a tumor (e.g., a tumor expressing CLDN18.2) in a subject.

In certain preferred embodiments, the antibody or antigen-binding fragment thereof comprises:

(1) VH CDR1 as shown in SEQ ID NO: 59, VH CDR2 as shown in SEQ ID NO: 60, VH CDR3 as shown in SEQ ID NO: 61; VL CDR1 as shown in SEQ ID NO: 62, VL CDR2 as shown in SEQ ID NO: 63, VL CDR3 as shown in SEQ ID NO: 64; or
   (2) the 3 CDRs of the heavy chain variable region as shown in SEQ ID NO: 57; and the 3 CDRs of the light chain variable region as shown in SEQ ID NO: 58.

In an exemplary embodiment, the antibody or antigen-binding fragment thereof comprises:

(a) a heavy chain variable region (VH) comprising an amino acid sequence selected from the group consisting of:
   (i) the sequence as shown in SEQ ID NO: 57;
   (ii) a sequence having a substitution, deletion or addition of one or several amino acids (e.g., a substitution, deletion or addition of 1, 2, 3, 4, or 5 amino acids) compared to the sequence as shown in SEQ ID NO: 57; or
   (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 57;
   and/or,
   (b) a light chain variable region (VL) comprising an amino acid sequence selected from the group consisting of:
   (iv) the sequence as shown in SEQ ID NO: 58;
   (v) a sequence having a substitution, deletion or addition of one or several amino acids (e.g., a substitution, deletion or addition of 1, 2, 3, 4, or 5 amino acids) compared to the sequence as shown in SEQ ID NO: 58; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 58.

In certain preferred embodiments, the substitution as recited in (ii) or (v) is a conservative substitution.

In certain preferred embodiments, the antibody or antigen-binding fragment thereof comprises: a VH having a sequence as shown in SEQ ID NO: 57, and a VL having a sequence as shown in SEQ ID NO: 58.

In certain preferred embodiments, the antibody or antigen-binding fragment thereof is humanized.

In certain preferred embodiments, the VH of the antibody or antigen-binding fragment thereof comprises a heavy chain variable region (VH) framework region (FR) derived from a human immunoglobulin, and/or the VL of the antibody or antigen-binding fragment thereof comprises a light chain variable region (VL) framework region (FR) derived from a human immunoglobulin.

In such embodiments, the heavy chain variable region FR and/or light chain variable region FR of the antibody or antigen-binding fragment thereof may comprise one or more non-human (e.g., murine) amino acid residues, for example, the heavy chain framework region FR and/or light chain framework region FR may comprise one or more amino acid back mutations, and the corresponding murine amino acid residues are contained in these back mutations.

In another aspect, the present invention provides an antibody or antigen-binding fragment thereof which is capable of specifically binding to CLDN18.2, comprising:

(a) a heavy chain variable region (VH) comprising the following 3 complementary determining regions (CDRs):
   (i) VH CDR1, consisting of the following sequence: SEQ ID NO: 67, or a sequence having a substitution, deletion or addition of one or several amino acids (e.g., a substitution, deletion or addition of 1, 2 or 3 amino acids) compared thereto;
   (ii) VH CDR2, consisting of the following sequence: SEQ ID NO: 68, or a sequence having a substitution, deletion or addition of one or several amino acids (e.g., a substitution, deletion or addition of 1, 2 or 3 amino acids) compared thereto; and
   (iii) VH CDR3, consisting of the following sequence: SEQ ID NO: 69, or a sequence having a substitution, deletion or addition of one or several amino acids (e.g., a substitution, deletion or addition of 1, 2 or 3 amino acids) compared thereto;
   and/or
   (b) a light chain variable region (VL) comprising the following 3 complementary determining regions (CDRs):
   (iv) VL CDR1, consisting of the following sequence: SEQ ID NO: 70, or a sequence having a substitution, deletion or addition of one or several amino acids (e.g., a substitution, deletion or addition of 1, 2 or 3 amino acids) compared thereto,
   (v) VL CDR2, consisting of the following sequence: SEQ ID NO: 71, or a sequence having a substitution, deletion or addition of one or several amino acids (e.g., a substitution, deletion or addition of 1, 2 or 3 amino acids) compared thereto, and
   (vi) VL CDR3, consisting of the following sequence: SEQ ID NO: 72, or a sequence having a substitution, deletion or addition of one or several amino acids (e.g., a substitution, deletion or addition of 1, 2 or 3 amino acids) compared thereto.

In certain preferred embodiments, the substitution as recited in any one of (i) to (vi) is a conservative substitution.

In certain preferred embodiments, the VH of the antibody or antigen-binding fragment thereof comprises: VH CDR1 as shown in SEQ ID NO: 67, VH CDR2 as shown in SEQ ID NO: 68, VH CDR3 as shown in SEQ ID NO: 69; and, the VL of the antibody or antigen-binding fragment thereof comprises: VL CDR1 as shown in SEQ ID NO: 70, VL CDR2 as shown in SEQ ID NO: 71, and VL CDR3 as shown in SEQ ID NO: 72.

The present invention also provides an antibody or antigen-binding fragment thereof which is capable of specifically binding to CLDN18.2, comprising a heavy chain variable region and a light chain variable region, wherein the heavy chain variable region comprises the 3 CDRs of the heavy chain variable region as shown in SEQ ID NO: 65; and the light chain variable region comprises the 3 CDRs of the light chain variable region shown in SEQ ID NO: 66.

In certain preferred embodiments, the 3 CDRs of the heavy chain variable region, and/or the 3 CDRs of the light chain variable region, are determined using the Kabat, Chothia, or IMGT numbering system.

In certain preferred embodiments, the antibody or antigen-binding fragment thereof is 44A8 or an antigen-binding fragment thereof, a chimeric antibody thereof, or a humanized antibody thereof, or a variant thereof, in which the variant substantially retaining a biological function of the antibody or antigen-binding fragment from which it is derived.

In certain preferred embodiments, the antibody or antigen-binding fragment thereof has one or more of the following biological functions:

(a) binding to human CLDN18.2 with an EC50 of 0.1 µg/ml or less;

(b) binding to mouse CLDN18.2 with an EC50 of 0.1 µg/ml or less;

(c) not binding to human CLDN18.1;

(d) inducing the killing of a cell expressing human CLDN18.2 (e.g., a tumor cell, such as a tumor cell expressing CLDN18.2) through antibody-dependent cell-mediated cytotoxicity (ADCC);

(e) inducing the killing of a cell expressing human CLDN18.2 (e.g., a tumor cell, such as a tumor cell expressing CLDN18.2) through complement-dependent cytotoxicity (CDC);

(f) mediating internalization of CLDN18.2 into a cell (e.g., a tumor cell), for example, with an internalization level of at least 10% (e.g., at least 15%, at least 20% or more) as measured by FACS or flow cytometry; the cell has CLDN18.2 expressed on the surface thereof;

(g) preventing and/or treating a tumor (e.g., a tumor expressing CLDN18.2) in a subject.

In certain preferred embodiments, the antibody or antigen-binding fragment thereof comprises:

(1) VH CDR1 as shown in SEQ ID NO: 67, VH CDR2 as shown in SEQ ID NO: 68, VH CDR3 as shown in SEQ ID NO: 69; VL CDR1 as shown in SEQ ID NO: 70, VL CDR2 as shown in SEQ ID NO: 71, VL CDR3 as shown in SEQ ID NO: 72; or (2) the 3 CDRs of the heavy chain variable region as shown in SEQ ID NO: 65; and the 3 CDRs of the light chain variable region as shown in SEQ ID NO: 66.

In an exemplary embodiment, the antibody or antigen-binding fragment thereof comprises:

(a) a heavy chain variable region (VH) comprising an amino acid sequence selected from the group consisting of:

(i) the sequence as shown in SEQ ID NO: 65;

(ii) a sequence having a substitution, deletion or addition of one or several amino acids (e.g., a substitution, deletion or addition of 1, 2, 3, 4, or 5 amino acids) compared to the sequence as shown in SEQ ID NO: 65; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 65;

and/or, (b) a light chain variable region (VL) comprising an amino acid sequence selected from the group consisting of:

(iv) the sequence as shown in SEQ ID NO: 66;

(v) a sequence having a substitution, deletion or addition of one or several amino acids (e.g., a substitution, deletion or addition of 1, 2, 3, 4, or 5 amino acids) compared to the sequence as shown in SEQ ID NO: 66; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% to the sequence as shown in SEQ ID NO: 66.

In certain preferred embodiments, the substitution as recited in (ii) or (v) is a conservative substitution.

In certain preferred embodiments, the antibody or antigen-binding fragment thereof comprises: a VH having a sequence as shown in SEQ ID NO: 65, and a VL having a sequence as shown in SEQ ID NO: 66.

In certain preferred embodiments, the antibody or antigen-binding fragment thereof is humanized.

In certain preferred embodiments, the VH of the antibody or antigen-binding fragment thereof comprises a heavy chain variable region (VH) framework region (FR) derived from a human immunoglobulin, and/or the VL of the antibody or antigen-binding fragment thereof comprises a light chain variable region (VL) framework region (FR) derived from a human immunoglobulin.

In such embodiments, the heavy chain variable region FR and/or light chain variable region FR of the antibody or antigen-binding fragment thereof may comprise one or more non-human (e.g., murine) amino acid residues, for example, the heavy chain framework region FR and/or light chain framework region FR may comprise one or more amino acid back mutations, and the corresponding murine amino acid residues are contained in these back mutations.

In certain preferred embodiments, the antibody or antigen-binding fragment thereof of the present invention may further comprise a constant region sequence or variant thereof derived from a mammalian (e.g., murine or human) immunoglobulin, in which the variant has a substitution, deletion or addition of one or more amino acids compared to the sequence from which it is derived. In certain preferred embodiments, the variant has a conservative substitution of one or more amino acids compared to the sequence from which it is derived.

In certain preferred embodiments, the heavy chain of the antibody or antigen-binding fragment thereof of the present invention comprises a heavy chain constant region (CH) of a human immunoglobulin or a variant thereof, in which the variant has a substitution, deletion or addition of one or more amino acids (e.g., a substitution, deletion or addition of up to 20, up to 15, up to 10, or up to 5 amino acids; for example, a substitution, deletion or addition of 1, 2, 3, 4 or 5 amino acids); and/or, The light chain of the antibody or antigen-binding fragment thereof of the present invention comprises a light chain constant region (CL) of a human immunoglobulin or a variant thereof, in which the variant has a substitution, deletion or addition of up to 20 amino acids (e.g., a substitution, deletion or addition of up to 15, up to 10, or up to 5 amino acids; for example, a substitution, deletion or addition of 1, 2, 3, 4 or 5 amino acids).

In certain preferred embodiments, the heavy chain constant region is an IgG heavy chain constant region, such as an IgG1, IgG2, IgG3 or IgG4 heavy chain constant region. In certain preferred embodiments, the heavy chain constant region is a murine IgG1, IgG2, IgG3 or IgG4 heavy chain constant region. In certain preferred embodiments, the heavy chain constant region is a human IgG1, IgG2, IgG3 or IgG4 heavy chain constant region. In certain embodiments, the heavy chain constant region is preferably a human IgG1 or IgG4 heavy chain constant region.

In certain preferred embodiments, the light chain constant region is a κ light chain constant region. In certain preferred embodiments, the light chain constant region is a murine κ light chain constant region. In certain preferred embodiments, the light chain constant region is a human κ light chain constant region.

In certain exemplary embodiments, the antibody or antigen-binding fragment thereof of the present invention comprises a heavy chain constant region (CH) as shown in SEQ ID NO: 81; and/or, a light chain constant region (CL) as shown in SEQ ID NO: 82.

In certain preferred embodiments, the antibody of the present invention is a murine antibody, a chimeric antibody, a humanized antibody, a bispecific antibody or a multispecific antibody. In certain preferred embodiments, the antigen-binding fragment of the present invention is selected from the group consisting of Fab, Fab', (Fab')$_2$, Fv, disulfide-linked Fv, scFv, diabody, and single domain antibody (sdAb).

In the present invention, the antibody or antigen-binding fragment thereof of the present invention may include a variant that differs from the antibody or antigen-binding fragment thereof from which it is derived only by a conservative substitution of one or more amino acid residues (e.g., a conservative substitution of up to 20, up to 15, up to 10, or up to 5 amino acids), or has a sequence identity of at least 85%, at least 90%, at least 95%, at least 96%, at least 97%, at least 98%, at least 99%, or 100% to the antibody or antigen-binding fragment thereof from which it is derived, and substantially retains the biological function of the antibody or antigen-binding fragment thereof from which it is derived.

Preparation of Antibodies

The antibody of the present invention can be prepared by a variety of methods known in the art, for example, by genetic engineering recombinant techniques. For example, a DNA molecule encoding the heavy chain and light chain genes of the antibody of the present invention is obtained by chemical synthesis or PCR amplification. The resulting DNA molecule is inserted into an expression vector and then transfected into a host cell. Then, the transfected host cell is cultured under specific conditions to express the antibody of the present invention.

The antigen-binding fragment of the present invention can be obtained by hydrolyzing an intact antibody molecule (see: Morimoto et al., J. Biochem. Biophys. Methods 24: 107-117 (1992); and Brennan et al., Science 229: 81 (1985)). Alternatively, these antigen-binding fragments can also be produced directly by recombinant host cells (reviewed in Hudson, Curr. Opin. Immunol. 11: 548-557 (1999); Little et al., Immunol. Today, 21: 364-370 (2000)). For example, Fab' fragments can be obtained directly from host cells; Fab' fragments can be chemically coupled to form F(ab')$_2$ fragments (Carter et al., Bio/Technology, 10: 163-167 (1992)). In addition, Fv, Fab or F(ab')$_2$ fragments can also be directly isolated from the culture medium of the recombinant host cells. Those of ordinary skill in the art are fully aware of other techniques for preparing these antigen-binding fragments.

Therefore, in another aspect, the present invention provides an isolated nucleic acid molecule comprising a nucleotide sequence encoding the antibody or antigen-binding fragment thereof of the present invention, or a heavy chain variable region and/or light chain variable region thereof.

In certain preferred embodiments, the isolated nucleic acid molecule encodes the antibody or antigen-binding fragment thereof of the present invention, or a heavy chain variable region and/or light chain variable region thereof.

In another aspect, the present invention provides a vector (e.g., a cloning vector or an expression vector) comprising an isolated nucleic acid molecule of the present invention. In certain preferred embodiments, the vector of the present invention is, for example, a plasmid, a cosmid, a phage, and the like. In certain preferred embodiments, the vector is capable of expressing the antibody or antigen-binding fragment thereof of the present invention in a subject (e.g., a mammal, such as a human).

In another aspect, the present invention provides a host cell comprising an isolated nucleic acid molecule of the present invention or a vector of the present invention. Such host cell includes, but is not limited to, prokaryotic cell such as *E. coli* cell, and eukaryotic cell such as yeast cell, insect cell, plant cell, and animal cell (e.g., mammalian cell, such as mouse cell, human cell, etc.).

In certain preferred embodiments, the host cell of the present invention is a mammalian cell, such as a CHO (e.g., CHO-K1, CHO-S, CHO DG44).

In another aspect, there is provided a method of preparing the antibody or antigen-binding fragment thereof of the present invention, comprising culturing a host cell of the present invention under a condition allowing the expression of the antibody or antigen-binding fragment thereof, and recovering the antibody or antigen-binding fragment thereof from the cultured host cell culture.

Derived Antibodies

The antibody or antigen-binding fragment thereof of the present invention can be derivatized, for example, linked to another molecule (e.g., another polypeptide or protein). In general, the derivatization (e.g., labeling) of the antibody or antigen-binding fragment thereof does not adversely affect its binding to CLDN18.2 (especially, human CLDN18.2). Therefore, the antibody or antigen-binding fragment thereof of the present invention is also intended to include such derivatization forms. For example, the antibody or antigen-binding fragment thereof of the present invention can be functionally linked (by chemical coupling, gene fusion, non-covalent linkage, or other means) to one or more other molecular groups, such as another antibody (e.g., to form a bispecific antibody), a detection reagent, a pharmaceutical reagent, and/or a protein or polypeptide (e.g., avidin or polyhistidine tag) capable of mediating the binding of the antibody or antigen-binding fragment thereof to another molecule. In addition, the antibody or antigen-binding fragment thereof of the present invention can also be derivatized with a chemical group, such as polyethylene glycol (PEG), methyl or ethyl, or glycosyl. These groups can be used to improve the biological properties of the antibody, such as increasing serum half-life.

Therefore, in certain preferred embodiments, the antibody or antigen-binding fragment thereof of the present invention is labeled. In certain preferred embodiments, the antibody or antigen-binding fragment thereof of the present invention bears a detectable label, such as an enzyme, a radionuclide, a fluorescent dye, a luminescent substance (e.g., a chemiluminescent substance), or a biotin. The detectable label according to the present invention may be any substance that can be detected by fluorescent, spectroscopic, photochemical, biochemical, immunological, electrical, optical, or chemical means. Such labels are well known in the art, and examples thereof include, but are not limited to, enzymes (e.g., horseradish peroxidase, alkaline phosphatase, 0-galactosidase, urease, glucose oxidase, etc.), radionuclides (e.g., $^{3}H$, $^{125}J$, $^{35}S$, $^{14}C$, or $^{32}P$), fluorescent dyes (e.g., fluorescein isothiocyanate (FITC), fluorescein, tetramethylrhodamine isothiocyanate (TRITC), phycoerythrin (PE), Texas Red, Rhodamine, quantum dots, or cyanine dye derivatives (e.g. Cy7, Alexa 750), luminescent materials (e.g. chemiluminescent materials such as acridine esters), magnetic beads (e.g., Dynabeads®), calorimetric labels such as colloidal gold or colored glass or plastic beads (e.g., polystyrene, polypropylene, latex, etc.), and biotins to bind an avidin (e.g., streptavidin) modified by the above labels. The patents that teach the use of these labels include, but are not limited to, U.S. Pat. Nos. 3,817,837; 3,850,752; 3,939,350; 3,996,345; 4,277,437; 4,275,149; and 4,366,241 (all incorporated herein by reference). The detectable labels as described above can be detected by methods known in the art. For example, the radioactive labels can be detected using photographic film or a scintillation counter, and the fluorescent labels can be detected using a photodetector to detect the emitted light. The enzyme label is generally detected by providing a substrate to the enzyme and detecting a reaction product produced by the effect of the enzyme on the substrate. And the calorimetric labels are detected by simply visualizing the colored labels. In certain embodiments, such labels can be suitable for immunological detection (e.g., enzyme-linked immunoassay, radioimmunoassay, fluorescent immunoassay, chemiluminescence immunoassay, etc.). In certain embodiments, the detectable label as described above can be linked to the antibody or antigen-binding fragment thereof of the present invention via linkers of different lengths to reduce potential steric hindrance.

Bispecific or Multispecific Molecules

The antibody or antigen-binding fragment thereof of the present invention can be used to form bispecific or multispecific molecules. The antibody or antigen-binding fragment thereof of the present invention may be a part of a bispecific or multispecific molecule, and the bispecific or multispecific molecule comprises a second functional module (e.g., a second antibody) having a binding specificity different from that of the antibody or antigen-binding fragment thereof of the present invention, so that it is capable of binding to at least two different binding sites and/or target molecules. For example, the antibody or antigen-binding fragment thereof of the present invention can be linked to a second antibody or antigen-binding fragment thereof that is capable of specifically binding to any protein that can be used as a potential target for combination therapy. To generate the bispecific or multispecific molecule, the antibody or antigen-binding fragment thereof of the present invention can be linked (e.g., by chemical coupling, gene fusion, non-covalent association or other means) to one or more other binding molecules (e.g., additional antibodies, antibody fragments, peptides, or binding mimics).

Therefore, in another aspect, the present invention provides a bispecific or multispecific molecule comprising the antibody or antigen-binding fragment thereof of the present invention.

In certain preferred embodiments, the bispecific or multispecific molecule specifically binds to CLDN18.2 and additionally specifically binds to one or more other targets.

In certain preferred embodiments, the bispecific or multispecific molecule further comprises at least one molecule (e.g., a second antibody) having a second binding specificity for a second target.

Immunoconjugates

The antibody or antigen-binding fragment thereof of the present invention can be linked to a therapeutic agent to form an immunoconjugate. Because these immunoconjugates have the ability to selectively deliver one or more therapeutic agents to target tissues (e.g., tumor-associated antigens, such as tumors expressing CLDN18.2), the immunoconjugates can enhance the therapeutic efficacy of the antibody or antigen-binding fragment thereof of the present invention in the treatment of diseases (e.g., cancers).

Therefore, in another aspect, the present invention provides an immunoconjugate comprising the antibody or antigen-binding fragment thereof of the present invention and a therapeutic agent linked to the antibody or antigen-binding fragment thereof.

In certain preferred embodiments, the immunoconjugate is an antibody-drug conjugate (ADC).

In certain preferred embodiments, the therapeutic agent is a cytotoxic agent. In the present invention, the cytotoxic agent includes any agent that is harmful to a cell (e.g., killing cell).

In certain preferred embodiments, the therapeutic agent is selected from the group consisting of alkylating agents, anti-mitotic agents, antitumor antibiotics, antimetabolites, topoisomerase inhibitors, tyrosine kinase inhibitors, radionuclide agents, and any combinations thereof.

Examples of alkylating agents that can be used in the immunoconjugates of the present invention include, but are not limited to, nitrogen mustards (e.g., dichloroethylmethylamine, phenylbutyric acid mustard, melphalan, cyclophosphamide, etc.), ethyleneimines (e.g., thiotepae etc.), sulfonates and polyols (e.g., busulfan, dibromomannitol), nitrosoureas (e.g., carmustine, lomustine, etc.), platinum-based antitumor agents (e.g., rdscisplatin, oxaliplatin, carboplatin, etc.).

Examples of anti-mitotic agents that can be used in the immunoconjugates of the present invention include, but are not limited to, maytansinoids (e.g., maytansine, maytansinol, C-3 esters of maytansinol, etc.), taxanes (e.g., docetaxel, paclitaxel or nanoparticle paclitaxel, etc.), vinca rosea alkaloids (e.g., vinblastine sulfate, vincristine, vinblastine, or vinorelbine, etc.) Examples of antitumor antibiotics that can be used in the immunoconjugates of the present invention include, but are not limited to, actinomycin, anthracycline antibiotics (e.g., daunorubicin, doxorubicin, epirubicin, idarubicin, etc.), calicheamicin, duocarmycin, etc.

Examples of antimetabolites that can be used in the immunoconjugates of the present invention include, but are not limited to, folate antagonists (e.g., methotrexate, etc.), pyrimidine antagonists (e.g., 5-fluorouracil, fluorouridine, cytarabine, capecitabine, gemcitabine, etc.), purine antagonists (e.g., 6-mercaptopurine, 6-thioguanine, etc.), adenosine deaminase inhibitors (e.g., cladribine, fludarabine, nelarabine, pentostatin, etc.).

Examples of topoisomerase inhibitors that can be used in the immunoconjugates of the present invention include, but are not limited to, camptothecins and derivatives thereof (e.g., irinotecan, topotecan, etc.), amsacrine, daunomycin, adriamycin, epipodophyllotoxin, ellipticine, epirubicin, etoposide, razoxane, teniposide, etc.

Examples of tyrosine kinase inhibitors that can be used in the immunoconjugates of the present invention include, but are not limited to, axitinib, bosutinib, sildenib, dasatinib, erlotinib, gefitinib, imatinib, lapatinib, lestaurtinib, nilotinib, semaxanib, sunitinib, vandetanib, etc.

Examples of radionuclide agents that can be used in the immunoconjugate of the present invention include, but are not limited to, $^{131}$, $In^{111}$, $Y^{90}$, $Lu^{177}$, and the like.

In certain exemplary embodiments, the therapeutic agent is selected from the group consisting of platinum-based antitumor agents, anthracycline antibiotics, taxanes, nucleoside analogs, camptothecin compounds, and analogues or homologues thereof, as well as any combinations thereof.

In certain preferred embodiments, the antibody or antigen-binding fragment thereof of the present invention is optionally conjugated to the therapeutic agent via a linker.

In the present invention, the cytotoxic agent can be coupled to the antibody or antigen-binding fragment thereof of the present invention using a linker technology available in the art. Examples of linker types that have been used to couple a cytotoxic agent to an antibody include, but are not limited to, hydrazones, thioethers, esters, disulfides, and peptide-containing linkers. A linker can be selected, for example, that is susceptible to cleavage by low pH within the lysosomal compartment or susceptible to cleavage by proteases, such as proteases preferentially expressed in tumor tissue such as cathepsins (e.g., cathepsins B, C, D)..

For further discussion on the types of cytotoxic agents, linkers, and methods of coupling therapeutic agents to antibodies, see also Saito, G. et al. (2003) Adv. Drug Deliv. Rev. 55: 199-215; Trail, P A et al. (2003) Cancer Immunol. Immunother. 52: 328-337; Payne, G. (2003) Cancer Cell 3: 207-212; Allen, TM (2002) Nat. Rev. Cancer 2: 750-763; Pastan, I. and Kreitman, RJ (2002) Curr. Opin. Investig. Drugs 3: 1089-1091; Senter, P D and Springer, CJ (2001) Adv. Drug Deliv. Rev. 53: 247-264.

Chimeric Antigen Receptor

The antibody or antigen-binding fragment thereof of the present invention can be used to construct a chimeric antigen receptor (CAR), the chimeric antigen receptor comprises an extracellular antigen-binding domain (e.g., scFv) that specifically binds to CLDN18.2, and is linked to a transmembrane domain and one or more intracellular T cell signaling domains. The intracellular T cell signaling domains may include, for example, T cell receptor signaling domains, T cell costimulatory signaling domains, or combinations thereof. The T cell receptor signaling domain refers to a part of CAR that contains the intracellular domain of T cell receptor (e.g., an intracellular part of CD3ζ protein). The costimulatory signaling domain refers to a part of CAR that contains the intracellular domain of a costimulatory molecule, and the costimulatory molecule is a cell surface molecule other than the antigen receptors or ligands thereof that are required for efficient response of lymphocytes against the antigen.

The characteristics of the CAR of the present invention include its ability to redirect T-cell specificity and reactivity toward a cell expressing CLDN18.2 (e.g., a tumor cell) in a non-MHC-restricted manner. The non-MHC-restricted recognition of CLDN18.2 gives T cells expressing the CAR of the present invention the ability to recognize an antigen independent of antigen processing.

Therefore, in another aspect, the present invention provides a chimeric antigen receptor (CAR) comprising an antigen-binding domain of the antibody or antigen-binding fragment thereof of the present invention.

In certain preferred embodiments, the antigen-binding domain comprises a heavy chain variable region and a light chain variable region of the antibody or antigen-binding fragment thereof of the present invention.

In certain preferred embodiments, the antigen-binding domain is a scFv.

In certain preferred embodiments, the chimeric antigen receptor comprises an antigen-binding fragment (e.g., a scFv) of the antibody of the present invention.

In certain preferred embodiments, the chimeric antigen receptor is expressed by an immune effector cell (e.g., a T cell).

In certain preferred embodiments, there may be a spacer domain comprising a polypeptide sequence between the antigen-binding domain and the transmembrane domain of the CAR. The spacer domain may comprise up to 300 amino acids, preferably 10 to 100 amino acids, and most preferably 25 to 50 amino acids. In some embodiments, the spacer domain may comprise an immunoglobulin domain, such as a human immunoglobulin sequence. In certain exemplary embodiments, the immunoglobulin domain comprises immunoglobulin CH2 and CH3 domain sequences. In such embodiments, without being bound by a particular theory, it is believed that the CH2 and CH3 domains moves the antigen-binding domain of CAR away from the membrane of the CAR-expressing cell, and can more accurately mimic the size and domain structure of a natural TCR.

In certain preferred embodiments, the transmembrane domain may be derived from a natural or synthetic source. In such embodiments, the domain may be derived from any membrane-bound or transmembrane protein. Exemplary transmembrane domains that can be used in the CAR of the present invention may comprise at least the transmembrane region of a, R or (chain of T cell receptor, and the T cell receptor may be selected from the group consisting of CD28, CD3F, CD45, CD4, CD5, CDS, CD9, CD16, CD22, CD33, CD37, CD64, CD80, CD86, CD134, CD137, CD154. Alternatively, the transmembrane domain may be synthetic, in which case it will mainly contain hydrophobic residues such as leucine and valine.

In certain exemplary embodiments, the transmembrane domain comprises a transmembrane domain of T cell receptor, such as a CD8 transmembrane domain.

In certain exemplary embodiments, the transmembrane domain comprises a transmembrane domain of T-cell costimulatory molecule (e.g., CD137 or CD28).

In certain preferred embodiments, examples of intracellular T cell domain that can be used in the CAR include cytoplasmic sequences of T cell receptor (TCR) and costimulatory molecules that act in concert to initiate signal transduction following antigen receptor engagement, and any derivatives or variants of these sequences and any synthetic sequences with the same functional capacity.

In certain preferred embodiments, the intracellular region of the CAR may comprise a primary cytoplasmic signaling sequence that acts in a stimulatory manner, which may comprise a signaling motif which is known as immunoreceptor tyrosine-based activation motif or ITAM. Examples of ITAM containing primary cytoplasmic signaling sequences that can be comprised in the CAR include those derived from CD3ζ, FcRγ, FcRβ, CD3γ, CD3δ, CD3ε, CDS, CD22, CD79a, CD79b, and CD66d proteins.

In certain preferred embodiments, the intracellular region of the CAR may comprise an ITAM containing a primary cytoplasmic signaling domain (e.g., CD3ζ) alone or in combination with any other desired cytoplasmic domain that can be used in CAR. For example, the cytoplasmic domain of the CAR comprises a portion of CD3ζ chain and an intracellular costimulatory signaling domain. The costimulatory signaling domain refers to the portion of the CAR that contains the intracellular domain of a costimulatory molecule. Costimulatory molecule is a cell surface molecule other than antigen receptors or ligands thereof required for efficient response of lymphocyte against the antigen. Examples of such molecule include CD27, CD28, 4-1BB (CD137), OX40 (CD134), CD30, CD40, PD-1, ICOS, lymphocyte function-associated antigen 1 (LFA-1), CD2, CD7, LIGHT, NKG2C and B7-H3.

In certain preferred embodiments, the CAR may comprise a CD3ζ signaling domain, a CD8 signaling domain, a CD28 signaling domain, a CD137 signaling domain, or any combination thereof. The order of the one or more T cell signal domains on the CAR can be changed by those skilled in the art as needed.

Methods for generating the chimeric antigen receptor, and T cell containing such receptor, and uses thereof (e.g., uses for treatment of a cancer) are known in the art, and detailed descriptions thereof can be found in, for example, Brentjens et al., 2010, Molecular Therapy, 18: 4,666-668; Morgan et al., 2010, Molecular Therapy, published online Feb. 23, 2010, pages 1-9; Till et al., 2008, Blood, 112: 2261-2271; Park et al., Trends Biotechnol., 29: 550-557, 2011; Grupp et al., NEnglJMed., 368: 1509-1518, 2013; Han et al., J. Hematol Oncol., 6:47, 2013; PCT Patent Publication WO2012/079000, WO2013/126726; and US Patent Publication 2012/0213783, all of which are incorporated herein by reference in their entirety. For example, a nucleic acid molecule encoding the chimeric antigen-binding receptor of the present invention can be contained in an expression vector (e.g., a lentiviral vector) for expression in a host cell, such as a T cell, to make the CAR. In certain exemplary embodiments, a method of using the chimeric antigen receptor comprises isolating a T cell from a subject, transforming the T cell with an expression vector (e.g., a lentiviral vector) encoding the chimeric antigen receptor, and administrating the engineered T cell expressing the chimeric antigen receptor to the subject to perform treatment, for example, treatment of a tumor in the subject.

Thus, in another aspect, the present invention provides an isolated nucleic acid molecule comprising a nucleotide sequence encoding the chimeric antigen receptor of the present invention. In certain preferred embodiments, the isolated nucleic acid molecule encodes the chimeric antigen receptor of the present invention.

In another aspect, the present invention provides a vector (e.g., a cloning vector or an expression vector) comprising the isolated nucleic acid molecule as described above. In certain preferred embodiments, the vector of the present invention is, for example, a plasmid.

In another aspect, the present invention provides a host cell comprising the isolated nucleic acid molecule or vector as described above. In certain preferred embodiments, the host cell is a T cell. In certain preferred embodiments, the host cell is a chimeric antigen receptor T cell (CAR-T). Treatment Method and Pharmaceutical Composition The antibody or antigen-binding fragment thereof of the present invention can induce ADCC and/or CDC via binding to CLDN18.2, and thus can be used for preventing and/or treating a tumor.

Therefore, in another aspect, the present invention provides a pharmaceutical composition comprising the antibody or antigen-binding fragment thereof, bispecific or multispecific molecule, or immunoconjugate of the present invention, and a pharmaceutically acceptable carrier and/or excipient.

In certain preferred embodiments, the pharmaceutical composition may further comprise an additional pharmaceutically active agent.

In certain preferred embodiments, the additional pharmaceutically active agent is an antitumor agent, such as an alkylating agent, an anti-mitotic agent, an antitumor antibiotic, an antimetabolite, a topoisomerase inhibitor, a tyrosine kinase inhibitor, a radionuclide, a radiosensitizer (e.g., gemcitabine, 5-fluorouracil, taxane, cisplatin, etc.), an anti-angiogenic agent, a cytokine (e.g, GM-CSF, IL-7, IL-12, IL-15, IL-18, IL-21, etc.), a molecular-targeted agent (e.g., CD20 antibody such as rituximab, Her2 antibody such as trastuzumab, VEGF antibody such as bevacizumab, EGFR antibody such as cetuximab, etc.), an immune checkpoint inhibitor (e.g., PD-1 antibody, PD-L1 antibody, CTLA-4 antibody, LAG-3 antibody, etc.), an oncolytic virus, and the like.

In certain preferred embodiments, in the pharmaceutical composition, the antibody or antigen-binding fragment thereof, bispecific or multispecific molecule, or immunoconjugate of the present invention and the additional pharmaceutically active agent are provided as separate components or as components of a single composition. Thus, the antibody or antigen-binding fragment thereof, bispecific or multispecific molecule, or immunoconjugate of the present invention and the additional pharmaceutically active agent can be administered simultaneously, separately, or sequentially.

In certain exemplary embodiments, the pharmaceutical composition comprises a sterile injectable liquid (e.g., an aqueous or non-aqueous suspension or solution). In certain exemplary embodiments, such sterile injectable liquid is selected from the group consisting of water for injection (WFI), bacteriostatic water for injection (BWFI), sodium chloride solution (e.g., 0.9% (w/v) NaCl), glucose solution (e.g., 5% glucose), a surfactant-containing solution (e.g., 0.01% polysorbate 20), a pH buffer solution (e.g., a phosphate buffer solution), a Ringer's solution, and any combination thereof.

In another aspect, the present invention provides a method for reducing the expression level of CLDN18.2 on the surface of a cell, which comprises contacting the cell with the antibody or antigen-binding fragment thereof, bispecific or multispecific molecule, immunoconjugate or pharmaceutical composition of the present invention so as to reduce the expression level of CLDN18.2 on the cell surface; wherein the cell has CLDN18.2 expressed on the surface thereof.

In certain preferred embodiments, the cell is a tumor cell expressing CLDN18.2.

In certain preferred embodiments, the method is used to reduce the expression level of CLDN18.2 on a cell surface in vitro for a non-diagnostic purpose.

In another aspect, there is provided use of the antibody or antigen-binding fragment thereof, bispecific or multispecific molecule, immunoconjugate, or pharmaceutical composition of the present invention in the manufacture of a medicament for reducing the expression level of CLDN18.2 on a cell surface.

In another aspect, the antibody or antigen-binding fragment, bispecific or multispecific molecule, immunoconjugate, or pharmaceutical composition of the present invention is provided for reducing the expression level of CLDN18.2 on a cell surface.

In another aspect, the present invention provides a method for inhibiting growth and/or killing of a tumor cell expressing CLDN 18.2, which comprises contacting the tumor cell with an effective amount of the antibody or antigen-binding fragment thereof, bispecific or multispecific molecule, immunoconjugate, pharmaceutical composition, chimeric antigen receptor, or host cell expressing the chimeric antigen receptor (e.g., chimeric antigen receptor T cell (CAR-T)) of the present invention.

The method can be used for a therapeutic purpose, or for a non-therapeutic purpose. In certain preferred embodiments, the method may be used for a non-therapeutic purpose, and the method is used to inhibit growth and/or kill of a tumor cell expressing CLDN 18.2 in vitro.

In another aspect, there is provided use of the antibody or antigen-binding fragment thereof, bispecific or multispecific molecule, immunoconjugate, pharmaceutical composition, chimeric antigen receptor or host cell expressing the chimeric antigen receptor (e.g., chimeric antigen receptor T cell (CAR-T)) of the present invention in the manufacture of a medicament for inhibiting growth and/or killing of a tumor cell expressing CLDN 18.2.

In another aspect, the antibody or antigen-binding fragment thereof, bispecific or multispecific molecule, immunoconjugate, pharmaceutical composition, chimeric antigen receptor or host cell expressing the chimeric antigen receptor (e.g., chimeric antigen receptor T cell (CAR-T)) is provided for inhibiting growth and/or killing of a tumor cell expressing CLDN 18.2.

In another aspect, the present invention provides a method for preventing and/or treating a tumor in a subject (e.g., a human), comprising administering to the subject in need thereof an effective amount of the antibody or antigen-binding fragment thereof, bispecific or multispecific molecule, immunoconjugate, pharmaceutical composition, chimeric antigen receptor, or host cell expressing the chimeric antigen receptor (e.g., chimeric antigen receptor T cell (CAR-T)).

In certain preferred embodiments, the tumor involves a tumor cell expressing CLDN18.2. In certain preferred embodiments, the CLDN18.2 is expressed on the surface of the tumor cell.

In certain preferred embodiments, the tumor expresses CLDN18.2.

In certain preferred embodiments, the tumor is selected from the group consisting of gastric cancer, esophageal cancer, pancreatic cancer, bronchial cancer, non-small cell lung cancer, breast cancer, ear-nose-throat (ENT) cancer, ovarian cancer, colon cancer, liver cancer, head and neck cancer, gallbladder cancer, and metastatic cancers thereof (e.g., gastric cancer metastasis, such as Krukenberg tumor, peritoneal metastasis, or lymph node metastasis).

In certain preferred embodiments, the antibody or antigen-binding fragment thereof, bispecific or multispecific molecule, immunoconjugate, pharmaceutical composition, chimeric antigen receptor, or host cell expressing the chimeric antigen receptor (e.g., chimeric antigen receptor T cell (CAR-T)) of the present invention is used in combination with an additional antitumor agent. Such additional antitumor agent can be administered before, at the same time or after the antibody or antigen-binding fragment thereof, bispecific or multispecific molecule, immunoconjugate, pharmaceutical composition, chimeric antigen receptor or host cell expressing the chimeric antigen receptor (e.g., CAR-T) of the present invention is administered.

In certain preferred embodiments, the antibody or antigen-binding fragment thereof, bispecific or multispecific molecule, immunoconjugate, pharmaceutical composition, chimeric antigen receptor, or host cell expressing the chimeric antigen receptor (e.g., CAR-T) of the present invention is administered in combination with an additional therapy. Such additional therapy may be any therapy known for tumors, such as surgery, chemotherapy, radiation therapy, targeted therapy, immunotherapy, hormone therapy, gene therapy, or palliative care. Such additional therapy can be performed before, at the same time or after the antibody or antigen-binding fragment thereof, bispecific or multispecific molecule, immunoconjugate, pharmaceutical composition, chimeric antigen receptor or host cell expressing the chimeric antigen receptor (e.g., CAR-T) of the present invention is administered.

The antibody or antigen-binding fragment thereof, bispecific or multispecific molecule, immunoconjugate, pharmaceutical composition, chimeric antigen receptor or host cell expressing the chimeric antigen receptor (e.g., CAR-T) of the present invention can be formulated into any dosage form known in the medical field, for example, tablets, pills, suspensions, emulsions, solutions, gels, capsules, powders, granules, elixirs, lozenges, suppositories, injections (including injection liquids, sterile powders for injection and concentrated solutions for injection), inhalants, sprays, etc. The preferred dosage form depends on the intended route of administration and therapeutic use. The pharmaceutical composition of the present invention should be sterile and stable under the conditions of manufacture and storage. One preferred dosage form is an injection. Such injection may be a sterile injectable solution. For example, the sterile injectable solution can be prepared by the following method: incorporating a necessary amount of the antibody of the present invention in an appropriate solvent, and optionally, simultaneously incorporating other desired ingredients (including, but not limited to, pH adjusting agent, surfactant, adjuvant, ionic strength enhancer, isotonic agent, preservative, diluent, or any combination thereof), and then performing filtered sterilization. In addition, the sterile injectable solution can be prepared as a sterile lyophilized powder (e.g., by vacuum drying or freeze drying) for the convenience of storage and use. Such sterile lyophilized powder can be dispersed before use in a suitable carrier, such as water for injection (WFI), bacteriostatic water for injection (BWFI), sodium chloride solution (e.g., 0.9% (w/v) NaCl), glucose solution (e.g., 5% glucose), surfactant-containing solution (e.g., 0.01% polysorbate 20), pH buffered solution (e.g., phosphate buffered solution), Ringer's solution, and any combination thereof.

In addition, the antibody or antigen-binding fragment thereof, bispecific or multispecific molecule, immunoconjugate, pharmaceutical composition, chimeric antigen receptor or host cell expressing the chimeric antigen receptor (e.g., T Cell) of the present invention can be present in unit dosage form in a pharmaceutical composition for the convenience of administration.

The antibody or antigen-binding fragment thereof, bispecific or multispecific molecule, immunoconjugate, pharmaceutical composition, chimeric antigen receptor or host cell expressing the chimeric antigen receptor (e.g., T Cell) of the present invention can be administrated by any suitable method known in the art, including, but not limited to, oral, buccal, sublingual, eyeball, topical, parenteral, rectal, intrathecal, intracytoplasmic, groin, intravesical, local (e.g., powder, ointment or drops), or nasal route. However, for many therapeutic uses, the preferred route/mode of administration is parenteral administration (e.g., intravenous injection or bolus, subcutaneous injection, intraperitoneal injection, intramuscular injection). The skilled person will understand that the route and/or mode of administration will vary depending on the intended purpose. In a preferred embodiment, the antibody or antigen-binding fragment thereof, bispecific or multispecific molecule, immunoconjugate, pharmaceutical composition, chimeric antigen receptor or host cell expressing the chimeric antigen receptor (e.g., T Cell) of the present invention is given by intravenous injection or bolus.

The pharmaceutical composition of the present invention may comprise a "therapeutically effective amount" or a "prophylactically effective amount" of the antibody or antigen-binding fragment thereof, bispecific or multispecific molecule, immunoconjugate, pharmaceutical composition, chimeric antigen receptor or host cell expressing the chimeric antigen receptor (e.g., T Cell) of the present invention. The "prophylactically effective amount" refers to an amount sufficient to prevent, stop, or delay the onset of a disease. The "therapeutically effective amount" refers to an amount sufficient to cure or at least partially block a disease and its complications in a patient already suffering from the disease. The therapeutically effective amount of the antibody or antigen-binding fragment thereof of the present invention may vary depending on factors such as the severity of the disease to be treated, the overall state of the patient's immune system, the general condition of the patient such as age, weight and gender, the route of administration, and other therapies applied simultaneously.

In the present invention, the dosing regimen can be adjusted to obtain an optimal response (e.g., a therapeutic or preventive response). For example, a single dose may be given, or multiple doses may be given over a period of time, or the dose may be proportionally reduced or increased as indicated by the exigencies of therapeutic situation.

In the present invention, the subject may be a mammal, such as a human.

Detection Method and Kit

The antibody or antigen-binding fragment thereof of the present invention can specifically bind to CLDN18.2, and thus can be used to detect the presence or level of CLDN18.2 in a sample.

Accordingly, in another aspect, the present invention provides a kit comprising the antibody or antigen-binding fragment thereof of the present invention. In certain preferred embodiments, the antibody or antigen-binding fragment thereof of the present invention is labeled with a detectable label. In a preferred embodiment, the kit further comprises a secondary antibody that specifically recognizes the antibody or antigen-binding fragment thereof of the present invention. Preferably, the second antibody further comprises a detectable label.

In the present invention, the detectable label may be any substance that can be detected by fluorescent, spectroscopic, photochemical, biochemical, immunological, electrical, optical or chemical means. It is particularly preferable that such a label can be suitable for immunological detection (for example, enzyme-linked immunoassay, radioimmunoassay, fluorescent immunoassay, chemiluminescence immunoassay, etc.). Such labels are well known in the art, and include, but are not limited to, enzymes (e.g., horseradish peroxidase, alkaline phosphatase, β-galactosidase, urease, glucose oxidase, etc.), radionuclides (e.g., $^3H$, $^{125}J$, $^{35}S$, $^{14}C$, or 32P) fluorescent dyes (e.g., fluorescein isothiocyanate (FITC), fluorescein, tetramethylrhodamine isothiocyanate (TRITC), phycoerythrin (PE), Texas Red, Rhodamine, quantum dots, or cyanine dye derivatives (e.g. Cy7, Alexa 750), luminescent materials (e.g. chemiluminescent materials such as acridine esters), magnetic beads (e.g., Dynabeads®), calorimetric labels such as colloidal gold or colored glass or plastic beads (e.g., polystyrene, polypropylene, latex, etc.), and biotins to bind an avidin (e.g., streptavidin) modified by the above labels. The patents that teach the use of these labels include, but are not limited to, U.S. Pat. Nos. 3,817,837; 3,850,752; 3,939,350; 3,996,345; 4,277,437; 4,275,149; and 4,366,241 (all incorporated herein by reference). The detectable labels as described above can be detected by methods known in the art. For example, the radioactive labels can be detected using photographic film or a scintillation counter, and the fluorescent labels can be detected using a photodetector to detect the emitted light. The enzyme label is generally detected by providing a substrate to the enzyme and detecting a reaction product produced by the effect of the enzyme on the substrate. And the calorimetric labels are detected by simply visualizing the colored labels. In certain embodiments, the detectable label as described above can be linked to the antibody or antigen-binding fragment thereof of the present invention via linkers of different lengths to reduce potential steric hindrance.

In another aspect, the present invention provides a method for detecting the presence or amount of CLDN18.2 in a sample, comprising the steps of.

(1) contacting the sample with the antibody or antigen-binding fragment thereof of the present invention;

(2) detecting the formation or amount of a complex between the antibody or antigen-binding fragment thereof and CLDN18.2.

The formation of the complex indicates the presence of CLDN18.2 or a cell expressing CLDN18.2.

In certain preferred embodiments, the sample is a cell sample, i.e., a sample comprising a cell (e.g., a tumor cell). In such embodiments, preferably, the complex is formed between the antibody, antigen-binding fragment or conjugate and CLDN18.2 expressed by a cell in the sample.

In a preferred embodiment, the antibody or antigen-binding fragment thereof of the present invention is further labeled with a detectable label. In another preferred embodiment, in step (2), a reagent with a detectable label is used to detect the antibody or antigen-binding fragment thereof of the present invention.

The method may be used for a diagnostic purpose, or for a non-diagnostic purpose (e.g., the sample is a cell sample, rather than a sample from a patient). In certain preferred embodiments, the CLDN18.2 is human CLDN18.2.

In another aspect, there is provided use of the antibody or antigen-binding fragment thereof of the present invention in the manufacture of a kit for detecting the presence or amount of CLDN18.2 in a sample. In certain preferred embodiments, the CLDN18.2 is human CLDN18.2.

In another aspect, the present invention provides a method for determining whether a tumor is treatable by an anti-tumor therapy targeting CLDN18.2, which comprises the following steps:

(1) contacting a sample containing the tumor cell with the antibody or antigen-binding fragment thereof of the present invention;

(2) detecting the formation of a complex between the antibody or antigen-binding fragment thereof and CLDN18.2.

In certain preferred embodiments, the complex is formed between the antibody or antigen-binding fragment thereof and CLDN18.2 expressed by the tumor cell in the sample.

In certain preferred embodiments, the sample is from a subject who has a tumor, is suspected of having a tumor, or is at risk of having a tumor. In certain preferred embodiments, the sample is from a tissue or organ in which the cells do not substantially express CLDN18.2 when the tissue or organ is free of cancer. In certain preferred embodiments, the tissue is selected from the group consisting of gastric tissue, lung tissue, esophageal tissue, pancreatic tissue, or breast tissue, and the tissue optionally has been diagnosed as being affected by cancer, e.g. by visual inspection or culture test of the tissue or organ cells. In certain preferred embodiments, the tissue is a tissue other than gastric tissue. In certain preferred embodiments, the tissue is a lung tissue, esophageal tissue, pancreatic tissue or breast tissue. In such embodiments, it is indicated that the subject is suitable for an antitumor therapy targeting CLDN18.2 when CLDN18.2 or a cell expressing CLDN18.2 is present, and/or when the amount of CLDN18.2 or cells expressing CLDN18.2 increases compared to a reference level (e.g., compared to a patient without a tumor disease).

In a preferred embodiment, the antibody or antigen-binding fragment thereof of the present invention is further labeled with a detectable label. In another preferred embodiment, in step (2), a reagent with a detectable label is used to detect the antibody or antigen-binding fragment thereof of the present invention.

In certain preferred embodiments, the CLDN18.2 is human CLDN18.2.

In certain preferred embodiments, the tumor is selected from the group consisting of gastric cancer, esophageal cancer, pancreatic cancer, bronchial cancer, non-small cell lung cancer, breast cancer, ear-nose-throat (ENT) cancer, ovarian cancer, colon cancer, liver cancer, head and neck cancer, gallbladder cancer and metastatic cancers thereof (e.g., gastric cancer metastasis, such as Krukenberg tumor, peritoneal metastasis, or lymph node metastasis).

In certain preferred embodiments, the tumor is selected from the group consisting of esophageal cancer, pancreatic cancer, bronchial cancer, non-small cell lung cancer, breast cancer, ENT cancer, ovarian cancer, colon cancer, liver cancer, head and neck cancer, gallbladder cancer and metastatic cancers thereof (e.g., gastric cancer metastasis such as Krukenberg tumor, peritoneal metastasis, or lymph node metastasis).

In another aspect, there is provided use of the antibody or antigen-binding fragment thereof of the present invention in the manufacture of a kit for determining whether a tumor is treatable by an antitumor therapy targeting CLDN18.2.

In certain preferred embodiments, the antibody or antigen-binding fragment thereof is labeled with a detectable label.

In certain preferred embodiments, the CLDN18.2 is human CLDN18.2.

In certain preferred embodiments, the tumor is selected from the group consisting of gastric cancer, esophageal cancer, pancreatic cancer, bronchial cancer, non-small cell lung cancer, breast cancer, ear-nose-throat (ENT) cancer, ovarian cancer, colon cancer, liver cancer, head and neck cancer, gallbladder cancer and metastatic cancers thereof (e.g., gastric cancer metastasis such as Krukenberg tumor, peritoneal metastasis, or lymph node metastasis).

In certain preferred embodiments, the tumor is selected from the group consisting of esophageal cancer, pancreatic cancer, bronchial cancer, non-small cell lung cancer, breast cancer, ENT cancer, ovarian cancer, colon cancer, liver cancer, head and neck cancer, gallbladder cancer and metastatic cancers thereof (e.g., gastric cancer metastasis such as Krukenberg tumor, peritoneal metastasis, or lymph node metastasis).

DEFINITION OF TERMS

In the present invention, unless otherwise stated, scientific and technical terms used herein have meanings commonly understood by those skilled in the art. In addition, the laboratory procedures of cell culture, biochemistry, nucleic acid chemistry, and immunology used herein are routine procedures that are widely used in the corresponding fields. Meanwhile, in order to better understand the present invention, definitions and explanations of related terms are provided below.

As used herein, the term "CLDN18 (Claudin 18)" has the meaning commonly understood by those skilled in the art, which belongs to the Claudin family and is a transmembrane protein within the tight junction of epithelium and endothelium, and exists in the form of two splice variants CLDN18.1 and CLDN18.2. The sequences of CLDN18.1 and CLDN18.2 are well known in the art. For details, see the NCBI database accession numbers NP 057453.1 and NP_001002026.1.

As used herein, the term "antibody" refers to an immunoglobulin molecule that typically consists of two pairs of polypeptide chains, and each pair has a light chain (LC) and a heavy chain (HC). Antibody light chains can be classified as κ (kappa) and λ (lambda) light chains. Heavy chains can be classified as μ, δ, γ, α, or ε, and the isotypes of antibody are defined as IgM, IgD, IgG, IgA, and IgE, respectively. Within the light and heavy chains, the variable and constant regions are linked by a "J" region of about 12 or more amino acids, and the heavy chains further contain a "D" region of about 3 or more amino acids. Each heavy chain is composed of a heavy chain variable region (VH) and a heavy chain constant region (CH). The heavy chain constant region consists of three domains (CH1, CH2, and CH3). Each light chain consists of a light chain variable region (VL) and a light chain constant region (CL). The light chain constant region consists of a domain CL. The constant domains do not directly participate in the binding of antibody to antigen, but exhibit a variety of effector functions, such as mediating the binding of immunoglobulin to a host tissue or factor, including various cells of the immune system (e.g., effector cells) and the first component (Clq) of classical complement system. The VH and VL regions can also be subdivided into regions with high denaturation (referred to as complementary determining regions (CDRs)), which are interspersed with interspaced conservative regions called framework regions (FRs). Each of $V_H$ and $V_L$ is composed of 3 CDRs and 4 FRs arranged in the following order: FR1, CDR1, FR2, CDR2, FR3, CDR3 and FR4 from the amino terminal to the carboxy terminal. The variable regions (VH and VL) of each heavy/light chain pair form an antigen-binding site, respectively. The assignment of amino acids in various regions or domains may follow the definitions of Kabat, Sequences of Proteins of Immunological Interest (National Institutes of Health, Bethesda, Md. (1987 and 1991)), or Chothia & Lesk (1987) J. Mol. Biol. 196: 901-917; Chothia et al. (1989) Nature 342: 878-883.

As used herein, the term "complementary determining region" or "CDR" refers to the amino acid residues in variable region of antibody that are responsible for antigen binding. The variable regions of the heavy and light chains each contain 3 CDRs, named CDR1, CDR2 and CDR3. The precise boundaries of these CDRs can be defined according to various numbering systems known in the art, for example, according to the Kabat numbering system (Kabat et al., Sequences of Proteins of Immunological Interest, 5th Ed. Public Health Service, National Institutes of Health, Bethesda, Md., 1991), Chothia numbering system (Chothia & Lesk (1987) J. Mol. Biol. 196: 901-917; Chothia et al. (1989) Nature 342: 878-883) or IMGT numbering system (Lefranc et al., Dev. Comparat. Immunol. 27: 55-77, 2003). For a given antibody, those skilled in the art will readily identify the CDRs defined by each numbering system. And, the correspondence between different numbering systems is well known to those skilled in the art (e.g., see Lefranc et al., Dev. Comparat. Immunol. 27: 55-77, 2003).

In the present invention, the CDRs contained in the antibody or antigen-binding fragment thereof of the present invention can be determined according to various numbering systems known in the art. In certain embodiments, the CDRs contained in the antibody or antigen-binding fragment thereof of the present invention are preferably determined by the Kabat, Chothia or IMGT numbering system. In certain embodiments, the CDRs contained in the antibody or antigen-binding fragment thereof of the present invention are preferably determined by the Kabat numbering system.

As used herein, the term "framework region" or "FR" residue refers to those amino acid residues other than the CDR residues as defined above in the variable regions of antibody.

The term "antibody" is not limited by any particular method for producing antibody. For example, it includes recombinant antibody, monoclonal antibody and polyclonal antibody. The antibody may be an antibody of different isotypes, for example, IgG (e.g., IgG1, IgG2, IgG3 or IgG4 subtypes), IgAQ1, IgA2, IgD, IgE or IgM antibody.

As used herein, the term "antigen-binding fragment" of antibody refers to a polypeptide comprising a fragment of a full-length antibody that retains the ability to specifically bind to the same antigen to which the full-length antibody binds, and/or competes with the full-length antibody to specifically bind to the antigen, which is also referred to as "antigen-binding portion". See generally, Fundamental Immunology, Ch. 7 (Paul, W., ed., 2nd Edition, Raven Press, NY (1989)), which is incorporated herein by reference in its entirety for all purposes. The antigen-binding fragment of antibody may be produced by recombinant DNA technology or by enzymatic or chemical cleavage of the whole antibody. Non-limiting examples of antigen-binding fragment include Fab, Fab', F(ab')$_2$, Fd, Fv, complementary determining region (CDR) fragments, scFv, diabody, single domain antibody, chimeric antibody, linear antibody, nanobody (technology from Domantis), probody, and such polypeptides, which comprises at least a portion of antibody that is sufficient to confer the specific antigen binding ability to the polypeptide. Engineered antibody variants are reviewed in Holliger et al., 2005; Nat Biotechnol, 23: 1126-1136.

As used herein, the term "full-length antibody" refers to an antibody consisting of two "full-length heavy chains" and two "full-length light chains". The "full-length heavy chain" refers to a polypeptide chain consisting of a heavy chain variable region (VH), a heavy chain constant region CH1 domain, a hinge region (HR), a heavy chain constant region CH2 domain and a heavy chain constant region CH3 domain in a direction from the N-terminus to the C-terminus; and, when the full-length antibody is an IgE isotype, the heavy chain constant region CH4 domain is optionally further included. Preferably, the "full-length heavy chain" is a polypeptide chain consisting of VH, CH1, HR, CH2 and CH3 in a direction from the N-terminal to C-terminal. The "full-length light chain" is a polypeptide chain consisting of a light chain variable region (VL) and a light chain constant region (CL) in a direction from the N-terminal to C-terminal. Two pairs of full-length antibody chains are linked together by a disulfide bond between CL and CH1 and a disulfide bond between HRs of two full-length heavy chains. The full-length antibody of the present invention may be from a single species, such as a human; or may be a chimeric or humanized antibody. The full-length antibody of the present invention comprises two antigen-binding sites formed by VH and VL pairs, respectively, and these two antigen-binding sites specifically recognize/bind the same antigen.

As used herein, the term "Fd" refers to an antibody fragment consisting of VH and CH1 domains; the term "dAb fragment" refers to an antibody fragment consisting of VH domain (Ward et al., Nature 341: 544 546 (1989)); the term "Fab fragment" refers to an antibody fragment consisting of VL, VH, CL and CH1 domains; the term "F(ab')$_2$ fragment" refers to an antibody fragment comprising two Fab fragments connected by a disulfide bridge on hinge region; the term "Fab' fragment" refers to a fragment obtained by reducing the disulfide bond connecting the two heavy chain fragments in the F(ab')$_2$ fragment, which consists of one complete light chain and Fd Fragment (composed of VH and CH1 domains) of heavy chain.

As used herein, the term "Fv" refers to an antibody fragment consisting of VL and VH domains of one arm of antibody. Fv fragment is generally considered to be the smallest antibody fragment that can form a complete antigen-binding site. It is generally believed that 6 CDRs confer antigen-binding specificity to an antibody. However, even a variable region (e.g., an Fd fragment containing only 3 antigen-specific CDRs) is able to recognize and bind an antigen, although its affinity may be lower than that of the complete binding site.

As used herein, the term "Fc" refers to an antibody fragment that is formed by linking the second and third constant regions of the first heavy chain of an antibody with the second and third constant regions of the second heavy chain via a disulfide bond. The Fc fragment of antibody has many different functions, but does not participate in antigen binding.

As used herein, the term "scFv" refers to a single polypeptide chain comprising VL and VH domains, wherein the VL and VH are linked by a linker (see, e.g., Bird et al., Science 242: 423-426 (1988); Huston et al., Proc. Natl. Acad. Sci. USA 85: 5879-5883 (1988); and Pluckthun, The Pharmacology of Monoclonal Antibodies, Vol. 113, eds. Roseburg and Moore, Springer-Verlag, New York, pp. 269-315 (1994)). Such scFv molecule may have a general structure of: NH$_2$—VL-linker-VH—COOH or NH$_2$—VH-linker-VL-COOH. A suitable linker of the prior art consists of a repeating GGGGS amino acid sequence or a variant thereof. For example, a linker having an amino acid sequence (GGGGS)$_4$ may be used, but a variant thereof may also be used (Holliger et al. (1993), Proc. Natl. Acad. Sci. USA 90: 6444-6448). Other linkers useful in the present invention are described by Alfthan et al. (1995), Protein Eng. 8: 725-731, Choi et al. (2001), Eur. J. Immunol. 31: 94-106, Hu et al. (1996), Cancer Res. 56: 3055-3061, Kipriyanov et al. (1999), J. Mol. Biol. 293: 41-56 and Roovers et al.

(2001), Cancer Immunol. In some cases, a disulfide bond may also exist between the VH and VL of scFv.

As used herein, the term "diabody" refers to a fragment in which the VH and VL domains thereof are expressed on a single polypeptide chain, but the used linker is too short to allow pairing between the two domains of the same chain, thereby forcing the domain to pair with the complementary domain of another chain and generating two antigen-binding sites (see, for example, Holliger P. et al., Proc. Natl. Acad. Sci. USA 90: 6444-6448 (1993), and Poljak R J et al., Structure 2: 1121-1123 (1994)).

As used herein, the term "single-domain antibody (sdAb)" has the meaning commonly understood by those skilled in the art, and refers to an antibody fragment consisting of a single monomer variable antibody domain (e.g., a single heavy chain variable region), which retains the ability of specifically binding to the same antigen to which the full-length antibody binds. Single-domain antibody is also known as nanobody.

As used herein, the term "probody" has the meaning commonly understood by those skilled in the art, and refers to a masked antibody that remains inert in a healthy tissue but can be specifically activated in a disease environment (e.g., proteolytic cleavage by a protease that is enriched or specifically present in the disease environment). For detailed teaching, see, for example, Desnoyers et al., Sci. Transl. Med., 5: 207ra144, 2013. Similar masking techniques can be used on any of the antibodies or antigen-binding portions thereof described herein.

Each of the above antibody fragments retains the ability of specifically binding to the same antigen to which the full-length antibody binds, and/or competes with the full-length antibody for specifically binding the antigen.

The antigen-binding fragment of antibody (e.g., the above-mentioned antibody fragment) can be obtained from a given antibody (e.g., the antibody provided by the present invention) using a conventional technique known to those skilled in the art (e.g., recombinant DNA technology or enzymatic or chemical fragmentation methods), and can be screened for specificity in the same manner by which intact antibodies are screened.

In the context, unless specified definitely, when referring to the term "antibody", it includes not only the intact antibody but also an antigen-binding fragment of the antibody.

As used herein, the terms "monoclonal antibody", "mAb" have the same meaning and are used interchangeably, which refer to an antibody or a fragment of antibody derived from a population of highly homologous antibody molecules, that is, a population of identical antibody molecules, except for natural mutations that may occur spontaneously. A monoclonal antibody is highly specific for a single epitope on an antigen. Polyclonal antibody, relative to the monoclonal antibody, typically contains at least two or more different antibodies which usually recognize different epitopes on the antigen. In addition, the modifier "monoclonal" merely indicates the character of the antibody as being obtained from a highly homogeneous population of antibodies, and is not to be construed as requiring production of the antibody by any particular method.

The monoclonal antibody of the present invention can be prepared by a variety of techniques, such as hybridoma technology (see, e.g., Kohler et al. Nature, 256: 495, 1975), recombinant DNA technology (see, e.g., U.S. Pat. No. 4,816,567), or phage antibody library technology (see, e.g., Clackson et al. Nature352: 624-628, 1991, or Marks et al. J. Mol. Biol. 222: 581-597, 1991).

The antibodies can be purified by well-known techniques, such as affinity chromatography using protein A or protein G. Subsequently or alternatively, a specific antigen (a target molecule recognized by the antibody) or its epitope can be immobilized on a column and the immunospecific antibody can be purified by immunoaffinity chromatography. The purification of immunoglobulin may refer to, for example, D. Wilkinson (The Scientist, published by The Scientist, Inc., Philadelphia Pa., Vol. 14, No. 8 (Apr. 17, 2000), pp. 25-28).

As used herein, the term "chimeric antibody" refers to an antibody, in which a part of the light or/and heavy chain thereof is derived from one antibody (which may be derived from a specific species or belong to a specific antibody class or subclass), and another part of the light or/and heavy chain thereof is derived from another antibody (which may be derived from the same or different species or belong to the same or different antibody class or subclass), but in any case, it still retains the activity of binding to the target antigen (U.S. Pat. No. 4,816,567 to Cabilly et al.; Morrison et al., Proc. Natl. Acad. Sci. USA, 81: 6851 6855 (1984)). For example, the term "chimeric antibody" may comprise such an antibody (e.g., human-mouse chimeric antibody) in which the heavy and light chain variable regions of antibody are derived from a first antibody (e.g., murine antibody), while the heavy and light chain constant region of antibody are derived from a secondary antibody (e.g., a human antibody).

As used herein, the term "humanized antibody" refers to a genetically engineered non-human antibody of which the amino acid sequence is modified to increase homology to the sequence of human antibody. Generally, all or part of CDR regions of humanized antibody is derived from a non-human antibody (donor antibody), and all or part of non-CDR regions (e.g., variable region FR and/or constant region) is derived from a human immunoglobulin (receptor antibody). Humanized antibody generally retains the expected properties of the donor antibody, including, but not limited to, antigen specificity, affinity, reactivity, and the like. The donor antibody can be an antibody of mouse, rat, rabbit, or non-human primate (e.g., cynomolgus monkey) with the expected properties (e.g., antigen specificity, affinity, reactivity, etc.).

In this application, the expected properties of the antibody of the present invention include the abilities of: (1) specifically recognizing/binding CLDN18.2 (especially human CLDN18.2); (2) mediating CLDN18.2 internalization; (3) inducing the killing of a cell expressing human CLDN18.2 through antibody dependent cell-mediated cytotoxicity (ADCC); (4) inducing the killing of a cell expressing human CLDN18.2 through complement-dependent cytotoxicity (CDC); (5) preventing and/or treating a tumor. The antibody of the present invention has one or more of the aforementioned expected properties.

The chimeric antibody or humanized antibody of the present invention can be prepared based on the sequence of murine monoclonal antibody prepared as described above. The DNA encoding heavy and light chains can be obtained from a target murine hybridoma, and engineered to contain a non-murine (e.g., human) immunoglobulin sequence using a standard molecular biology technique.

To prepare a chimeric antibody, a variable region of murine immunoglobulin can be linked to a constant region of human immunoglobulin using a method known in the art (see, for example, U.S. Pat. No. 4,816,567 to Cabilly et al.). For example, a DNA encoding VH is operably linked to another DNA molecule encoding heavy chain constant region so as to obtain a full-length heavy chain gene. The sequence of human heavy chain constant region gene is known in the art (see, for example, Kabat, E A et al. (1991) Sequences of Proteins of Immunological Interest, Fifth Edition, U.S. Department of Health and Human Services, NIH Publication No. 91-3242), a DNA fragment containing these regions can be obtained by standard PCR amplification. The heavy chain constant region may be an IgG1, IgG2, IgG3, IgG4, IgA, IgE, IgM or IgD constant region, but is generally preferably an IgG1 or IgG4 constant region. For example, a DNA encoding VL is operably linked to another DNA molecule encoding light chain constant region CL so as to obtain a full-length light chain gene (as well as a Fab light chain gene). The sequence of human light chain constant region gene is known in the art (see, for example, Kabat, E A et al. (1991) Sequences of Proteins of Immunological Interest, Fifth Edition, US Department of Health and Human Services, NIH Publication No. 91-3242), a DNA fragment containing these regions can be obtained by standard PCR amplification. The light chain constant region may be a κ or λ constant region, but is generally preferably a κ constant region.

To prepare a humanized antibody, murine CDR regions can be grafted onto a human framework sequence by using any methods known in the art (see U.S. Pat. No. 5,225,539 to Winter; U.S. Pat. Nos. 5,530,101, 5,585,089, 5,693,762, and 6,180,370 to Queen et al.; And Lo, Benny, KC, editor, in Antibody Engineering: Methods and Protocols, volume 248, Humana Press, New Jersey, 2004). Alternatively, a transgenic animal can also be used, which is capable of producing a complete human antibody library without producing an endogenous immunoglobulin after immunization. For example, it has been reported that the homozygous deletion of the antibody heavy chain joining region (JH) gene in chimeric and germ-line mutant mice results in complete inhibition of endogenous antibody production, and transfer of the human germ-line immunoglobulin gene array in such germ-line mutant mice will result in the production of human antibodies upon antigen challenge (see, for example, Jakobovits et al., 1993, Proc. Natl. Acad. Sci. USA 90: 2551; Jakobovits et al., 1993, Nature 362: 255-258; Bruggermann et al., 1993, Year in Immunology 7: 33; and Duchosal et al., 1992, Nature 355: 258). Non-limiting examples of the above-mentioned transgenic animal include HuMAb mice (Medarex, Inc.) which comprises human immunoglobulin gene miniloci encoding unrearranged human heavy chains (μ and γ) and κ light chain immunoglobulin sequences, and a targeted mutation that inactivates endogenous and κ chain loci (see, for example, Lonberg et al. (1994) Nature 368 (6474): 856-859); or "KM Mouse™" which carries a human heavy chain transgene and human light chain transchromosome (see: patent application WO02/43478). Other methods of humanizing antibodies include phage display technology (Hoogenboom et al., 1991, J. Mol. Biol. 227: 381; Marks et al., J. Mol. Biol. 1991, 222: 581-597; Vaughan et al., 1996, Nature Biotech 14: 309).

As used herein, the term "germline antibody gene" or "germline antibody gene segment" refers to a sequence present in the genome of an organism encoding immunoglobulin, which has not undergone a maturation process that can lead to genetic rearrangements and mutations for expression of a particular immunoglobulin. In the present invention, the term "heavy chain germline gene" refers to a germline antibody gene or gene fragment encoding an immunoglobulin heavy chain, which comprises a V gene (variable), a D gene (diversity), a J gene (joining) and a C gene (constant); similarly, the term "light chain germline gene" refers to a germline antibody gene or gene fragment encoding an immunoglobulin light chain, which comprises a V gene (variable), a J gene (joining) and a C gene (constant). In the present invention, the amino acid sequence encoded by the germline antibody gene or germline antibody gene fragment is also referred to as a "germline sequence". The germline antibody gene or germline antibody gene fragment as well as corresponding germline sequence thereof are well known to those skilled in the art and can be obtained or queried from professional databases (e.g., IMGT, UNSWIg, NCBI, or VBASE2).

As used herein, the term "specifically bind" or "specific binding" refers to a non-random binding reaction between two molecules, such as a reaction between an antibody and an antigen to which it is directed. The strength or affinity of a specific binding interaction can be expressed in term of the equilibrium dissociation constant ($K_D$) of the interaction. In the present invention, the term "$K_D$" refers to the dissociation equilibrium constant of specific antibody-antigen interaction, which is used to describe the binding affinity between antibody and antigen. The lower the equilibrium dissociation constant, the tighter the antibody-antigen binding, and the higher the affinity between antibody and antigen. In some embodiments, an antibody specifically binding to an antigen (or an antibody being specific to an antigen) means that the antibody binds to the antigen with an affinity ($K_D$) of less than about $10^{-9}$ M, e.g. less than about $10^{-9}$ M, $10^{-10}$ M, $10^{-11}$ M or $10^{-12}$ M or less. The specific binding property between two molecules can be determined using a method known in the art, for example, determined by surface plasmon resonance (SPR) in a BIACORE instrument.

As used herein, the term "cytotoxic agent" comprises any agent which is harmful to a cell (e.g., killing a cell), such as a chemotherapeutic drug, a bacterial toxin, a phytotoxin or a radioisotope, and the like.

As used herein, the term "vector" refers to a nucleic acid vehicle into which a polynucleotide can be inserted. When a vector enables the expression of a protein encoded by the inserted polynucleotide, the vector is referred to as an expression vector. A vector can be introduced into a host cell by transformation, transduction or transfection, so that the genetic material elements carried by the vector can be expressed in the host cell. Vectors are well known to those skilled in the art and include, but are not limited to: plasmids; phagemids; cosmids; artificial chromosomes, such as yeast artificial chromosomes (YAC), bacterial artificial chromosomes (BAC) or P1-derived artificial chromosomes (PAC); phages such as λ phage or M13 phage and animal viruses. Animal viruses that can be used as vectors include, but are not limited to, retroviruses (including lentiviruses), adenoviruses, adeno-associated viruses, herpes viruses (e.g., herpes simplex virus), poxviruses, baculoviruses, papillomaviruses, papovavirus (e.g., SV40). A vector may comprise a variety of elements that control expression, including, but not limited to, promoter sequence, transcription initiation sequence, enhancer sequence, selection element, and reporter gene. In addition, the vector may comprise a replication initiation site.

As used herein, the term "host cell" refers to a cell into which a vector can be introduced, which includes, but is not limited to, prokaryotic cell such as *E. coli* or *Bacillus subtilis*, fungal cells such as yeast cells or *aspergillus*, insect cells such as S2 drosophila cells or Sf9, or animal cells such as fibroblast cells, CHO cells, COS cells, NSO cells, HeLa cells, BHK cells, HEK 293 cells, or human cells.

As used herein, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison ×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

As used herein, the terms "conservative substitution" and "conservative amino acid substitution" refer to amino acid substitutions which would not disadvantageously affect or change the expected properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having basic side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl Acad. Set USA 94: 412-417 (1997), which are incorporated herein by reference).

The 20 conventional amino acids involved herein are expressed in accordance with routine methods. See, for example, Immunology-A Synthesis (2nd Edition, E. S. Golub and D. R. Gren, Eds., Sinauer Associates, Sunderland, Mass. (1991)), which is incorporated herein by reference. In the invention, the terms "polypeptide" and "protein" have the same meanings, and can be used interchangeably. Moreover, in the invention, amino acids are generally expressed as one-letter codes and three-letter codes. For example, alanine may be expressed as A or Ala.

As used herein, the term "chimeric antigen receptor (CAR)" refers to an engineered T cell receptor having an extracellular targeting domain derived from an antibody (e.g., scFv) that is conjugated to one or more intracellular signaling domains of a T cell receptor. In the present invention, the term "chimeric antigen receptor T cell" refers to a T cell that expresses a CAR and has antigen specificity determined by the targeting domain of the CAR. Methods for preparing CARs (e.g., for use in cancer treatments) are known in the art, see, for example, Park et al., Trends Biotechnol., 29: 550-557, 2011; Grupp et al., NEnglJMed., 368: 1509-1518, 2013; Han et al., J.

Hematol Oncol., 6:47, 2013; PCT patent publications WO2012/079000, WO2013/059593; and US patent publication 2012/0213783, all of which are incorporated herein by reference in their entirety.

As used herein, the term "pharmaceutically acceptable carrier and/or excipient" refers to a carrier and/or excipient that is pharmacologically and/or physiologically compatible with a subject and an active ingredient, which is well known in the art (see, for example, Remington's Pharmaceutical Sciences. Edited by Gennaro A R, 19th ed. Pennsylvania: Mack Publishing Company, 1995) and includes, but is not limited to: pH adjusting agents, surfactants, adjuvants, ionic strength enhancers, diluents, agents to maintain osmotic pressure, agents to delay absorption, preservatives. For example, pH adjusting agents include, but are not limited to, phosphate buffered saline. Surfactants include, but are not limited to, cationic, anionic or non-ionic surfactants, such as TWEEN® 80 (polysorbate 80). Ionic strength enhancers include, but are not limited to, sodium chloride. Preservatives include, but are not limited to, various antibacterial and antifungal agents, such as parabens, trichloro-t-butanol, phenol, sorbic acid, and the like. Agents to maintain osmotic pressure include, but are not limited to, sugar, NaCl, and the like. Agents to delay absorption include, but are not limited to, monostearate and gelatin. Diluents include, but are not limited to, water, aqueous buffers (e.g., buffered saline), alcohols and polyols (e.g., glycerol), and the like. Preservatives include, but are not limited to, various antibacterial and antifungal agents, such as thimerosal, 2-phenoxyethanol, parabens, trichloro-t-butanol, phenol, sorbic acid, and the like. Stabilizers have the meaning commonly understood by those skilled in the art, which can stabilize the desired activity of active ingredient in drug, including but not limited to sodium glutamate, gelatin, SPGA, saccharides (e.g., sorbitol, mannitol, starch, sucrose, lactose, dextran, or glucose), amino acids (e.g., glutamic acid, glycine), proteins (e.g., dried whey, albumin, or casein) or degradation products thereof (e.g., lactalbumin hydrolysate), etc. In certain exemplary embodiments, the pharmaceutically acceptable carrier or excipient includes a sterile injectable liquid (e.g., an aqueous or non-aqueous suspension or solution). In certain exemplary embodiments, such sterile injectable liquid is selected from the group consisting of water for injection (WFI), bacteriostatic water for injection (BWFI), sodium chloride solution (e.g., 0.9% (w/v) NaCl), glucose solution (e.g., 5% glucose), surfactant-containing solution (e.g., 0.01% polysorbate 20), pH buffer solution (e.g., phosphate buffer solution), Ringer's solution, and any combination thereof.

As used herein, the term "prevention/preventing" refers to a method performed to prevent or delay the occurrence of a disease or disorder or symptom (e.g., a tumor) in a subject. As used herein, the term "treatment/treating" refers to a method performed to obtain a beneficial or desired clinical result. For the purposes of the present invention, the beneficial or desired clinical result includes, but is not limited to, easing symptom, reducing the scope of disease, stabilizing (i.e., no longer exacerbating) the state of disease, delaying or slowing the development of disease, improving or alleviating the status of disease, and alleviating a symptom (either in part or in whole), either detectable or undetectable. In addition, the term "treatment/treating" can also refer to prolonging survival period compared to the expected survival period (if not receiving treatment).

As used herein, the term "subject" refers to a mammal, such as a primate mammal, such as a human. In certain embodiments, the subject (e.g., a human) has a tumor (e.g., a tumor expressing CLDN18.2), or is at risk for having the above-mentioned diseases.

As used herein, the term "effective amount" refers to an amount sufficient to obtain or at least partially obtain a desired effect. For example, an effective amount to prevent a disease (e.g., a tumor) is an amount sufficient to prevent, stop or delay the onset of a disease (e.g., a tumor); an effective amount to treat a disease is an amount sufficient to cure or at least partially block a disease and complications thereof in a patient with the disease. The determination of such an effective amount is well within the capabilities of those skilled in the art. For example, the effective amount for a therapeutic use will depend on the severity of the disease to be treated, the overall state of the patient's immune system, the general condition of the patient such as age, weight and gender, administration route of the drugs, and additional therapies used simultaneously, etc.

As used herein, the term "immune effector cell" includes cells that have a hematopoietic origin and play a role in immune response, for example, lymphocytes such as B cells and T cells; natural killer cells; myeloid cells such as monocyte cells, macrophages, eosinophils, mast cells, basophils and granulocytes. In certain preferred embodiments, the immune effector cell is a T cell.

As used herein, the term "metastasis" refers to the spread of cancer cells from their original site to other parts of the body. The formation of metastasis is a very complex process and depends on the detachment of malignant cells from primary tumor, invasion of extracellular matrix, penetration of endothelial basement membrane to enter body cavities and blood vessels, and subsequent infiltration of target organs by blood transport. Finally, the growth of new tumors (i.e., secondary tumors or metastatic tumors) at target site depends on angiogenesis. Tumor metastasis often occur even after removal of the primary tumor, because tumor cells or components may remain and develop a metastatic potential. In one embodiment, the term "metastasis" according to the present invention relates to "distant metastasis", which relates to a metastasis which is remote from the primary tumor and the regional lymph node system. The cells of a secondary or metastatic tumor are similar to those in the original tumor. This means, for example, that if ovarian cancer metastasizes to liver, the secondary tumor is composed of abnormal ovarian cells (rather than abnormal liver cells). And thus the tumors in liver are called metastatic ovarian cancer (not liver cancer).

The Beneficial Effects of the Present Invention

Compared with the prior art, the technical solution of the present invention has the following beneficial effects:

The antibody of the invention is capable of specifically recognizing/binding to CLDN18.2, and is capable of inducing the killing of a cell (e.g., a tumor cell) expressing CLDN18.2 through ADCC and/or CDC. Therefore, the antibody of the present invention has a potential to be used for the prevention and/or treatment of a tumor, especially a tumor expressing CLDN18.2. The humanized antibody of the present invention not only retains the function and properties of the parent antibody, but also has a high degree of humanization, so that it can be safely administered to a human subject without triggering an immunogenic response. It is particularly surprising that the antibody of the present invention has significantly improved affinity and tumor-killing activity as compared to the known anti-CLDN18.2 antibodies. Therefore, the antibody (especially humanized antibody) of the present invention has great clinical value.

The embodiments of the present invention will be described in detail below with reference to the drawings and examples, but those skilled in the art will understand that the following drawings and examples are only used to illustrate the present invention, rather than limiting the scope of the present invention. Various objects and advantageous aspects of the present invention will become feasible to those skilled in the art from the following detailed description of the drawings and preferred embodiments.

DESCRIPTION OF THE DRAWINGS

FIG. 1A: HEK293T-hCLDN18.2; FIG. 1B: HEK293T-mCLDN18.2; FIG. 1C: HEK293T-hCLDN18.1;

FIG. 1D: HEK293T.

FIG. 3A: HEK293T-hCLDN18.2; FIG. 3B: KATO-III; FIG. 3C: NUGC4.

FIG. 4A: HEK293T-hCLDN18.2; FIG. 4B: KATO-III.

SEQUENCE INFORMATION

Figure 1A:
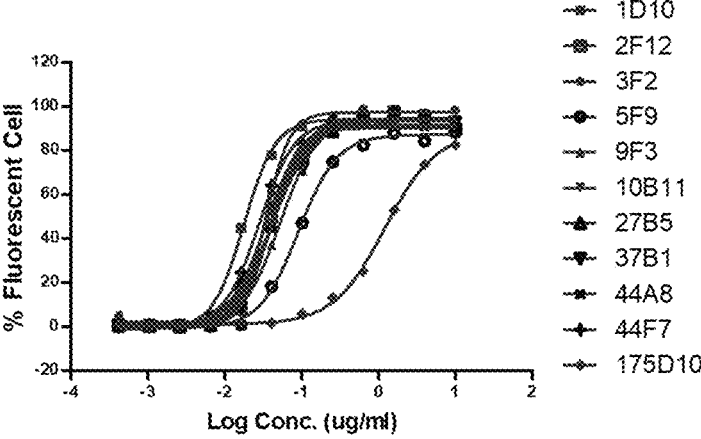
FIGS. 1A to 1D show the results of measuring the binding activity of anti-CLDN18.2 murine antibody to CLDN18.2 or CLDN18.1 on different cell surfaces, respectively.
Figure 1B:
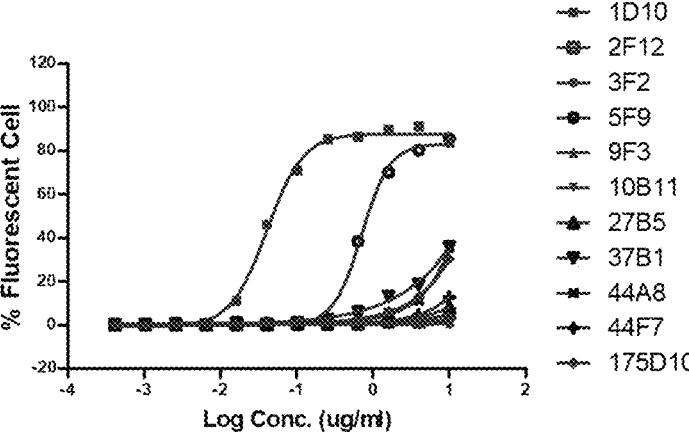
Figure 1C:
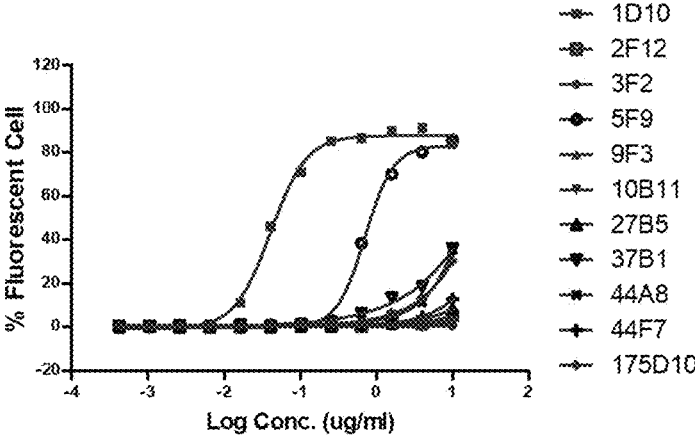
Figure 1D:
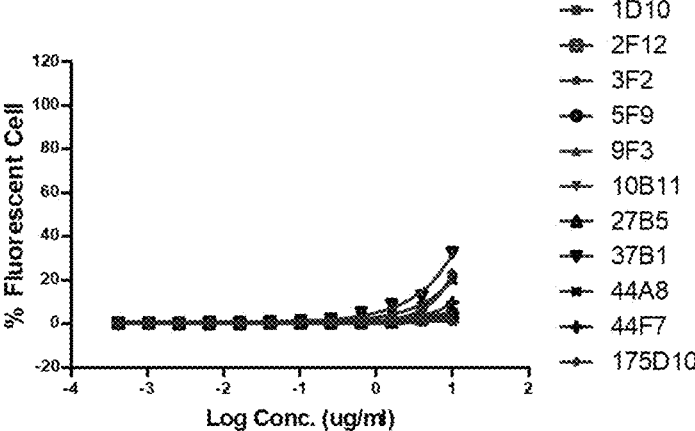

The information of some sequences involved in the present invention is provided in Table 1 below.

TABLE 1

| | | |
|---|---|---|
| | | Sequence description |

| SEQ ID NO | Description | Sequence information |
|---|---|---|
| 1 | 1D10 heavy chain variable region | QVQLQQPGAELVKPGASVKLSCKASGYTFTSYWMHWVKQRPGQGL EWIGMIYPNSGSINYNEKFKNKATLTVDKSSSTAYMQLSSLTSEDSA VYFCSVYFDYWGQGTTLTVSS |
| 2 | 1D10 light chain variable region | DIQGTQSPSSLSASLGERVSLTCRASQDIGSSLNWLQQEPDGTIKRLIY ATSSLDSGVPKRFSVSRSGSDYSLTISSLESEDFVDYYCLQYASSPPTF GGGTKLEIK |
| 3 | 1D10 HCDR1 | GYTFTSY |
| 4 | 1D10 HCDR2 | YPNSGS |
| 5 | 1D10 HCDR3 | YFDY |
| 6 | 1D10 LCDR1 | QDIGSSLN |
| 7 | 1D10 LCDR2 | ATSSLDS |
| 8 | 1D10 LCDR3 | LQYASSPPT |
| 9 | 2F12 heavy chain variable region | EVQLVESGGGLVKPGGSLKLSCAASGFTFSDYGIHWVRQAPEKGLE WVAYISSGSSTIYYADTVKGRFTISRDNAKNTLFLQMTSLRSEDTAIY YCAKWDRGNCFDYWGQGTTLTVSS |
| 10 | 2F12 light chain variable region | DIVLTQSPSSLTVTAGEKVTMSCKSSQSLLNSGNQKKYLTWYQQKV GQPPKLLIYWASIRECGVPDRFTGSGSGTDFILTISSVQAEDLAVYYC QNAYSYPLTFGAGTKLELK |
| 11 | 2F12 HCDR1 | GFTFSDY |
| 12 | 2F12 HCDR2 | SSGSST |
| 13 | 2F12 HCDR3 | WDRGNCFDY |
| 14 | 2F12 LCDR1 | KSSQSLLNSGNQKKYLT |
| 15 | 2F12 LCDR2 | WASIREC |
| 16 | 2F12 LCDR3 | QNAYSYPLT |
| 17 | 3F2 heavy chain variable region | EVMLVESGGGLVKPGGSLKLSCAASGFTFSTYAMSWVRQTPEKRLE WIATINDGGTYTYYPDNVKGRFTISRDNAKNNLYLHMSHLKSDDTAI HYCTRLARGNSMDYWGQGTSVTVSS |
| 18 | 3F2 light chain variable region | EVMLVESGGGLVKPGGSLKLSCAASGFTFSTYAMSWVRQTPEKRLE WIATINDGGTYTYYPDNVKGRFTISRDNAKNNLYLHMSHLKSDDTAI HYCTRLARGNSMDYWGQGTSVTVSS |
| 19 | 3F2 HCDR1 | GFTFSTY |
| 20 | 3F2 HCDR2 | NDGGTY |
| 21 | 3F2 HCDR3 | LARGNSMDY |
| 22 | 3F2 LCDR1 | KSSQSLLNSGNQKNYLT |
| 23 | 3F2 LCDR2 | WASTREY |
| 24 | 3F2 LCDR3 | QNNYIYPLT |
| 25 | 5F9 heavy chain variable region | QVQLQQSGAELVKPGASVKLSCKASGYTFTSYWMHWVKQRPGQGL EWIGMIHPNSVSTNYNEKFKSKATLTVDKSSSTAYMQLSSLTSEDSA VYYCAVYFDYWGQGTTLTVSS |
| 26 | 5F9 light chain variable region | DIQVTQSPSSLSASLGERVSLTCRASQDIGSSLNWLQQEPDGTIKRLIY ASSSLNSGVPKRFSVSRSGSDYSLTISSLESEDFVDYYCLQYATSPPTF GGGTKLEIK |
| 27 | 5F9 HCDR1 | GYTFTSY |
| 28 | 5F9 HCDR2 | HPNSVS |
| 29 | 5F9 HCDR3 | AVYFDY |

TABLE 1-continued

Sequence description

| SEQ ID NO | Description | Sequence information |
|---|---|---|
| 30 | 5F9 LCDR1 | RASQDIGSSLN |
| 31 | 5F9 LCDR2 | ASSSLNS |
| 32 | 5F9 LCDR3 | LQYATSPPT |
| 33 | 9F3 heavy chain variable region | EVRLQQSGPELVKPGASVKIPCKASGYKFTDYNMDWVKQSHGKSLE WIGEINPNNGGTIYNQKFKGKATLTVDKSSSTAYMELRSLTSEDTAV YYCARIYYGNSFAYWGQGTLVTVSS |
| 34 | 9F3 light chain variable region | DIVMTQSPSSLTVTAGEKVTMSCKSSQSLLNSGNLKNYLTWYQQKP GQPPKLLIYWASTRESGVPDRFTGSGSGTDFTLTISSVQAEDLAVYYC QNDYFYPLTFGAGTKLEIK |
| 35 | 9F3 HCDR1 | GYKFTDY |
| 36 | 9F3 HCDR2 | NPNNGG |
| 37 | 9F3 HCDR3 | IYYGNSFAY |
| 38 | 9F3 LCDR1 | KSSQSLLNSGNLKNYLT |
| 39 | 9F3 LCDR2 | WASTRES |
| 40 | 9F3 LCDR3 | QNDYFYPLT |
| 41 | 10B11 heavy chain variable region | QVQMKESGAELVKPGASVKISCKASGYAFSTYWMDWVKQRPGKGL EWIGQIYPGNGDTNYNGKFKGKATLTADKSSSTADMQLSSLTSEDSA VYFCARLGYGNSFTYWGQGTLVTVSA |
| 42 | 10B11 light chain variable region | DIQVTQSPSSLTVTAGEKVTMSCKSSQSLLNSGNQKNYLTWYQQKP GQPPKLLIYWASTRESGVPDRFTGSGFGTDFTLTISSVQAEDLAVYYC QNAYFYPFTFGSGTKLEIK |
| 43 | 10B11 HCDR1 | GYAFSTY |
| 44 | 10B11 HCDR2 | YPGNGD |
| 45 | 10B11 HCDR3 | LGYGNSFTY |
| 46 | 10B11 LCDR1 | KSSQSLLNSGNQKNYLT |
| 47 | 10B11 LCDR2 | WASTRES |
| 48 | 10B11 LCDR3 | QNAYFYPFT |
| 49 | 27B5 heavy chain variable region | QVQLQQPGTELVKPGASVKLSCKASGYTFTSYWMHWVKQRPGQGL EWIGNIHPSNGGSNHNEKFKSKATLTVDKSSSTAYMQLSSLTSEDSA VYYCAPIYYGNSLAYWGHGTLVTVSA |
| 50 | 27B5 light chain variable region | DVVMTQSPSSLTVTAGEKVTMSCKSSQSLLNSGNQKNYLTWYQQKP GQPPKLLLYWASTRESGVPDRFTGSGSGTDFTLTISSVQAEDLAVYY CQNSYFYPFTFGSGTKLEIK |
| 51 | 27B5 HCDR1 | GYTFTSY |
| 52 | 27B5 HCDR2 | HPSNGG |
| 53 | 27B5 HCDR3 | IYYGNSLAY |
| 54 | 27B5 LCDR1 | KSSQSLLNSGNQKNYLT |
| 55 | 27B5 LCDR2 | WASTRES |
| 56 | 27B5 LCDR3 | QNSYFYPF |
| 57 | 37B1 heavy chain variable region | EVRLQQSGPELVKPGASVKMSCKASGYSFTDYNMHWVKQSHGKSP EWVGYINPNKGGTGYNQKFKGKATLTVNKSSSTANMELRSLTSEDS AVYYCARIWYGNSFAYWGQGTLVTVSA |
| 58 | 37B1 light chain variable region | DVVMTQSPSSLTVTAGEKVTMSCKSSQSLLNSGNQKNYLTWYQQKP GQPPKLLIYWASTRESGVPDRFTGSGSGTDFTLTISSVQAEDLAVYFC QNDYFYPFTFGSGTKLEIK |

TABLE 1-continued

| | | Sequence description |
|---|---|---|

| SEQ ID NO | Description | Sequence information |
|---|---|---|
| 59 | 37B1 HCDR1 | GYSFTDY |
| 60 | 37B1 HCDR2 | NPNKGG |
| 61 | 37B1 HCDR3 | IWYGNSFAY |
| 62 | 37B1 LCDR1 | KSSQSLLNSGNQKNYLT |
| 63 | 37B1 LCDR2 | WASTRES |
| 64 | 37B1 LCDR3 | QNDYFYPFT |
| 65 | 44A8 heavy chain variable region | EVRLQQSGPELVKPGASVKMSCKASGYTFTDYNMHWVKQSHGKSL EWIGYINPKNGGIRYNQKFTGKATLTVNKSSSTAYMELRSLTSEDSA VYYCARGGYYGNTLDNWGQGTSVTVSS |
| 66 | 44A8 light chain variable region | DIVMTQSPSSLTLTAGEKVTMSCKSSQSLLNSGNQKNYLTWYQQKP GQPPKLLIYWASTSESGVPDRFTGSGSGTDFTLTISSVQAEDLAIYYC QNAYFYPWTFGGGTKLEIK |
| 67 | 44A8 HCDR1 | GYTFTDY |
| 68 | 44A8 HCDR2 | NPKNGG |
| 69 | 44A8 HCDR3 | GGYYGNTLDN |
| 70 | 44A8 LCDR1 | KSSQSLLNSGNQKNYLT |
| 71 | 44A8 LCDR2 | WASTSES |
| 72 | 44A8 LCDR3 | QNAYFYPWT |
| 73 | 44F7 heavy chain variable region | QVQLQQSGAELVRPGASVKMSCKASGYTFTSYNMHWVKQAPRQGL EWIGTIYPGNGDTSYNQKFKGKATLTVDKSSSTAYMQLSSLTSEDSA VYFCARGGYYGNSLDYWGQGTTLTVSS |
| 74 | 44F7 light chain variable region | DIQMTQSPSSLTVTAGEKVTMSCKSSQSLLNSGNQKNYLTWYQQKP GQPPKLLIYWASTRESGVPDRFTGSGSGTDFTLTISSVQAEDLAVYYC QNAYYYPFTFGSGTKLEIK |
| 75 | 44F7 HCDR1 | GYTFTSY |
| 76 | 44F7 HCDR2 | YPGNGD |
| 77 | 44F7 HCDR3 | GGYYGNSLDY |
| 78 | 44F7 LCDR1 | KSSQSLLNSGNQKNYLT |
| 79 | 44F7 LCDR2 | WASTRES |
| 80 | 44F7 LCDR3 | QNAYYYPFT |
| 81 | human IgG1 heavy chain constant region | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVD KKVEPKSCDKTHTCPPCPAPELLGGPSVFLFPPKPKDTLMISRTPEVT CVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSP GK |
| 82 | human κ light chain constant region | RTVAAPSVFIFPPSDEQLKSGTASVVCLLNNFYPREAKVQWKVDNAL QSGNSQESVTEQDSKDSTYSLSSTLTLSKADYEKHKVYACEVTHQGL SSPVTKSFNRGEC |
| 83 | CLDN18.2-ECL1 DNA | GACATGTGGAGCACCCAGGACCTGTACGACAACCCCGTGACCAG CGTGTTCCAGTACGAGGGCCTGTGGAGGAGCTGCGTGAGGCAGA GCAGCGGCTTCACCGAGTGCAGGCCCTACTTCACCATCCTGGGCC TGCCCGCCATGCTGCAGGCCGTGAGG |
| 84 | CLDN18.2-ECL1-C3d DNA | GACCAGTGGAGCACCCAAGACTTGTACAACAACCCCGTAACAGC TGTTTTCAACTACCAGGGGCTGTGGCGCTCCTGTGTCCGAGAGAG CTCTGGCTTCACCGAGTGCCGGGGCTACTTCACCCTGCTGGGGCT GCCAGCCATGCTGCAGGCAGTGCGAGGCAGCGGCAGCGGCGGCG |

TABLE 1-continued

Sequence description

| SEQ ID NO | Description | Sequence information |
|---|---|---|
| | | GCGGCAGCGGCGGCGGCGGCAGCGGCAGCCACCTGATCGTGACC CCCGCCGGCTGCGGCGAGCAGAACATGATCGGCATGACCCCCAC CGTGATCGCCGTGCACTACCTGGACCAGACCGAGCAGTGGGAGA AGTTCGGCATCGAGAAGAGGCAGGAGGCCCTGGAGCTGATCAAG AAGGGCTACACCCAGCAGCTGGCCTTCAAGCAGCCCAGCAGCGC CTACGCCGCCTTCAACAACAGGCCCCCCAGCACCTGGCTGACCGC CTACGTGGTGAAGGTGTTCAGCCTGGCCGCCAACCTGATCGCCAT CGACAGCCACGTGCTGTGCGGCGCCGTGAAGTGGCTGATCCTGGA GAAGCAGAAGCCCGACGGCGTGTTCCAGGAGGACGGCCCCGTGA TCCACCAGGAGATGATCGGCGGCTTCAGGAACGCCAAGGAGGCC GACGTGAGCCTGACCGCCTTCGTGCTGATCGCCCTGCAGGAGGCC AGGGACATCTGCGAGGGCCAGGTGAACAGCCTGCCCGGCAGCAT CAACAAGGCCGGCGAGTACATCGAGGCCAGCTACATGAACCTGC AGAGGCCCTACACCGTGGCCATCGCCGGCTACGCCCTGGCCCTGA TGAACAAGCTGGAGGAGCCCTACCTGGGCAAGTTCCTGAACACC GCCAAGGACAGGAACAGGTGGGAGGAGCCCGACCAGCAGCTGTA CAACGTGGAGGCCACCAGCTACGCCCTGCTGGCCCTGCTGCTGCT GAAGGACTTCGACAGCGTGCCCCCCGTGGTGAGGTGGCTGAACG AGCAGAGGTACTACGGCCGGCGGCTACGGCAGCACCCAGGCCACC TTCATGGTGTTCCAGGCCCTGGCCCAGTACCAGACCGACGTGCCC GACCACAAGGACCTGAACATGGACGTGAGCTTCCACCTGCCCAGC AGGGGCAGCGAGGAGTTC |
| 85 | hCLDN18.2 DNA | ATGGCCGTGACCGCCTGCCAGGGCCTGGGCTTCGTGGTGAGCCTG ATCGGCATCGCCGGCATCATCGCCGCCACCTGCATGGACCAGTGG AGCACCCAGGACCTGTACAACAACCCCGTGACCGCCGTGTTCAAC TACCAGGGCCTGTGGAGGAGCTGCGTGAGGGAGAGCAGCGGCTT CACCGAGTGCAGGGGCTACTTCACCCTGCTGGGCCTGCCCGCCAT GCTGCAGGCCGTGAGGGCCCTGATGATCGTGGGCATCGTGCTGGG CGCCATCGGCCTGCTGGTGAGCATCTTCGCCCTGAAGTGCATCAG GATCGGCAGCATGGAGGACAGCGCCAAGGCCAACATGACCCTGA CCAGCGGCATCATGTTCATCGTGAGCGGCCTGTGCGCCATCGCCG GCGTGAGCGTGTTCGCCAACATGCTGGTGACCAACTTCTGGATGA GCACCGCCAACATGTACACCGGCATGGGCGGCATGGTGCAGACC GTGCAGACCAGGTACACCTTCGGCGCCGCCCTGTTCGTGGGCTGG GTGGCCGGCGGCCTGACCCTGATCGGCGGCGTGATGATGTGCATC GCCTGCAGGGGCCTGGCCCCCGAGGAGACCAACTACAAGGCCGT GAGCTACCACGCCAGCGGCCACAGCGTGGCCTACAAGCCCGGCG GCTTCAAGGCCAGCACCGGCTTCGGCAGCAACACCAAGAACAAG AAGATCTACGACGGCGGCGCCAGGACCGAGGACGAGGTGCAGAG CTACCCCAGCAAGCACGACTACGTG |
| 86 | human CLDN18.2 amino acid sequence | MAVTACQGLGFVVSLIGIAGIIAATCMDQWSTQDLYNNPVTAVFNY QGLWRSCVRESSGFTECRGYFTLLGLPAMLQAVRALMIVGLVLGIG LLVSIFALKCIRIGSMEDSAKANMTLTSGIMFIVSGLCAIAGVSVFAN MLVTNFWMSTANMYTGMGGMVQTVQTRYTFGAALFVGWVAGGL TLIGGVMMCIACRGLAPEETNYKAVSYHASGHSVAYKPGGFKASTG FGSNTKNKKIYDGGARTEDEVQSYPSKHDYV |
| 87 | mouse CLDN18.2 amino acid sequence | MSVTACQGLGFVVSLIGFAGIIAATCMDQWSTQDLYNNPVTAVFNY QGLWRSCVRESSGFTECRGYFTLLGLPAMLQAVRALMIVGIVLGVIG ILVSIFALKCIRIGSMDDSAKAKMTLTSGILFIISGISAIIGVSVFANMLV TNFWMSTANMYSGMGGMGGMVQTVQTRYTFGAALFVGWVAGGL TLIGGVMMCIACRGLTPDDSNFKAVSYHASGQNVAYRPGGFKASTG FGSNTRNKKIYDGGARTEDDEQSHPTKYDYV |
| 88 | human CLDN 18.1 amino acid sequence | MSTTTCQVVAFLLSILGLAGCIAATGMDMWSTQDLYDNPVTSVFQY EGLWRSCVRQSSGFTECRPYFTILGLPAMLQAVRALMIVGIVLGAIGL LVSIFALKCIRIGSMEDSAKANMTLTSGIMFIVSGLCAIAGVSVFANM LVTNFWMSTANMYTGMGGMVQTVQTRYTFGAALFVGWVAGGLTL IGGVMMCIACRGLAPEETNYKAVSYHASGHSVAYKPGGFKASTGFG SNTKNKKIYDGGARTEDEVQSYPSKHDYV |
| 89 | 175D10 heavy chain amino acid sequence | QVQLQQPGAELVRPGASVKLSCKASGYTFTSYWINWVKQRPGQGLE WIGNIYPSDSYTNYNQKFKDKATLTVDKSSSTAYMQLSSPTSEDSAV YYCTRSWRGNSFDYWGQGTTLTVSSASTKGPSVFPLAPSSKSTSGGT AALGCLVKDYFPEPVTVSWNSGALTSGVHTFPAVLQSSGLYSLSSVV TVPSSSLGTQTYICNVNHKPSNTKVDKRVEPKSCDKTHTCPPCPAPEL LGGPSVFLFPPKPKDTLMISRTPEVTCVVVDVSHEDPEVKFNWYVDG VEVHNAKTKPREEQYNSTYRVVSVLTVLHQDWLNGKEYKCKVSNK ALPAPIEKTISKAKGQPREPQVYTLPPSREEMTKNQVSLTCLVKGFYP SDIAVEWESNGQPENNYKTTPPVLDSDGSFFLYSKLTVDKSRWQQG NVFSCSVMHEALHNHYTQKSLSLSPGK |

TABLE 1-continued

| | Sequence description | |
|---|---|---|
| SEQ ID NO | Description | Sequence information |
| 90 | 175D10 light chain amino acid sequence | DIVMTQSPSSLTVTAGEKVTMSCKSSQSLLNSGNQKNYLTWYQQKP GQPPKLLIYWASTRESGVPDRFTGSGSGTDFTLTISSVQAEDLAVYYC QNDYSYPFTFGSGTKLEIKRTVAAPSVFIFPPSDEQLKSGTASVVCLL NNFYPREAKVQWKVDNALQSGNSQESVTEQDSKDSTYSLSSTLTLS KADYEKHKVYACEVTHQGLSSPVTKSFNRGEC |
| 91 | 7004-09hu15 heavy chain variable region | QVQLVQSGAEVKKPGASVKVSCKASGYTFTSYYMHWVRQAPGQGL EWMGTIYPGNGDTSYNQKFQGRVTMTRDKSTSTVYMELSSLRSEDT AVYFCARGGYYGNSLDYWGQGTLVTVS |
| 92 | 7004-09hu15 light chain variable region | DIVMTQSPDSLAVSLGERATINCKSSQSVLNSGNQKNYLAWYQQKP GQPPKLLIYWASTRESGVPDRFSGSGSGTDFTLTISSLQAEDVAVYYC QNAYYYPFTFGQGTKLEIK |
| 93 | 7004-09hu15 HCDR1 | GYTFTSY |
| 94 | 7004-09hu15 HCDR2 | YPGNGD |
| 95 | 7004-09hu15 HCDR3 | GGYYGNSLDY |
| 96 | 7004-09hu15 LCDR1 | KSSQSVLNSGNQKNYLA |
| 97 | 7004-09hu15 LCDR2 | WASTRES |
| 98 | 7004-09hu15 LCDR3 | QNAYYYPFT |
| 99 | 7004-09hu09 heavy chain variable region | QVQLVQSGAEVKKPGASVKVSCKASGYTFTSYNMHWVRQAPGQGL EWMGTIYPGNGDTSYNQKFQGRVTMTRDKSTSTVYMELSSLRSEDT AVYFCARGGYYGNSLDYWGQGTLVTVS |
| 100 | 7004-09hu09 light chain variable region | DIVMTQSPDSLAVSLGERATINCKSSQSLLNSGNQKNYLAWYQQKP GQPPKLLIYWASTRESGVPDRFSGSGSGTDFTLTISSLQAEDVAVYYC QNAYYYPFTFGQGTKLEIK |
| 101 | 7004-09hu10 heavy chain variable region | QVQLVQSGAEVKKPGASVKVSCKASGYTFTSYYMHWVRQAPGQGL EWMGTIYPGNGDTSYNQKFQGRVTMTRDKSTSTVYMELSSLRSEDT AVYFCARGGYYGNSLDYWGQGTLVTVS |
| 102 | 7004-09hu10 light chain variable region | DIVMTQSPDSLAVSLGERATINCKSSQSLLNSGNQKNYLTWYQQKPG QPPKLLIYWASTRESGVPDRFSGSGSGTDFTLTISSLQAEDVAVYYCQ NAYYYPFTFGQGTKLEIK |
| 103 | 1D10 heavy chain variable region encoding nucleic acid sequence | CAGGTCCAACTGCAGCAGCCTGGGGCTGAGCTGGTAAAGCCTGG GGCTTCAGTGAAGTTGTCCTGCAAGGCTTCTGGCTACACTTTCACC AGCTACTGGATGCACTGGGTGAAGCAGAGGCCTGGACAAGGCCT TGAGTGGATTGGAATGATTTATCCTAATAGTGGTAGCATTAACTA CAATGAGAAGTTCAAGAACAAGGCCACACTGACTGTAGACAAAT CCTCCAGCACAGCCTACATGCAACTCAGCAGCCTGACATCTGAGG ACTCTGCGGTCTATTTCTGTTCTGTCTACTTTGACTACTGGGGCCA AGGCACCACTCTCACAGTCTCCTCA |
| 104 | 1D10 light chain variable region encoding nucleic acid sequence | GACATCCAGGGGACACAGTCTCCATCCTCCTTATCTGCCTCTCTGG GAGAAAGAGTCAGTCTCACTTGTCGGGCAAGTCAGGACATTGGTA GTAGCTTAAACTGGCTTCAGCAGGAACCAGATGGAACTATTAAAC GCCTGATCTACGCCACATCCAGTTTAGATTCTGGTGTCCCCAAAA GGTTCAGTGTCAGTAGGTCTGGGTCAGATTATTCTCTCACCATCA GCAGCCTTGAGTCTGAAGATTTTGTAGACTATTACTGTCTACAAT ATGCTAGTTCTCCTCCGACGTTCGGTGGAGGCACCAAACTGGAAA TCAAA |
| 105 | 2F12 heavy chain variable region encoding nucleic acid sequence | GAGGTGCAGCTGGTGGAGTCTGGGGGAGGCTTAGTGAAGCCTGG AGGGTCCCTGAAACTCTCCTGTGCTGCCTCTGGATTCACTTTCAGT GACTATGGGATCCACTGGGTTCGTCAGGCTCCAGAGAAGGGGCTG GAGTGGGTTGCATACATTAGTAGTGGCAGTAGTACCATCTACTAT GCAGACACAGTGAAGGGCCGATTCACCATCTCCAGAGACAATGC CAAGAACACCCTGTTCCTGCAAATGACCAGTCTGAGGTCTGAGGA CACGGGCCATATATTACTGTGCAAAGTGGGACCGGGGTAACTGCTT TGACTACTGGGGCCAAGGCACCACTCTCACAGTCTCCTCA |

TABLE 1-continued

| | Sequence description | |
| --- | --- | --- |

| SEQ ID NO | Description | Sequence information |
| --- | --- | --- |
| 106 | 2F12 light chain variable region encoding nucleic acid sequence | GACATTGTGTTGACCCAGTCTCCATCCTCCCTGACTGTGACAGCA GGAGAGAAGGTCACTATGAGCTGCAAGTCCAGTCAGAGTCTGTTA AACAGTGGAAATCAAAAGAAATACTTGACCTGGTATCAGCAGAA AGTAGGGCAGCCTCCTAAACTGTTGATTTACTGGGCATCCATTAG GGAATGTGGGGTCCCTGATCGCTTCACAGGCAGTGGATCTGGAAC AGATTTCATTCTCACCATCAGCAGTGTGCAGGCTGAAGACCTGGC AGTTTATTACTGTCAGAATGCTTATAGTTATCCGCTCACGTTCGGT GCTGGGACCAAGCTGGAGCTGAAA |
| 107 | 3F2 heavy chain variable region encoding nucleic acid sequence | GAGGTGATGCTGGTGGAGTCTGGGGGAGGCTTAGTGAAGCCTGG AGGGTCCCTGAAACTCTCCTGTGCAGCCTCTGGATTCACTTTCAGT ACCTATGCCATGTCTTGGGTTCGCCAGACTCCGGAAAAGAGGCTG GAGTGGATCGCAACCATTAATGATGGTGGTACTTACACCTACTAT CCAGACAATGTAAAGGGCCGATTCACCATCTCCAGAGACAATGCC AAGAACAACCTGTACCTACACATGAGCCATCTGAAGTCTGACGAC ACAGCCATCCATTACTGTACAAGACTAGCGAGGGGGAATTCTATG GACTACTGGGGTCAAGGAACCTCAGTCACCGTCTCCTCA |
| 108 | 3F2 light chain variable region encoding nucleic acid sequence | GAGGTGATGCTGGTGGAGTCTGGGGGAGGCTTAGTGAAGCCTGG AGGGTCCCTGAAACTCTCCTGTGCAGCCTCTGGATTCACTTTCAGT ACCTATGCCATGTCTTGGGTTCGCCAGACTCCGGAAAAGAGGCTG GAGTGGATCGCAACCATTAATGATGGTGGTACTTACACCTACTAT CCAGACAATGTAAAGGGCCGATTCACCATCTCCAGAGACAATGCC AAGAACAACCTGTACCTACACATGAGCCATCTGAAGTCTGACGAC ACAGCCATCCATTACTGTACAAGACTAGCGAGGGGGAATTCTATG GACTACTGGGGTCAAGGAACCTCAGTCACCGTCTCCTCA |
| 109 | 5F9 heavy chain variable region encoding nucleic acid sequence | CAGGTCCAACTGCAGCAGTCTGGGGCTGAGCTGGTAAAGCCTGG GGCTTCAGTGAAGTTGTCCTGCAAGGCTTCTGGCTACACTTTCACC AGCTACTGGATGCACTGGGTGAAGCAGAGGCCTGGACAAGGCCT TGAGTGGATTGGAATGATTCATCCTAATAGTGTTAGTACTAACTA CAATGAGAAGTTCAAGAGCAAGGCCACACTGACTGTAGACAAAT CCTCCAGCACAGCCTACATGCAACTCAGCAGCCTGACATCTGAGG ACTCTGCGGTCTATTACTGTGCTGTCTACTTTGACTACTGGGGCCA AGGCACCACTCTCACAGTCTCCTCA |
| 110 | 5F9 light chain variable region encoding nucleic acid sequence | GACATCCAGGTGACACAGTCTCCATCCTCCTTATCTGCCTCTCTGG GAGAAAGAGTCAGTCTCACTTGTCGGGCAAGTCAGGACATTGGTA GTAGCTTAAACTGGCTTCAGCAGGAACCAGATGGAACTATTAAAC GCCTGATCTACGCCTCATCCAGTTTAAATTCTGGTGTCCCCAAAA GGTTCAGTGTCAGTAGGTCTGGGTCAGATTATTCTCTCACCATCA GCAGCCTTGAGTCTGAAGATTTTGTAGACTATTACTGTCTACAAT ATGCTACTTCTCCTCCGACGTTCGGTGGAGGCACCAAGCTGGAAA TCAAA |
| 111 | 9F3 heavy chain variable region encoding nucleic acid sequence | GAGGTTCGGCTGCAACAGTCTGGACCTGAGCTGGTGAAGCCTGGG GCTTCAGTGAAGATACCCTGCAAGGCTTCTGGATACAAATTCACT GACTACAACATGGACTGGGTGAAGCAGAGCCATGGAAAGAGCCT TGAGTGGATTGGAGAAATTAATCCTAACAATGGTGGTACTATCTA CAACCAGAAGTTCAAGGGCAAGGCCACATTGACTGTAGACAAGT CCTCCAGCACAGCCTACATGGAGCTCCGCAGCCTGACATCTGAGG ACACTGCAGTCTATTACTGTGCAAGAATTTACTATGGTAACTCCTT TGCTTACTGGGGCCAAGGGACTCTGGTCACTGTCTCTTCA |
| 112 | 9F3 light chain variable region encoding nucleic acid sequence | GACATTGTGATGACACAGTCTCCATCCTCCCTGACTGTGACAGCA GGAGAGAAGGTCACTATGAGCTGCAAGTCCAGTCAGAGTCTGTTA AACAGTGGAAATCTAAAGAACTACTTGACCTGGTACCAGCAGAA ACCAGGGCAGCCTCCTAAACTTTTGATCTACTGGGCATCCACTAG GGAATCTGGGGTCCCTGATCGCTTCACAGGCAGTGGATCTGGAAC AGATTTCACTCTCACCATCAGCAGTGTGCAGGCTGAAGACCTGGC AGTTTATTACTGTCAGAATGATTATTTTTATCCGCTCACGTTCGGT GCTGGGACCAAGCTGGAAATCAAA |
| 113 | 10B11 heavy chain variable region encoding nucleic acid sequence | CAGGTGCAAATGAAGGAGTCTGGGGCTGAGCTGGTGAAGCCTGG GGCCTCAGTGAAGATTTCCTGCAAAGCTTCTGGCTACGCATTCAG TACCTACTGGATGGACTGGGTGAAGCAGAGGCCTGGAAAGGGTC TTGAGTGGATTGGACAGATTTATCCTGGAAATGGTGATACTAACT ACAACGGAAAGTTCAAGGGCAAGGCCACACTGACTGCAGACAAA TCCTCCAGCACAGCCGACATGCAGCTCAGCAGCCTGACCTCTGAG GACTCTGCGGTCTATTTCTGTGCAAGATTGGGGTATGGTAACTCG TTTACTTACTGGGGCCAAGGGACTCTGGTCACTGTCTCTGCA |

TABLE 1-continued

Sequence description

SEQ
ID
NO  Description        Sequence information 114  10B11 light chain   GACATCCAGGTGACACAGTCTCCATCCTCCCTGACTGTGACAGCA
     variable region     GGAGAGAAGGTCACTATGAGCTGCAAGTCCAGTCAGAGTCTGTTA
     encoding nucleic    AACAGTGGAAATCAAAAGAACTACTTGACCTGGTACCAGCAGAA
     acid sequence       ACCAGGGCAGCCTCCTAAACTGTTGATCTACTGGGCATCCACTAG
                         GGAATCTGGGGTCCCTGATCGCTTCACAGGCAGTGGATTTGGAAC
                         AGATTTCACTCTCACCATCAGCAGTGTGCAGGCTGAAGACCTGGC
                         AGTTTATTACTGTCAGAATGCTTATTTTTATCCATTCACGTTCGGC
                         TCGGGGACAAAGCTGGAAATCAAA 115  27B5 heavy chain    CAGGTCCAACTGCAGCAGCCTGGGACCGAGCTGGTGAAGCCTGG
     variable region     GGCTTCAGTGAAGCTGTCCTGCAAGGCTTCTGGCTACACCTTCAC
     encoding nucleic    CAGCTACTGGATGCACTGGGTGAAGCAGAGGCCTGGACAAGGCC
     acid sequence       TTGAGTGGATTGGAAATATTCATCCTAGCAATGGTGGTAGTAACC
                         ACAATGAGAAGTTCAAGAGCAAGGCCACACTGACTGTAGACAAA
                         TCCTCCAGCACAGCCTACATGCAGCTCAGCAGCCTGACATCTGAG
                         GACTCTGCGGTCTATTATTGTGCGCCTATCTACTATGGTAACTCGC
                         TTGCTTATTGGGGCCACGGGACTCTGGTCACTGTCTCTGCA 116  27B5 light chain    GATGTTGTGATGACCCAGTCTCCATCCTCCCTGACTGTGACAGCA
     variable region     GGAGAGAAGGTCACTATGAGCTGCAAGTCCAGTCAGAGTCTGTTA
     encoding nucleic    AACAGTGGAAATCAAAAGAACTACTTGACCTGGTACCAGCAGAA
     acid sequence       ACCAGGGCAGCCTCCTAAACTATTGCTCTACTGGGCATCCACTAG
                         GGAATCTGGGGTCCCTGATCGCTTCACAGGCAGTGGATCTGGAAC
                         AGATTTCACTCTCACCATCAGCAGTGTGCAGGCTGAAGACCTGGC
                         AGTTTATTACTGTCAGAATAGTTATTTTTATCCATTCACGTTCGGC
                         TCGGGGACAAAGCTGGAAATCAAA 117  37B1 heavy chain    GAGGTTCGGCTGCAACAGTCTGGACCTGAGCTGGTGAAGCCTGGG
     variable region     GCTTCAGTGAAGATGTCCTGCAAGGCTTCTGGATACTCATTCACT
     encoding nucleic    GACTACAACATGCACTGGGTGAAGCAGAGCCATGGAAAGAGCCC
     acid sequence       TGAGTGGGTTGGATATATTAACCCTAACAAGGGTGGTACTGGCTA
                         CAACCAGAAGTTCAAGGGCAAGGCCACATTGACTGTAAACAAGT
                         CCTCCAGCACAGCCAACATGGAGCTCCGCAGCCTGACATCGGAG
                         GATTCCGCAGTCTATTACTGTGCACGGATATGGTATGGTAATTCG
                         TTTGCTTACTGGGGCCAAGGGACTCTGGTCACTGTCTCAGCA 118  37B1 light chain    GATGTTGTGATGACACAGTCTCCATCCTCCCTGACTGTGACAGCA
     variable region     GGAGAGAAGGTCACTATGAGCTGCAAGTCCAGTCAGAGTCTGTTA
     encoding nucleic    AACAGTGGAAATCAAAAGAACTACTTGACCTGGTACCAGCAGAA
     acid sequence       ACCAGGGCAGCCTCCTAAACTGTTGATCTACTGGGCATCCACTAG
                         GGAATCTGGGGTCCCTGATCGCTTCACAGGCAGTGGATCTGGAAC
                         AGATTTCACTCTCACCATCAGCAGTGTGCAGGCTGAAGACCTGGC
                         AGTTTATTTCTGTCAGAATGATTATTTTTATCCATTCACGTTCGGC
                         TCGGGGACAAAGTTGGAAATAAAA 119  44A8 heavy chain    GAGGTTCGGCTGCAACAGTCTGGACCTGAGCTGGTGAAGCCTGGG
     variable region     GCTTCAGTGAAGATGTCCTGCAAGGCTTCTGGATACACATTCACT
     encoding nucleic    GACTACAACATGCACTGGGTGAAACAGAGCCATGGAAAGAGCCT
     acid sequence       TGAGTGGATTGGATATATTAACCCTAAGAATGGTGGTATTAGATA
                         CAACCAGAAGTTCACGGGCAAGGCCACATTGACTGTAAACAAGT
                         CCTCCAGCACAGCCTACATGGAGCTCCGCAGCCTGACATCGGAGG
                         ATTCTGCAGTCTATTACTGTGCAAGAGGGGGTTACTACGGTAATA
                         CTTTGGACAACTGGGGTCAAGGAACCTCAGTCACCGTCTCCTCA 120  44A8 light chain    GACATTGTGATGACACAGTCTCCATCCTCCCTGACTCTGACAGCA
     variable region     GGAGAGAAGGTCACTATGAGCTGCAAGTCCAGTCAGAGTCTGTTA
     encoding nucleic    AACAGTGGAAATCAAAAGAACTACTTGACCTGGTACCAGCAGAA
     acid sequence       ACCAGGGCAGCCTCCTAAACTGTTGATCTACTGGGCATCCACTAG
                         TGAATCTGGGGTCCCTGATCGCTTCACAGGCAGTGGATCTGGAAC
                         AGATTTCACTCTCACCATCAGCAGTGTGCAGGCTGAAGACCTGGC
                         AATTTATTACTGTCAGAATGCTTATTTTTATCCGTGGACGTTCGGT
                         GGAGGCACCAAACTGGAGATCAAA 121  44F7 heavy chain    CAGGTCCAACTGCAGCAGTCTGGGGCTGAGCTGGTGAGGCCTGG
     variable region     GGCCTCAGTGAAGATGTCCTGCAAGGCTTCTGGCTACACATTTAC
     encoding nucleic    CAGTTACAATATGCACTGGGTAAAGCAGGCACCTAGACAGGGCC
     acid sequence       TGGAATGGATTGGAACTATTTATCCAGGAAATGGTGATACTTCCT
                         ACAATCAGAAGTTCAAGGGCAAGGCCACACTGACTGTAGACAAA
                         TCCTCCAGCACAGCCTACATGCAGCTCAGCAGCCTGACATCTGAG
                         GACTCTGCGGTCTATTTCTGTGCAAGAGGGGGCTACTATGGTAAC
                         TCTCTTGACTACTGGGGCCAAGGCACCACTCTCACAGTCTCCTCA TABLE 1-continued Sequence description

| SEQ ID NO | Description | Sequence information |
|---|---|---|
| 122 | 44F7 light chain variable region encoding nucleic acid sequence | GACATCCAGATGACACAGTCTCCATCCTCCCTGACTGTGACAGCA GGAGAGAAGGTCACTATGAGCTGCAAGTCCAGTCAGAGTCTGTTA AACAGTGGAAATCAAAAGAACTACTTGACCTGGTACCAGCAGAA ACCAGGACAGCCTCCTAAACTGTTGATCTACTGGGCATCCACTAG GGAATCTGGGGTCCCTGATCGCTTCACAGGCAGTGGATCTGGAAC AGATTTCACTCTCACCATCAGCAGTGTGCAGGCTGAAGACCTGGC AGTTTATTACTGTCAGAATGCTTATTATTATCCATTCACGTTCGGC TCGGGGACAAAGCTGGAGATCAAA |
| 123 | 7004-09hu15 heavy chain variable region encoding nucleic acid sequence | CAGGTGCAGCTGGTGCAGTCTGGGGCTGAGGTGAAGAAGCCTGG GGCCTCAGTGAAGGTTTCCTGCAAGGCATCTGGATACACCTTCAC CAGCTACTATATGCACTGGGTGCGACAGGCCCCTGGACAAGGGCT TGAGTGGATGGGAACTATCTATCCTGGTAATGGTGATACAAGCTA CAACCAGAAGTTCCAGGGCAGAGTCACCATGACCAGGGACAAGT CCACGAGCACAGTCTACATGGAGCTGAGCAGCCTGAGATCTGAG GACACGGCCGTGTATTTCTGTGCGAGAGGCGGGTATTATGGGAAC AGTCTTGACTACTGGGGCCAGGGAACCCTGGTCACCGTCTCC |
| 124 | 7004-09hu15 light chain variable region encoding nucleic acid sequence | GACATCGTGATGACCCAGTCTCCAGACTCCCTGGCTGTGTCTCTG GGCGAGAGGGCCACCATCAACTGCAAGTCCAGCCAGAGTGTTTTA AACAGCGGCAACCAGAAGAACTACTTAGCTTGGTACCAGCAGAA ACCAGGACAGCCTCCTAAGTTGCTCATTTACTGGGCGTCTACCCG GGAATCCGGGGTCCCTGACCGATTCAGTGGCAGCGGGTCTGGGAC AGATTTCACTCTCACCATTAGCAGCCTGCAGGCTGAAGATGTGGC AGTTTATTACTGTCAGAATGCATATTACTACCCCTTCACTTTTGGC CAGGGGACCAAGCTGGAGATCAAA |
| 125 | 7004-09hu09 heavy chain variable region encoding nucleic acid sequence | CAGGTGCAGCTGGTGCAGTCTGGGGCTGAGGTGAAGAAGCCTGG GGCCTCAGTGAAGGTTTCCTGCAAGGCATCTGGATACACCTTCAC CAGCTACAACATGCACTGGGTGCGACAGGCCCCTGGACAAGGGC TTGAGTGGATGGGAACTATCTATCCTGGTAATGGTGATACAAGCT ACAACCAGAAGTTCCAGGGCAGAGTCACCATGACCAGGGACAAG TCCACGAGCACAGTCTACATGGAGCTGAGCAGCCTGAGATCTGAG GACACGGCCGTGTATTTCTGTGCGAGAGGCGGGTATTATGGGAAC AGTCTTGACTACTGGGGCCAGGGAACCCTGGTCACCGTCTCC |
| 126 | 7004-09hu09 light chain variable region encoding nucleic acid sequence | GACATCGTGATGACCCAGTCTCCAGACTCCCTGGCTGTGTCTCTG GGCGAGAGGGCCACCATCAACTGCAAGTCCAGCCAGAGTCTTTTA AACAGTGGCAACCAGAAGAACTATTTAGCTTGGTACCAGCAGAA ACCAGGACAGCCTCCTAAGTTGCTCATTTACTGGGCATCTACCCG GGAATCCGGGGTCCCTGACCGATTCAGTGGCAGCGGGTCAGGAA CAGACTTCACTCTCACCATCAGCAGCCTGCAGGCTGAAGATGTGG CAGTTTATTACTGTCAGAATGCATATTACTACCCGTTCACTTTTGG CCAGGGGACCAAGCTGGAGATCAAA |
| 127 | 7004-09hu10 heavy chain variable region encoding nucleic acid sequence | CAGGTGCAGCTGGTGCAGTCTGGGGCTGAGGTGAAGAAGCCTGG GGCCTCAGTGAAGGTTTCCTGCAAGGCATCTGGATACACCTTCAC CAGCTACTATATGCACTGGGTGCGACAGGCCCCTGGACAAGGGCT TGAGTGGATGGGAACTATCTATCCTGGTAATGGTGATACAAGCTA CAACCAGAAGTTCCAGGGCAGAGTCACCATGACCAGGGACAAGT CCACGAGCACAGTCTACATGGAGCTGAGCAGCCTGAGATCTGAG GACACGGCCGTGTATTTCTGTGCGAGAGGCGGGTATTATGGGAAC AGTCTTGACTACTGGGGCCAGGGAACCCTGGTCACCGTCTCC |
| 128 | 7004-09hu10 light chain variable region encoding nucleic acid sequence | GACATCGTGATGACCCAGTCTCCAGACTCCCTGGCCGTGTCTCTG GGCGAGAGGGCCACCATCAACTGCAAGTCCAGCCAGAGTCTTTTA AACAGCGGCAACCAGAAGAACTACTTAACTTGGTACCAGCAGAA ACCAGGACAGCCTCCTAAGTTGCTCATTTACTGGGCGTCTACCCG GGAATCCGGGGTCCCTGACCGATTCAGTGGCTCCGGGTCTGGGAC AGATTTCACTCTCACCATCAGCAGCCTGCAGGCTGAAGATGTGGC AGTTTATTACTGTCAAAATGCATACTACTACCCGTTCACTTTTGGC CAGGGGACCAAGCTGGAGATCAAA |

Specific Models for Carrying Out the Present Invention

The invention will now be described with reference to the following examples which are intended to illustrate the invention without limiting it.

Unless otherwise specified, the molecular biology experimental methods and immunoassays used in the present invention can be basically referred from J. Sambrook et al., Molecular Cloning: Laboratory Manual, 2nd Edition, Cold Spring Harbor Laboratory Press, 1989, and F. M. Ausubel et al., Short Protocols in Molecular Biology, 3rd Edition, John Wiley & Sons, Inc., 1995; the use of restriction enzymes was in accordance with conditions recommended by the product manufacturer. Those skilled in the art know that the embodiments describe the present invention by way of examples and are not intended to limit the scope of the invention as claimed.

Example 1: Production of Anti-CLDN18.2 Murine Antibodies

To obtain anti-human CLDN18.2 antibody, mice (Beijing Weitong Lihua Experimental Animal Technology Co., Ltd., strain 216) were vaccinated by different immunization strategies (Table 2) to trigger the generation of murine monoclonal antibodies. The antigens included: an expression plasmid expressing the nucleic acid sequence encoding human CLDN18.2 extracellular domain 1 (CLDN18.2-ECL1 DNA; SEQ ID NO: 83, the vector was pcDNA3.1), an expression plasmid expressing the nucleic acid sequence encoding human CLDN18.2 extracellular domain 1-complement C3 (CLDN18.2-ECL1-C3d DNA; SEQ ID NO: 84, the vector was pcDNA3.1), an expression plasmid expressing the nucleic acid sequence encoding full-length human CLDN18.2 (hCLDN18.2 DNA; SEQ ID NO: 85, the vector was pcDNA3.1), the transfected Chinese hamster ovary cell expressing human CLDN18.2 (CHO-hCLDN18.2), the transfected kidney embryo cell highly expressing human CLDN18.2 (HEK293-hCLDN18.2). The adjuvants included: in vivo-jetPEI (Polyplus Transfection Company, Catalog No. 201-50G), ODN 1826 VacciGrade (InvivoGen Company, Catalog No. vac-1826-1), complete Freund's adjuvant CFA (InvivoGen Company, Catalog No. vac-cfa-60). And the routes of administration included: intramuscular (im), intraperitoneal (ip), and subcutaneous (sc) injections. 3 days after booster immunization, the spleen cells of the immunized mice were fused with murine myeloma cells SP2/0 using the polyethylene glycol method, thereby obtaining the fusion cells that could express antibodies and proliferate indefinitely in vitro, and the fusion cells were cultured in HAT selective medium. The fused hybridoma cells were plated in a 96-well cell culture plate, and positive clones were selected through primary screening and subjected to 2 to 3 rounds of subcloning.

TABLE 2

Immunization protocols used to generate monoclonal antibodies

| Antigen | Dose | Adjuvant | Immune duration | Administration route |
|---|---|---|---|---|
| CLDN18.2-ECL1 DNA | 100 µg for the first time, 50 µg each time thereafter | In vivo-jetPEI | once every 2 weeks, for a total of 3 times | IP |
| CLDN18.2-ECL1 DNA | 100 µg for the first time, 50 µg each time thereafter | In vivo-jetPEI | once every 3 weeks, for a total of 3 times | IP |
| CHO-hCLDN18.2 | 5E6 cells | CFA for the first time, PBS thereafter | once every 2 weeks, for a total of 4 times | sc |
| HEK293-hCLDN18.2 | 5E6 cells | CFA for the first time, PBS thereafter | once every 2 weeks, for a total of 4 times | sc |
| CLDN18.2-ECL1-C3d DNA | 100 µg each time | In vivo-jetPEI & ODN 1826 | once every 2 weeks, for a total of 4 times | IM |

TABLE 2-continued

Immunization protocols used to generate monoclonal antibodies

| Antigen | Dose | Adjuvant | Immune duration | Administration route |
|---|---|---|---|---|
| hCLDN18.2 DNA | 100 µg each time | In vivo-jetPEI & ODN 1826 | once every 2 weeks, for a total of 4 times | IM |

Primary screening: In the primary screening, the supernatant of growing clones was tested for its ability to bind to CLDN18.2 on the surface of cells by using the cells expressing human CLDN18.2. The presence of reactive antibodies in the supernatant was detected by using a secondary antibody DyLight488 goat anti-mouse IgG (Abcam, Catalog No. ab97015), and the binding capacity was evaluated on a full-field scanning cytometer (see Example 3).

Secondary screening: The supernatant of fused clone which bound to human CLDN18.2, was tested for its ability to bind to CLDN18.1 on the surface of cells by using the human CLDN18-expressing cells. The presence of reactive antibodies in the supernatant was detected by using a secondary antibody DyLight488 goat anti-mouse IgG (Abcam, Catalog No. ab97015), and the binding capacity was evaluated on a full-field scanning cytometer (for detailed experimental steps, see the Examples 3). Finally, 10 positive monoclonal hybridoma cell strains were obtained, and the following antibodies were isolated and purified from the culture supernatant: 1D10, 2F12, 3F2, 5F9, 9F3, 10B11, 27B5, 37B1, 44A8, 44F7.

Example 2: Evaluation of Antigen-Binding Activity of Anti-CLDN18.2 Murine Antibodies 2.1 Construction of Cell Lines Expressing CLDN18.2

Human CLDN18.2 (SEQ ID NO: 86) or CLDN18.1 (SEQ ID NO: 88), or murine CLDN18.2 (SEQ ID NO: 87) was over-expressed in HEK293T cells (ATCC), CHOS cells (Invitrogen), OCUM-1 gastric cancer tumor cells (Nanjing Kebai Biotechnology Co., Ltd.), by using the method of lentivirus infection and antibiotic resistance screening (MOI=3 to 10, 5 µg/ml polybrene). The lentivirus was provided by Shanghai Genechem Co., Ltd. After 72 hours of cell infection, the corresponding antibiotic was applied and culture was continued for 2 to 4 weeks, followed by expansion and cryopreservation for subsequent experiments.

2.2 Detection of the Binding of Mouse Antibodies to CLDN18.2 and CLDN18.1 on Cell Surface by Cell Scanning Cytometer HEK293T-hCLDN18.2 and OCUM-1-hCLDN18.2 expressing human CLDN18.2 (hCLDN18.2), or HEK293T-mCLDN18.2 expressing mouse CLDN18.2 (mCLDN18.2) and the corresponding negative control cell line HEK293T were used; or HEK293T-hCLDN18.1 and CHOS-hCLDN18.1 expressing human CLDN18.1 (hCLDN18.1) were used. DyLight488 goat anti-mouse IgG (Abcam, Catalog No. ab97015) or DyLight488 goat anti-human IgG (Abcam, Catalog No. ab97003) was used as secondary antibody. Binding curves were generated by using the following method.

10,000 cells were plated in 100 µL of DMEM containing 10% FBS per well in a flat-bottomed 96-well plate. After the cells adhered or were settled to the bottom of the wells overnight, the supernatant was removed on the next day. 3-Fold gradient dilution of antibody was performed by diluting ⅓ of the total volume (i.e., 100 µL) in 200 µL of DMEM. 100 μL of the diluted antibody (the supernatants of fused clones or subclones was used in the screening) was added to each well of the cell plate, 100 μL of DMEM was added to the corresponding negative control well, and incubation was carried out for 1 hour at room temperature. After removing the supernatant, 100 μL of secondary antibody (5 μg/mL, diluted in DMEM) was added to each well, and incubated at room temperature for 0.5 hours. The supernatant was removed after staining, followed by washing with PBS once. 100 μL of PBS was added to each well, and then reading was carried out on the cytometer.

A full-field scanning cytometer (Nexcelom, Celigo® Image Cytometer) was used to measure the readings of the experimental plate. During the measurement, high-speed scanning imaging of the cells in the well was simultaneously performed in the green fluorescent channel corresponding to the secondary antibody and in the bright field channel. The cells that bound the antibody were counted in the image obtained from the green fluorescent channel under the parameters set in accordance with the morphology and fluorescence intensity of the fluorescently labeled cells, and the adhered cells were counted in the image obtained from the bright field channel under the parameters set in accordance with the morphology of the cells. And the percentage of the antibody-binding cells with green fluorescence in the total number of adhered cells (% fluorescent cells) was obtained by dividing the counting result obtained from green fluorescent channel by the counting result obtained from bright field channel. The binding activity of anti-CLDN18.2 antibody to CLDN18.2-expressing cells was determined according to this percentage, that was, the lower the percentage, the poorer the ability of anti-CLDN18.2 antibody to bind to CLDN18.2 on cell surface; conversely, the higher the percentage, the better the ability of anti-CLDN18.2 antibody to bind to CLDN18.2 on cell surface. The data analysis was performed using GraphPad.

The results of measuring the binding activities of anti-CLDN18.2 antibody to HEK293T expressing human CLDN18.2, HEK293T expressing murine CLDN18.2, HEK293T expressing human CLDN18.1, and control HEK293T were shown in FIGS. 1A to 1D, in which the abscissa indicated the logarithm of antibody concentration, the ordinate indicated the percentage of the CLDN18.2 antibody-binding cells with green fluorescence in the total number of adhered cells. The EC50 of the antigen-binding activity of the anti-CLDN18.2 antibody was further obtained from the fitted curves, and the results were shown in Table 3, in which the reference antibody was 175D10 (Ganymed Pharmaceuticals AG), which was disclosed in, for example, CN101312989B and CN103509114B.

TABLE 3

| Measurement results of binding activity of anti-CLDN18.2 antibody to CLDN18.2. | | | | |
| | EC50 (μg/ml) | | | |
| Antibody | HEK293-hCLDNA18.2 | HEK293-mCLDN18.2 | OCUM1-hCLDN18.2 | HEK293 |
| 1D10 | 0.018 | 0.691 | 0.026 | N.B. |
| 2F12 | 0.041 | 0.036 | 0.186 | N.B. |
| 3F2 | 0.034 | 0.059 | 0.121 | N.B. |
| 5F9 | 0.091 | 0.179 | 0.068 | N.B. |
| 9F3 | 0.053 | 0.043 | 0.150 | N.B. |
| 10B11 | 0.038 | 0.035 | 0.135 | N.B. |
| 27B5 | 0.041 | 0.033 | 0.142 | N.B. |
| 37B1 | 0.040 | 0.032 | 0.146 | N.B. |

TABLE 3-continued

| Measurement results of binding activity of anti-CLDN18.2 antibody to CLDN18.2. | | | | |
| | EC50 (μg/ml) | | | |
| Antibody | HEK293-hCLDNA18.2 | HEK293-mCLDN18.2 | OCUM1-hCLDN18.2 | HEK293 |
| 44A8 | 0.034 | 0.026 | 0.097 | N.B. |
| 44F7 | 0.028 | 0.026 | 0.092 | N.B. |
| 175D10 | 1.22 | 0.81 | 6.54 | N.B. |

Note:
N.B. indicated that there was no binding within the range of the measured concentration.

The above results showed that 1D10, 2F12, 3F2, 5F9, 9F3, 10B11, 27B5, 37B1, 44A8 and 44F7 all could bind to cells expressing human CLDN18.2, and were significantly better than the reference antibody 175D10, and these antibodies did not bind to the negative control cells (HEK293T) that did not express CLDN18.2.

The EC50 values of the binding activity of anti-CLDN18.2 antibody to CLDN18.1 were shown in Table 4. The results showed that none of 2F12, 3F2, 9F3, 10B11, 27B5, 37B1, 44A8 and 44F7 bound to CLDN18.1, showing good binding specificity to CLDN18.2.

TABLE 4

| Measurement results of binding activity of anti-CLDN18.2 antibody to CLDN18.1 | | |
| | EC50 μg/ml | |
| Antibody | CHOS-hCLDN18.1 | HEK293-hCLDN18.1 |
| 1D10 | 0.092 | 0.041 |
| 2F12 | N.B. | N.B. |
| 3F2 | | N.B. |
| 5F9 | | 0.714 |
| 9F3 | N.B. | N.B. |
| 10B11 | N.B. | N.B. |
| 27B5 | N.B. | N.B. |
| 37B1 | N.B. | N.B. |
| 44A8 | N.B. | N.B. |
| 44F7 | N.B. | N.B. |
| 175D10 | N.B. | N.B. |

Note:
N.B. indicated that there was no binding within the range of the measured concentration, and blank indicated that the antibody was not measured for this data.

Example 3: Sequence Determination of Anti-CLDN18.2 Murine Antibody and Preparation of Chimeric Antibody 3.1 Determination of Variable Region Sequence of Anti-Human CLDN18.2 Murine Antibody Hybridoma cells were collected by centrifugation, and $5$-$10 \times 10^6$ cells were added with 1 ml of TRIzol and 0.2 ml of chloroform, shaken vigorously for 15 seconds, followed by incubating at room temperature for 3 minutes. After centrifugation, the aqueous phase was collected and added with 0.5 ml of isopropanol, followed by incubating for 10 minutes at room temperature. The precipitate was collected and washed with ethanol and dried to obtain RNA. Template RNA and primers were added to ice-bath centrifuge tube; reverse transcription was carried out when the primers and the template were correctly paired, followed by PCR amplification. After the amplification was completed, 4 microcentrifuge tubes were each added with 2.5 μl of dNTP/ddNTP mixture, and incubated at 37° C. for 5 minutes for later use.

In an empty microcentrifuge tube, 1 pmol of the PCR amplification product, 10 pmol of sequencing primer, 2 μl of 5× sequencing buffer were added, and double distilled water was added to a total volume of 10 μl, then subjected to heating at 96° C. for 8 minutes, ice bath for 1 minute, and centrifugation at 4° C. and 10000 g for 10 seconds. 2 μl of precooled label mixture (0.75 mol/L each for dCTP, dGTP and dTTP), α-32P-dATP 5 μCi, 1 μl of 0.1 mol/L DDT, 2U of sequencing enzyme were added, water was then added to reach 15 μl, mixed well and placed on ice for 2 minutes. 3.5 μl of the labeling reaction mixture was added to the 4 prepared microcentrifuge tubes, and incubated at 37° C. for 5 minutes. 4 μl of stop solution was added to each tube. The samples were thermally denatured in water bath at 80° C. for 5 minutes, loaded on each lane of sequencing gel at an amount of 2 μl, and these fragments were separated by electrophoresis to collect sequence information.

The VH and VL sequences of the 10 mouse antibodies were shown in Table 5 below. And the CDR sequences of the 10 murine monoclonal antibodies (Table 6) were further determined by the method described by Kabat et al. (Kabat et al., Sequences of Proteins of Immunological Interest, Fifth Edition, Public Health Service, National Institutes of Health, Bethesda, Maryland (1991), pp. 647-669).

TABLE 5

Amino acid sequences of light and heavy chain variable regions of murine antibodies

| Antibody | VH SEQ ID NO | VL SEQ ID NO |
|---|---|---|
| ID10 | 1 | 2 |
| 2F12 | 9 | 10 |
| 3F2 | 17 | 18 |
| 5F9 | 25 | 26 |
| 9F3 | 33 | 34 |
| 10B11 | 41 | 42 |
| 27B5 | 49 | 50 |
| 37B1 | 57 | 58 |
| 44A8 | 65 | 66 |
| 44F7 | 73 | 74 |

TABLE 6

CDR sequences of murine antibodies

| Antibody | VH (SEQ ID NO:) CDR1 | CDR2 | CDR3 | VL (SEQ ID NO:) CDR1 | CDR2 | CDR3 |
|---|---|---|---|---|---|---|
| ID10 | 3 | 4 | 5 | 6 | 7 | 8 |
| 2F12 | 11 | 12 | 13 | 14 | 15 | 16 |
| 3F2 | 19 | 20 | 21 | 22 | 23 | 24 |
| 5F9 | 27 | 28 | 29 | 30 | 31 | 32 |
| 9F3 | 35 | 36 | 37 | 38 | 39 | 40 |
| 10B11 | 43 | 44 | 45 | 46 | 47 | 48 |
| 27B5 | 51 | 52 | 53 | 54 | 55 | 56 |
| 37B1 | 59 | 60 | 61 | 62 | 63 | 64 |
| 44A8 | 67 | 68 | 69 | 70 | 71 | 72 |
| 44F7 | 75 | 76 | 77 | 78 | 79 | 80 |

Figure 2:
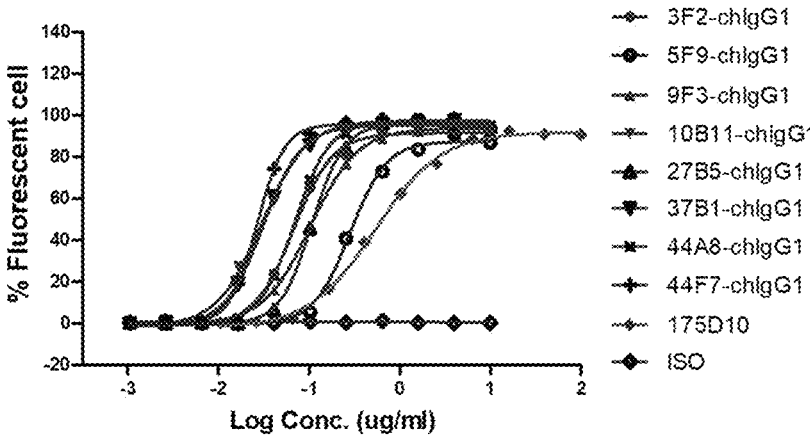
FIG. 2 shows the results of measuring the binding activity of anti-CLDN18.2 chimeric antibody to cell surface CLDN18.2.

3.2 Preparation of Human-Mouse Chimeric Antibodies and Evaluation of Antigen-Binding Activity The gene sequences (see SEQ TD NOs: 103-122) encoding the heavy chain and light chain variable regions of the above-mentioned mouse antibodies were ligated to the sequences encoding the heavy chain constant region (SEQ ID NO: 81) and the light chain constant region (SEQ TD NO: 82) of the human antibody, respectively, and were recombinantly expressed in HEK293 cells (ATCC), thereby obtaining the corresponding chimeric antibodies 1D10-chIgG1, 2F12-chIgG1, 3F2-chIgG1, 5F9-chIgG1, 9F3-chIgG1, 10B11-chIgG1, 27B5-chIgG1, 37B1-chIgG1, 44A8-chIgG1, 44F7-chIgG1. The binding activity of the chimeric antibodies of different concentrations to HEK293T cells expressing human CLDN18.2 (HEK293T-hCLDN18.2) was detected by the method described in Example 2. The results were shown in FIG. 2, in which the abscissa indicated the logarithm of antibody concentration, and the ordinate indicated the percentage of the CLDN18.2 antibody-binding cells with green fluorescence in the total number of adhered cells (% fluorescent cells). EC50 values of the binding activity of chimeric antibodies to antigen were further obtained from the fitted curves, and were shown in Table 7. The results showed that the chimeric antibodies 3F2-chIgG1, 5F9-chIgG1, 9F3-chIgG1, 10B11-chIgG1, 27B5-chIgG1, 37B1-chIgG1, 44A8-chIgG1 and 44F7-chIgG1 all could recognize/bind human CLDN18.2.

TABLE 7

Measurement results of binding activity of chimeric antibodies to CLDN18.2.

| Antibody | EC50 (μg/ml) HEK293-hCLDNA18.2 |
|---|---|
| 3F2-chIgG1 | 0.068 |
| 5F9-chIgG1 | 0.283 |
| 9F3-chIgG1 | 0.104 |
| 10B11-chIgG1 | 0.030 |
| 27B5-chIgG1 | 0.108 |
| 37B1-chIgG1 | 0.031 |
| 44A8-chIgG1 | 0.069 |
| 44F7-chIgG1 | 0.027 |
| 175D10 | 0.536 |

Example 4: Evaluation of the Activity of Anti-CLDN18.2 Chimeric Antibody to Induce ADCC HEK293T-hCLDN18.2 or human gastric cancer tumor cell lines KATO-III and NUGC4 that naturally express hCLDN18.2, were used as target cells; and human peripheral blood mononuclear cells (PBMC) isolated by Ficoll were used as effector cells. The target cells were harvested and washed twice with PBS. The live-cell dye Calcein AM (50 μg of Calcein AM dry powder (Life Technologies, Cat #C3100MP) was dissolved in 50 μl of DMSO) was diluted to 3 μM, and the target cells were stained under 5% $CO_2$ at 37° C. for 30 minutes. After staining, the cells were washed twice with PBS, and 5000 target cells were plated in 100 μL of DMEM per well in a flat-bottomed 96-well plate. 3-Fold gradient dilution of tested antibody was performed by diluting ⅓ of the total volume (i.e., 100 μL) in 200 μL of DMEM. 50 μL of the diluted antibody was added to the corresponding wells of the cell plate (50 μL of DMEM medium was added to the control wells for non-specific killing), and was incubated with the target cells under 5% $CO_2$ at 37° C. for 30 minutes. 50000 isolated PBMCs in 50 μL were then added to each well as effector cells, followed by centrifugation at 1000 rpm for 3 minutes to allow the cells to settle to the bottom of the plate. The experimental plate was measured for readings in a full-field scanning cytometer (Nexcelom, Celigo® Image Cytometer) at multiple time points (0 hour, 2 hours, 3 hours, 4 hours, and 6 hours). During the measurement, high-speed scanning imaging of the cells in the well was simultaneously performed in the green fluorescent channel corresponding to Calcein AM and in the bright field channel. Live cells in each well were counted in the image obtained from the green fluorescent channel under the parameters set in accordance with the morphology and fluorescence intensity of the fluorescently labeled cells, and the total cells in each well were counted in the image obtained from the bright field channel under the parameters set in accordance with the morphology of the cells. And the percentage of live cells with green fluorescence in the total number of cells was obtained by dividing the counting result obtained from green fluorescent channel by the counting result obtained from bright field channel. The percentage of the cells which had undergone specific cell lysis in the presence of the antibody in the total number of cells was obtained by subtracting the corresponding percentage obtained in the presence of the antibody from the percentage of the non-specific control well. The activity of anti-CLDN18.2 antibody to induce ADCC was determined based on this percentage value; that was, the lower the percentage, the lower the ability of anti-CLDN18.2 antibody to induce ADCC; conversely, the higher the percentage, the better the ability of anti-CLDN18.2 antibody to induce ADCC. The data analysis was performed using GraphPad.

Figure 3A:
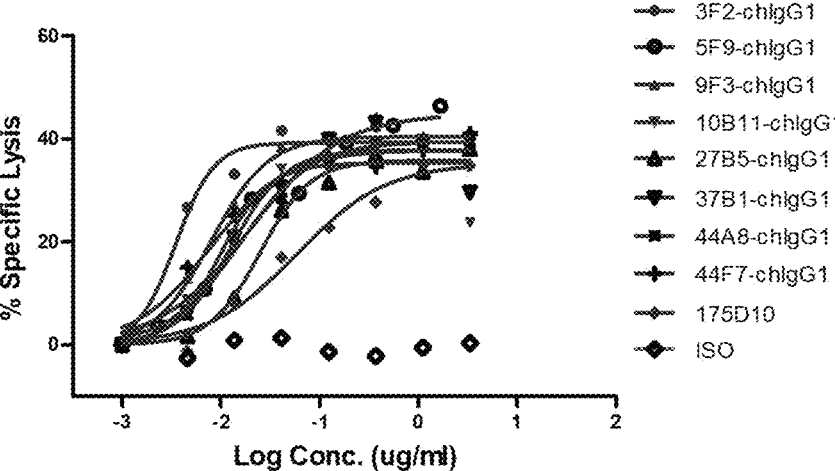
FIGS. 3A to 3C show the results of measuring the ADCC activity of anti-CLDN18.2 chimeric antibody to HEK293T-hCLDN18.2, KATO-III, and NUGC4, respectively.
Figure 3B:
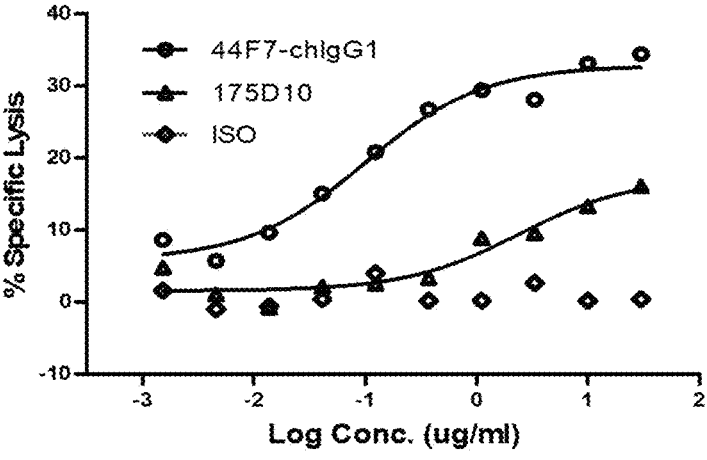
Figure 3C:
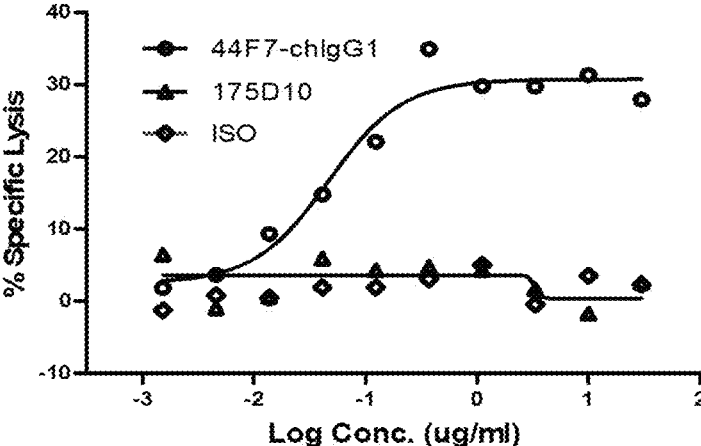

The measurement results of activity of anti-CLDN18.2 antibody to induce ADCC were shown in FIGS. 3A to 3C, in which the abscissa indicated the logarithm of antibody concentration and the ordinate indicated the corrected percentage of specific lysis. EC50 of the activity of the anti-CLDN18.2 chimeric antibody to induce ADCC was further obtained from the fitted curves, and the results were shown in Table 8. The results showed that the tested antibodies could induce the killing effect of PBMC on cells expressing human CLDN18.2, which were significantly better than the reference antibody 175D10.

TABLE 8

| Measurement results of activity of chimeric antibody to induce ADCC | | | |
|---|---|---|---|
| | ADCC EC50 µg/ml | | |
| Antibody | HEK293T-hCLDN18.2 | KATO-III | NUGC4 |
| 3F2-chIgG1 | 0.0035 | | |
| 5F9-chIgG1 | 0.0197 | | |
| 9F3-chIgG1 | 0.0080 | | |
| 10B11-chIgG1 | 0.0010 | | |
| 27B5-chIgG1 | 0.0249 | | |
| 37B1-chIgG1 | 0.0126 | | |
| 44A8-chIgG1 | 0.0156 | | |
| 44F7-chIgG1 | 0.0078 | 0.099 | 0.047 |
| 175D10 | 0.0580 | 2.396 | N.A. |

Note:
N.A. indicated that EC50 exceeded the concentration range as measured, and blank indicated that the antibody had not been measured for this data.

Example 5: Evaluation of Activity of Anti-CLDN18.2 Chimeric Antibody to Induce CDC HEK293T-hCLDN18.2 or human gastric cancer tumor cell line KATO-III that naturally expressed hCLDN18.2, was used as target cells; and fresh human serum was used as effector cells. The target cells were harvested and washed twice with PBS. The live-cell dye Calcein AM (50 g of Calcein AM dry powder (Life Technologies, Cat #C3100MP) was dissolved in 50 µl of DMSO) was diluted to 3 µM, and the target cells were stained under 5% $CO_2$ at 37° C. for 30 minutes. After staining, the cells were washed twice with PBS, and 8,000 target cells were plated in 25 µL of DMEM per well in a flat-bottomed 96-well plate. 3-Fold gradient dilution of tested antibody was performed by diluting ⅓ of the total volume (i.e., 100 µL) in 200 µL of DMEM. 25 µL of the diluted antibody was added to each well of the cell plate (25 µL of DMEM medium was added to control well for non-specific killing), and incubated with target cells under 5% $CO_2$ at 37° C. for 30 minutes. 50 µL of freshly isolated 20% human serum (diluted with DMEM) as effector cells was then added to each well, followed by centrifugation at 1000 rpm for 3 minutes to allow the cells to settle to the bottom of the plate. The experimental plate was measured for readings in a full-field scanning cytometer (Nexcelom, Celigo® Image Cytometer) at multiple time points (0, 1, 2, 3, and 4 hours). During the measurement, high-speed scanning imaging of the cells in the well was simultaneously performed in the green fluorescent channel corresponding to Calcein AM and in the bright field channel. Live cells in each well were counted in the image obtained from the green fluorescent channel under the parameters set in accordance with the morphology and fluorescence intensity of the fluorescently labeled cells, and the total cells in each well were counted in the image obtained from the bright field channel under the parameters set in accordance with the morphology of the cells. And the percentage of live cells with green fluorescence in the total number of cells was obtained by dividing the counting result obtained from green fluorescent channel by the counting result obtained from bright field channel. The percentage of the cells which had undergone specific cell killing in the presence of the antibody in the total number of cells was obtained by subtracting the corresponding percentage obtained in the presence of the antibody from the percentage of the non-specific control well. The activity of anti-CLDN18.2 antibody to induce CDC was determined based on this percentage value; that was, the lower the percentage, the lower the ability of anti-CLDN18.2 antibody to induce CDC; conversely, the higher the percentage, the better the ability of anti-CLDN18.2 antibody to induce CDC. The data analysis was performed using GraphPad.

Figure 4A:
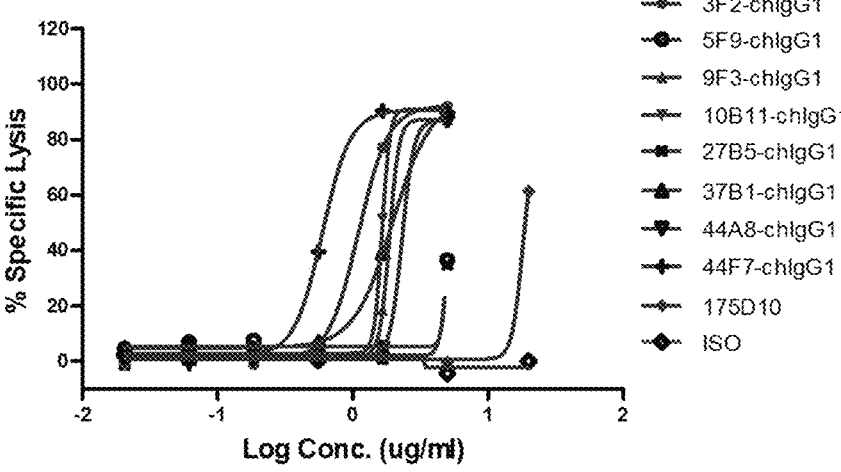
FIGS. 4A to 4B show the results of measuring the CDC activity of anti-CLDN18.2 chimeric antibody to HEK293T-hCLDN18.2 and KATO-III, respectively.
Figure 4B:
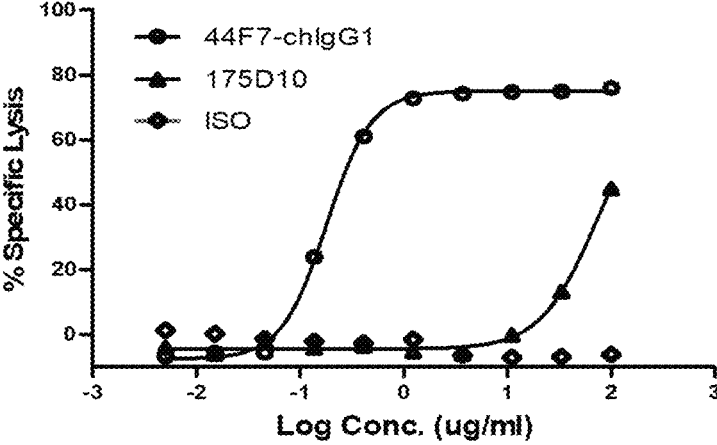

The measurement results of activity of anti-CLDN18.2 antibody to induce CDC were shown in FIGS. 4A to 4B, in which the abscissa indicated the logarithm of antibody concentration and the ordinate indicated the corrected percentage of specific cell killing. EC50 of anti-CLDN18.2 antibody to induce CDC was further obtained from the fitted curves, and the results were shown in Table 9. The results showed that the tested antibodies could induce the killing effect of complement in human serum on cells expressing human CLDN18.2, which were significantly better than the reference antibody 175D10.

TABLE 9

| Measurement results of activity of chimeric antibody to induce CDC | | |
|---|---|---|
| | CDC EC50 µg/ml | |
| Antibody | HEK293T-hCLDN18.2 | KATO-III |
| 3F2-chIgG1 | 1.1 | |
| 5F9-chIgG1 | 5.25 | |
| 9F3-chIgG1 | 1.86 | |
| 10B11-chIgG1 | 1.65 | |
| 27B5-chIgG1 | 5.17 | |
| 37B1-chIgG1 | 1.93 | |
| 44A8-chIgG1 | 2.40 | |

TABLE 9-continued

| Measurement results of activity of chimeric antibody to induce CDC | | |
| --- | --- | --- |
| | CDC EC50 µg/ml | |
| Antibody | HEK293T-hCLDN18.2 | KATO-III |
| 44F7-chIgG1 | 0.60 | 0.18 |
| 175D10 | 18.18 | 73.05 |

Note:
Blank indicated that this data was not measured for this antibody.

Example 6: Evaluation of Activity of Anti-CLDN18.2 Antibody to Induce CLDN18.2 Internalization In this example, the internalization level of CLDN18.2 on the surface of cell (HEK293T-hCLDN 18.2) mediated by anti-CLDN18.2 antibody was detected by flow cytometry. Two samples of cells were incubated with 10 g/mL chimeric antibody at 37° C. for 1 hour and 4 hours, respectively. After being washed several times with PBS containing 2% FBS, 10 g/mL secondary antibody was added and stained at 4° C. for 30 minutes. The expression level of CLDN18.2 on cell surface was then analyzed by flow cytometry.

$MFI_{4H}$ was the MFI of the sample after 4 hours of incubation, $MFI_{1H}$ was the MFI of the sample after 1 hour of incubation, where it was assumed that the binding of antibody had completed and endocytosis had not yet occurred. $MFI_{background}$ was the MFI of the secondary antibody only. The percentage of antibody-mediated internalization of cell surface CLDN18.2 was calculated by the following formula:

Percentage of internalized $CLDN18.2(\%)=100-100\times(MFI_{4H}-MFI_{1H})/(MFI_{1H}-MVFI_{background})$ The results were shown in Table 10. These antibodies mediated the internalization of CLDN18.2 on the surface of HEK293T-hCLDN18.2 cells at varying degrees.

TABLE 10

| Measurement results of chimeric antibody-induced CLDN 18.2 internalization | |
| --- | --- |
| Antibody | Internalization percentage (%) |
| ID10-chIgG1 | 28.7 |
| 5F9-chIgG1 | 9.3 |
| 27B5-chIgG1 | −2.2 |
| 37B1-chIgG1 | −3.2 |
| 44F7-chIgG1 | −1.5 |
| 44A8-chIgG1 | 2.5 |

Example 7: Humanization of Anti-CLDN18.2 Antibody and Evaluation of the Activity Thereof In order to improve the sequence homology of the candidate antibodies and human antibodies and reduce the immunogenicity of the antibodies to humans, the murine antibodies provided in the above examples could be subjected to design and preparation for humanization, in which murine CDR regions were grafted onto human framework sequences (see U.S. Pat. No. 5,225,539 to Winter; U.S. Pat. Nos. 5,530,101, 5,585,089, 5,693,762 and 6,180,370 to Queen et al; and Lo, Benny, KC, editor, in Antibody Engineering: Methods and Protocols, volume 248, Humana Press, New Jersey, 2004). Typically, all or part of the CDR regions of humanized antibodies were derived from non-human antibodies (donor antibodies), and all or part of the non-CDR regions (e.g., variable region FR and/or constant regions) were derived from human immunoglobulin (receptor antibody).

Based on this, the present inventors prepared and obtained 3 humanized antibodies of murine antibody 44F7, named as 7004-09hu09, 7004-09hu10, and 7004-09hu15, respectively. The amino acid sequences thereof were shown in the table below.

TABLE 11

| Amino acid sequences of light and heavy chain variable regions of humanized antibodies | | | |
| --- | --- | --- | --- |
| Antibody | 7004-09hu09 | 7004-09hu10 SEQ ID NO: | 7004-09hu15 |
| VH | 99 | 101 | 91 |
| HCDR1 | 75 | 75 | 93 |
| HCDR2 | 76 | 76 | 94 |
| HCDR3 | 77 | 77 | 95 |
| VL | 100 | 102 | 92 |
| LCDR1 | 78 | 78 | 96 |
| LCDR2 | 79 | 79 | 97 |
| LCDR3 | 80 | 80 | 98 |

Figure 5:
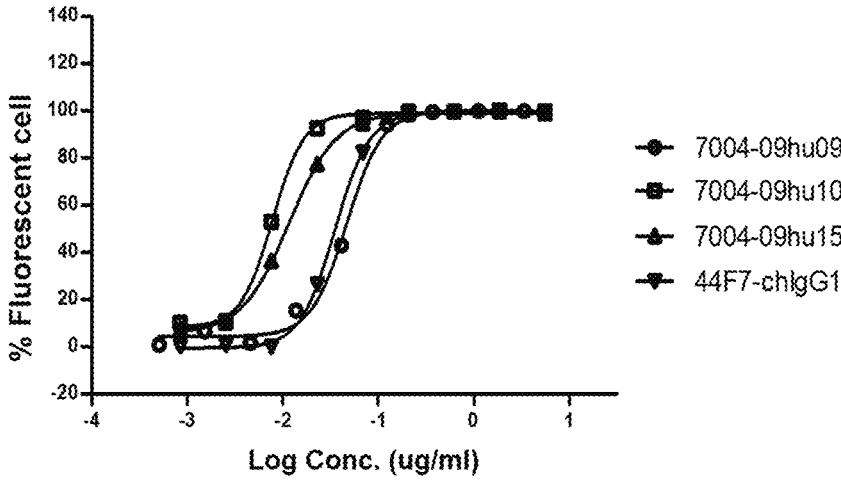
FIG. 5 shows the results of measuring the binding activity of anti-CLDN18.2 humanized antibody to cell surface CLDN18.2.

The gene sequences (see SEQ ID NOs: 123-128) encoding the heavy chain and light chain variable regions of the above-mentioned humanized antibodies were ligated to the sequences encoding heavy chain constant region (SEQ ID NO: 81) and light chain constant region (SEQ ID NO: 82) of human antibody respectively, followed by recombinant expression. The binding ability of the humanized antibodies to CLDN18.2 expressed on the surface of HEK293T-hCLDN18.2 was determined by a cell scanning cytometer and using the method described in Example 2.2. The results were shown in FIG. 5, in which the abscissa indicated the logarithm of antibody concentration, and the ordinate indicated the percentage of CLDN18.2 antibody-binding cells with green fluorescence in the total number of adhered cells (% fluorescent cells). The EC50 of the antigen-binding activity of the anti-CLDN18.2 humanized antibody was further obtained from the fitted curves, and the results were shown in Table 12. The results showed that all the tested humanized antibodies could bind to hCLDN18.2-expressing cells, and the affinity thereof was in the same order of magnitude as that of the parental chimeric antibody.

TABLE 12

| Measurement results of binding activity of humanized antibodies to CLDN18.2. | |
| --- | --- |
| Antibody | EC50 (µg/ml) HEK293-hCLDNA18.2 |
| 7004-09hu09 | 0.051 |
| 7004-09hu10 | 0.047 |
| 7004-09hu15 | 0.008 |
| 44F7-chIgG1 | 0.012 |
| 175D10 | 0.035 |

Figure 6:
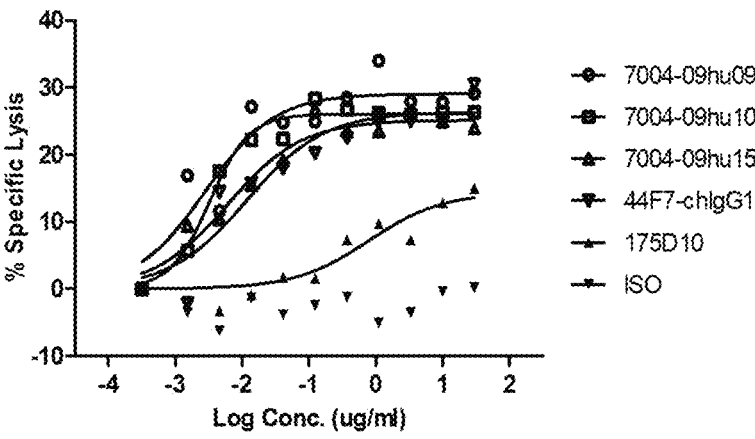
FIG. 6 shows the results of measuring the ADCC activity of anti-CLDN18.2 humanized antibody to KATO-III.

Further, the present inventors investigated the ability of humanized antibodies to induce ADCC, and the evaluation method referred to that described in Example 4. Human gastric cancer tumor cells KATO-III were used as the target cells, and human peripheral blood mononuclear cells isolated by Ficoll were used as the effector cells. The measurement results were shown in FIG. 6, in which the abscissa indicated the logarithm of antibody concentration and the ordinate indicated the corrected percentage of specific cell lysis. The EC50 of the activity of the anti-CLDN18.2 chimeric antibody to induce ADCC was further obtained from the fitted curves, and the results were shown in Table 13. The results showed that all the tested antibodies could induce the killing effect of PBMC on cells expressing human CLDN18.2, and their ability to induce ADCC was in the same order of magnitude as that of the parental chimeric antibody, and was significantly better than that of the reference antibody 175D10.

TABLE 13

| Measurement results of activity of humanized antibodies to induce ADCC | |
| --- | --- |
| Antibody | EC50 (µg/ml) KATO-III |
| 7004-09hu09 | 0.0028 |
| 7004-09hu10 | 0.0033 |
| 7004-09hu15 | 0.0061 |
| 44F7-chIgG1 | 0.0117 |
| 175D10 | 0.7884 |

Figure 7:
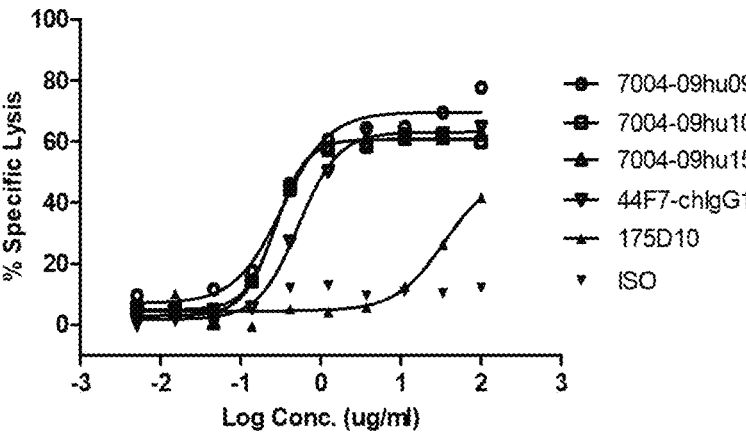
FIG. 7 shows the results of measuring the CDC activity of anti-CLDN18.2 humanized antibody to KATO-III.

The present inventors also investigated the ability of humanized antibodies to induce CDC, and the evaluation method referred to that of Example 5. Human gastric cancer tumor cells KATO-III was used as the target cells, and fresh human serum was used as the effector cells. The measurement results were shown in FIG. 7, in which the abscissa indicated the logarithm of antibody concentration and the ordinate indicated the corrected percentage of specific cell killing. EC50 of the activity of the anti-CLDN18.2 chimeric antibody to induce CDC was further obtained from the fitted curves, and the results were shown in Table 14. The results showed that all the tested antibodies could induce the killing effect of complement in human serum on cells expressing human CLDN18.2, and its ability to induce CDC was in the same order of magnitude as that of the parent chimeric antibody, and was significantly better than that of the reference antibody 175D10.

TABLE 14

| Measurement results of activity of humanized antibodies to induce CDC | |
| --- | --- |
| Antibody | EC50 (µg/ml) KATO-III |
| 7004-09hu09 | 0.33 |
| 7004-09hu10 | 0.27 |

TABLE 14-continued

| Measurement results of activity of humanized antibodies to induce CDC | |
| --- | --- |
| Antibody | EC50 (µg/ml) KATO-III |
| 7004-09hu15 | 0.27 |
| 44F7-chIgG1 | 0.52 |
| 175D10 | 34.83 |

The above results indicated that the humanized antibodies of the present invention not only had a high degree of humanization and thus reduce the possibility of immune rejection, but also exhibited an antitumor activity which was comparable to that of their parent chimeric antibody and better than that of known antibodies.

Figure 8A:
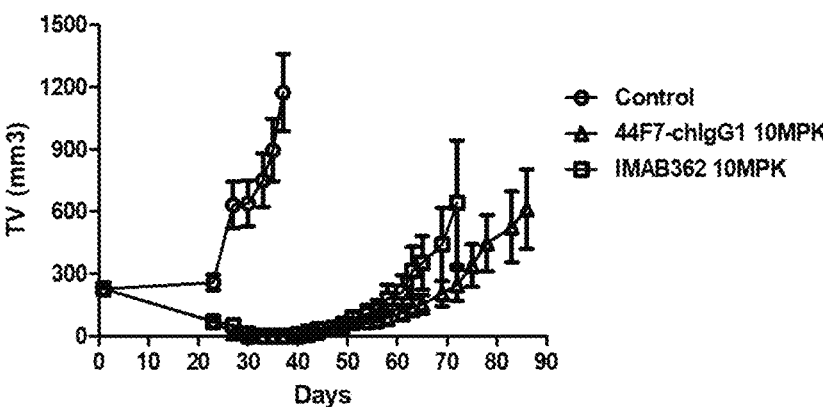
FIGS. 8A to 8B show the effects of anti-CLDN18.2 antibody on tumor volume (A) and survival time (B) in mouse tumor models, respectively.
Figure 8B:
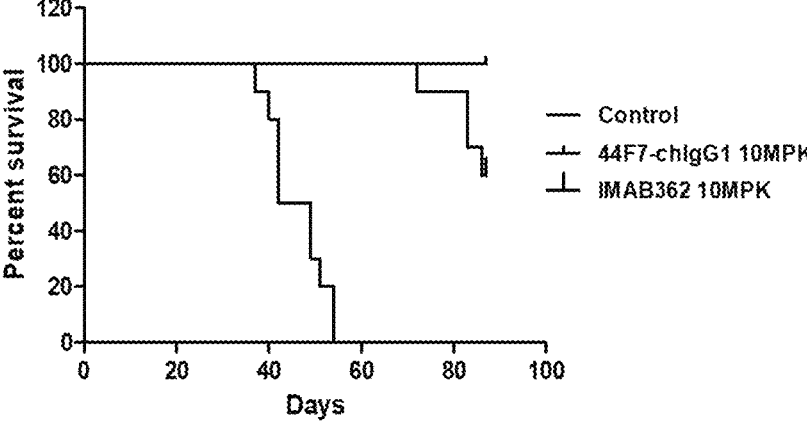

Example 8: Evaluation of In Vivo Antitumor Activity of Anti-CLDN18.2 Chimeric Antibody In order to investigate the antitumor effect of anti-CLDN18.2 antibody in animals, nude mice (SCID, Beijing Weitonglihua Experimental Animal Technology Co., Ltd.) were subcutaneously inoculated with $1 \times 10^7$ HEK293T-hCLDN18.2 cells. Intravenous administration and intraperitoneal administration were alternated starting from the day of inoculation, twice a week for 4 weeks, 10 mg/kg per time. Detection of tumor size in the mice were continued after the end of administration. FIG. 8A showed the change in tumor volume in mice after treatment. The results showed that 44F7-chIgG1 antibody treatment not only significantly inhibited tumor growth, but also completely eliminated tumors in the mice of the administration group, and its antitumor effect was significantly better than that of the reference antibody 175D10. In addition, FIG. 8B showed that 44F7-chIgG1 significantly prolonged the overall survival time of the tumor-bearing mice, demonstrating excellent antitumor activity. It could be seen that, compared with the reference antibody 175D10, 44F7-chIgG1 also showed a significant advantage in prolonging survival time. Such technical effects were significant and unexpected.

Although the specific embodiments of the present invention have been described in detail, those skilled in the art will understand that according to all the teachings that have been published, various modifications and changes can be made to the details, and these changes are all within the protection scope of the present invention. The entirety of the present invention is given by the appended claims and any equivalents thereof.

The invention claimed is:

1. An antibody or antigen-binding fragment thereof which specifically binds to CLDN18.2, wherein the antibody and the antigen-binding fragment thereof comprises a heavy chain variable region (VH) comprising a VH complementarity determining region 1 (CDR1) comprising the amino acid sequence of SEQ ID NO: 75, a VH CDR2 comprising the amino acid sequence of SEQ ID NO: 76, a VH CDR3 comprising the amino acid sequence of SEQ ID NO: 77 and a light chain variable region (VL) comprising a VL CDR1 comprising an amino acid sequence selected from SEQ ID NO: 78 or SEQ ID NO: 96, a VL CDR2 comprising the amino acid sequence of SEQ ID NO: 79, and a VL CDR3 comprising the amino acid sequence of SEQ ID NO: 80.

2. The antibody or the antigen-binding fragment thereof according to claim 1, wherein the antibody and the antigen-binding fragment thereof comprises a heavy chain variable region (VH) and a light chain variable region (VL) selected from the group consisting of:

(1) a VH comprising the amino acid sequence of SEQ ID NO: 73 and a VL comprising the amino acid sequence of SEQ ID NO: 74;

(2) a VH comprising the amino acid sequence of SEQ ID NO: 91 and a VL comprising the amino acid sequence of SEQ ID NO: 92;

(3) a VH comprising the amino acid sequence of SEQ ID NO: 99 and a VL comprising the amino acid sequence of SEQ ID NO: 100; and (4) a VH comprising the amino acid sequence of SEQ ID NO: 101 and a VL comprising the amino acid sequence of SEQ ID NO: 102.

3. The antibody or the antigen-binding fragment thereof according to claim 1, wherein the antibody and the antigen-binding fragment thereof further comprise:

(a) a heavy chain constant region (CH) of a human immunoglobulin; and (b) a light chain constant region (CL) of a human immunoglobulin.

4. The antibody or the antigen-binding fragment thereof according to claim 1, wherein;

(a) the antigen-binding fragment is selected from the group consisting of a fragment antigen-binding region (Fab), a Fab', a (Fab')$_2$, a fragment variable (Fv), a disulfide-linked Fv, a single-chain variable fragment (scFv), and a diabody; or (b) the antibody is a murine antibody, a chimeric antibody, a humanized antibody, a bispecific antibody, or a multispecific antibody.

5. The antibody or the antigen-binding fragment thereof according to claim 1, wherein the antibody and the antigen-binding fragment thereof is labeled with a detectable label selected from the group consisting of an enzyme, a radionuclide, a fluorescent dye, a luminescent substance, and a biotin.

6. An isolated nucleic acid molecule encoding the antibody or the antigen-binding fragment thereof according to claim 1.

7. A vector comprising the isolated nucleic acid molecule according to claim 6.

8. A host cell comprising:

(i) the isolated nucleic acid molecule according to claim 6; or (ii) a vector comprising the isolated nucleic acid molecule according to claim 6.

9. A method for preparing the antibody or the antigen-binding fragment thereof according to claim 1, comprising culturing a host cell comprising an isolated nucleic acid molecule encoding the antibody or the antigen-binding fragment thereof under a condition allowing the expression of the nucleic acid molecule to produce the antibody or the antigen-binding fragment thereof, and recovering the antibody or the antigen-binding fragment thereof from a culture of the cultured host cell.

10. A bispecific or multispecific molecule comprising the antibody or the antigen-binding fragment thereof according to claim 1.

11. An immunoconjugate comprising the antibody or the antigen-binding fragment thereof according to claim 1 and a therapeutic agent linked to the antibody or the antigen-binding fragment thereof.

12. A pharmaceutical composition comprising one or more of a pharmaceutically acceptable carrier or an excipient and one of the following:

(i) the antibody or the antigen-binding fragment thereof according to claim 1, or (ii) a bispecific or multispecific molecule comprising the antibody or the antigen-binding fragment thereof according to claim 1, or (iii) an immunoconjugate, comprising the antibody or the antigen-binding fragment thereof according to claim 1 and a therapeutic agent linked to the antibody or the antigen-binding fragment thereof.

13. A kit comprising the antibody or the antigen-binding fragment thereof according to claim 1.

14. A chimeric antigen receptor comprising an antigen-binding domain of the antibody or the antigen-binding fragment thereof according to claim 1.

15. An isolated nucleic acid molecule encoding the chimeric antigen receptor according to claim 3.

16. A vector comprising an isolated nucleic acid molecule encoding the chimeric antigen receptor according to claim 14.

17. A host cell comprising:

(i) an isolated nucleic acid molecule encoding the chimeric antigen receptor according to claim 14; or (ii) a vector comprising the isolated nucleic acid molecule encoding the chimeric antigen receptor according to claim 14.

18. A method of inhibiting growth of a tumor cell expressing CLDN 18.2 or killing the tumor cell expressing CLDN 18.2, said method comprising contacting the tumor cell with an effective amount of one or more of the following:

(i) the antibody or the antigen-binding fragment thereof according to claim 1, or (ii) a bispecific or multispecific molecule comprising the antibody or the antigen-binding fragment thereof according to claim 1, or (iii) an immunoconjugate comprising the antibody or the antigen-binding fragment thereof according to claim 1 and a therapeutic agent linked to the antibody or the antigen-binding fragment thereof, or (iv) a pharmaceutical composition comprising the antibody or the antigen-binding fragment thereof of (i), the bispecific or multispecific molecule of (ii) or the immunoconjugate of (iii), or (v) a chimeric antigen receptor comprising an antigen-binding domain of the antibody or the antigen-binding fragment thereof according to claim 1, or (vi) an isolated nucleic acid molecule encoding the chimeric antigen receptor of (v), or (vii) a vector comprising an isolated nucleic acid molecule encoding the chimeric antigen receptor of (v), or (viii) a host cell comprising an isolated nucleic acid molecule encoding the chimeric antigen receptor of (v);

wherein the growth of the tumor cell expressing CLDN 18.2 is inhibited; or wherein the tumor cell expressing CLDN 18.2 is killed; and wherein the tumor cell is a gastric cancer cell.

19. A method for preventing and/or treating a tumor in a subject in need thereof, said method comprising administering to the subject an effective amount of one or more of the following:

(i) the antibody or the antigen-binding fragment thereof according to claim 1, or (ii) a bispecific or multispecific molecule comprising the antibody or the antigen-binding fragment thereof according to claim 1, or (iii) an immunoconjugate comprising the antibody or the antigen-binding fragment thereof according to claim 1 and a therapeutic agent linked to the antibody or the antigen-binding fragment thereof, or (iv) a pharmaceutical composition comprising the antibody or the antigen-binding fragment thereof of (i), the bispecific or multispecific molecule of (ii) or the immunoconjugate of (iii), or (v) a chimeric antigen receptor comprising an antigen-binding domain of the antibody or the antigen-binding fragment thereof according to claim 1, or (vi) an isolated nucleic acid molecule encoding the chimeric antigen receptor of (v), or (vii) a vector comprising an isolated nucleic acid molecule encoding the chimeric antigen receptor of (v), or (viii) a host cell comprising an isolated nucleic acid molecule encoding the chimeric antigen receptor of (v;

wherein the tumor expresses CLDN18.2; or wherein the tumor comprises a tumor cell expressing CLDN18.2;

and wherein the tumor cell is a gastric cancer cell.

20. A method for detecting the presence or amount of CLDN18.2 in a sample, comprising the following steps:

(1) contacting the sample with the antibody or the antigen-binding fragment thereof according to claim 1; and (2) detecting the formation or amount of a complex between the antibody or the antigen-binding fragment thereof and CLDN18.2.

21. The method of claim 19, wherein the method further comprises administering to the subject in need thereof an additional antitumor agent or an additional antitumor therapy.

22. The method of claim 21, wherein one or more of:

(i) the additional antitumor agent is selected from an alkylating agent, an anti-mitotic agent, an antitumor antibiotic, an antimetabolite, a topoisomerase inhibitor, a tyrosine kinase inhibitor, a radionuclide, a radiosensitizer, an anti-angiogenesis agent, a cytokine, a molecular-targeted agent, an immune checkpoint inhibitor or an oncolytic virus; or, (ii) the additional antitumor therapy is selected from surgery, chemotherapy, radiation therapy, targeted therapy, immunotherapy, hormone therapy, gene therapy or palliative care.

23. The antibody or the antigen-binding fragment thereof according to claim 1, wherein the antibody and the antigen-binding fragment comprises:

(1) a VH comprising a VH CDR1 comprising the amino acid sequence of SEQ ID NO: 75, a VH CDR2 comprising the amino acid sequence of SEQ ID NO: 76, a VH CDR3 comprising the amino acid sequence of SEQ ID NO: 77 and a VL comprising a VL CDR1 comprising the amino acid sequence of SEQ ID NO: 96, a VL CDR2 comprising the amino acid sequence of SEQ ID NO: 79, and a VL CDR3 comprising the amino acid sequence of SEQ ID NO: 80, wherein the VH comprises the amino acid sequence of SEQ ID NO: 91 and the VL comprises the amino acid sequence of SEQ ID NO: 92; or (2) a VH comprising a VH CDR1 comprising the amino acid sequence of SEQ ID NO: 75, a VH CDR2 comprising the amino acid sequence of SEQ ID NO: 76, a VH CDR3 comprising the amino acid sequence of SEQ ID NO: 77 and a VL comprising a VL CDR1 comprising the amino acid sequence of SEQ ID NO: 78, a VL CDR2 comprising the amino acid sequence of SEQ ID NO: 79, and a VL CDR3 comprising the amino acid sequence of SEQ ID NO: 80, wherein the VH comprises the amino acid sequence of SEQ ID NO: 99 and the VL comprises the amino acid sequence of SEQ ID NO: 100; or (3) a VH comprising a VH CDR1 comprising the amino acid sequence of SEQ ID NO: 75, a VH CDR2 comprising the amino acid sequence of SEQ ID NO: 76, a VH CDR3 comprising the amino acid sequence of SEQ ID NO: 77 and a VL comprising a VL CDR1 comprising the amino acid sequence of SEQ ID NO: 78, a VL CDR2 comprising the amino acid sequence of SEQ ID NO: 79, and a VL CDR3 comprising the amino acid sequence of SEQ ID NO: 80, wherein the VH comprises the amino acid sequence of SEQ ID NO: 101 and the VL comprises the amino acid sequence of SEQ ID NO: 102; or (4) a VH comprising a VH CDR1 comprising the amino acid sequence of SEQ ID NO: 75, a VH CDR2 comprising the amino acid sequence of SEQ ID NO: 76, a VH CDR3 comprising the amino acid sequence of SEQ ID NO: 77 and a VL comprising a VL CDR1 comprising the amino acid sequence of SEQ ID NO: 78, a VL CDR2 comprising the amino acid sequence of SEQ ID NO: 79, and a VL CDR3 comprising the amino acid sequence of SEQ ID NO: 80, wherein the VH comprises the amino acid sequence of SEQ ID NO: 73 and the VL comprises the amino acid sequence of SEQ ID NO: 74.

24. The antibody or the antigen-binding fragment thereof according to claim 3, wherein:

(i) the heavy chain constant region is an Immunoglobulin G (IgG) heavy chain constant region selected from an IgG1 heavy chain constant region, an IgG2 heavy chain constant region, an IgG3 heavy chain constant region or an IgG4 heavy chain constant region; and (ii) the light chain constant region is a kappa (κ) light chain constant region.

25. The antibody or the antigen-binding fragment thereof according to claim 24, wherein:

(i) the heavy chain constant region (CH) comprises the amino acid sequence of SEQ ID NO: 81; and (ii) the light chain constant region (CL) comprises the amino acid sequence of SEQ ID NO: 82.

26. The pharmaceutical composition according to claim 12, wherein the pharmaceutical composition further comprises an additional pharmaceutically active agent, wherein the pharmaceutically active agent is an antitumor agent selected from the group consisting of an alkylating agent, an anti-mitotic agent, an antitumor antibiotic, an antimetabolite, a topoisomerase inhibitor, a tyrosine kinase inhibitor, a radionuclide, a radiosensitizer, an anti-angiogenesis agent, a cytokine, a molecular-targeted agent, an immune checkpoint inhibitor and an oncolytic virus.

27. The kit according to claim 13, wherein the antibody or the antigen-binding fragment thereof is labeled with a detectable label, and wherein the kit further comprises a second antibody which specifically recognizes said antibody or the antigen-binding fragment thereof.

28. The chimeric antigen receptor according to claim 14, wherein the antigen-binding domain is an scFv.

29. The host cell according to claim 17, wherein the host cell is an immune effector cell.

30. The method of claim 20, wherein the CLDN18.2 is human CLDN18.2.

\*  \*  \*  \*  \*

SEQUENCE LISTING

<160> NUMBER OF SEQ ID NOS: 128

<210> SEQ ID NO 1
<211> LENGTH: 113
<212> TYPE: PRT
<213> ORGANISM: Artificial sequence
<220> FEATURE:
<223> OTHER INFORMATION: 1D10 VH

<400> SEQUENCE: 1

Gln Val Gln Leu Gln Gln Pro Gly Ala Glu Leu Val Lys Pro Gly Ala
1               5                   10                  15

-continued

```
Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Met Ile Tyr Pro Asn Ser Gly Ser Ile Asn Tyr Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ser Val Tyr Phe Asp Tyr Trp Gly Gln Gly Thr Thr Leu Thr Val Ser
            100                 105                 110

Ser
```

```
<210> SEQ ID NO 2
<211> LENGTH: 107
<212> TYPE: PRT
<213> ORGANISM: Artificial sequence
<220> FEATURE:
<223> OTHER INFORMATION: 1D10 VL

<400> SEQUENCE: 2

Asp Ile Gln Gly Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
            35                  40                  45

Tyr Ala Thr Ser Ser Leu Asp Ser Gly Val Pro Lys Arg Phe Ser Val
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Pro
                85                  90                  95

Thr Phe Gly Gly Gly Thr Lys Leu Glu Ile Lys
            100                 105
```

```
<210> SEQ ID NO 3
<211> LENGTH: 7
<212> TYPE: PRT
<213> ORGANISM: Artificial sequence
<220> FEATURE:
<223> OTHER INFORMATION: 1D10 HCDR1

<400> SEQUENCE: 3

Gly Tyr Thr Phe Thr Ser Tyr
1               5
```

```
<210> SEQ ID NO 4
<211> LENGTH: 6
<212> TYPE: PRT
<213> ORGANISM: Artificial sequence
<220> FEATURE:
<223> OTHER INFORMATION: 1D10 HCDR2

<400> SEQUENCE: 4

Tyr Pro Asn Ser Gly Ser
1               5
```

```
<210> SEQ ID NO 5
<211> LENGTH: 4
<212> TYPE: PRT
<213> ORGANISM: Artificial sequence
<220> FEATURE:
<223> OTHER INFORMATION: 1D10 HCDR3

<400> SEQUENCE: 5

Tyr Phe Asp Tyr
1

<210> SEQ ID NO 6
<211> LENGTH: 8
<212> TYPE: PRT
<213> ORGANISM: Artificial sequence
<220> FEATURE:
<223> OTHER INFORMATION: 1D10 LCDR1

<400> SEQUENCE: 6

Gln Asp Ile Gly Ser Ser Leu Asn
1               5

<210> SEQ ID NO 7
<211> LENGTH: 7
<212> TYPE: PRT
<213> ORGANISM: Artificial sequence
<220> FEATURE:
<223> OTHER INFORMATION: 1D10 LCDR2

<400> SEQUENCE: 7

Ala Thr Ser Ser Leu Asp Ser
1               5

<210> SEQ ID NO 8
<211> LENGTH: 9
<212> TYPE: PRT
<213> ORGANISM: Artificial sequence
<220> FEATURE:
<223> OTHER INFORMATION: 1D10 LCDR3

<400> SEQUENCE: 8

Leu Gln Tyr Ala Ser Ser Pro Pro Thr
1               5

<210> SEQ ID NO 9
<211> LENGTH: 118
<212> TYPE: PRT
<213> ORGANISM: Artificial sequence
<220> FEATURE:
<223> OTHER INFORMATION: 2F12 VH

<400> SEQUENCE: 9

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Ile His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Ile Tyr Tyr Cys
                85                  90                  95
```

-continued

```
Ala Lys Trp Asp Arg Gly Asn Cys Phe Asp Tyr Trp Gly Gln Gly Thr
        100                 105                 110

Thr Leu Thr Val Ser Ser
        115

<210> SEQ ID NO 10
<211> LENGTH: 113
<212> TYPE: PRT
<213> ORGANISM: Artificial sequence
<220> FEATURE:
<223> OTHER INFORMATION: 2F12 VL

<400> SEQUENCE: 10

Asp Ile Val Leu Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Lys Tyr Leu Thr Trp Tyr Gln Gln Lys Val Gly Gln
        35                  40                  45

Pro Pro Lys Leu Leu Ile Tyr Trp Ala Ser Ile Arg Glu Cys Gly Val
    50                  55                  60

Pro Asp Arg Phe Thr Gly Ser Gly Ser Gly Thr Asp Phe Ile Leu Thr
65                  70                  75                  80

Ile Ser Ser Val Gln Ala Glu Asp Leu Ala Val Tyr Tyr Cys Gln Asn
                85                  90                  95

Ala Tyr Ser Tyr Pro Leu Thr Phe Gly Ala Gly Thr Lys Leu Glu Leu
            100                 105                 110

Lys

<210> SEQ ID NO 11
<211> LENGTH: 7
<212> TYPE: PRT
<213> ORGANISM: Artificial sequence
<220> FEATURE:
<223> OTHER INFORMATION: 2F12 HCDR1

<400> SEQUENCE: 11

Gly Phe Thr Phe Ser Asp Tyr
1               5

<210> SEQ ID NO 12
<211> LENGTH: 6
<212> TYPE: PRT
<213> ORGANISM: Artificial sequence
<220> FEATURE:
<223> OTHER INFORMATION: 2F12 HCDR2

<400> SEQUENCE: 12

Ser Ser Gly Ser Ser Thr
1               5

<210> SEQ ID NO 13
<211> LENGTH: 9
<212> TYPE: PRT
<213> ORGANISM: Artificial sequence
<220> FEATURE:
<223> OTHER INFORMATION: 2F12 HCDR3

<400> SEQUENCE: 13

Trp Asp Arg Gly Asn Cys Phe Asp Tyr
1               5
```

-continued

```
<210> SEQ ID NO 14
<211> LENGTH: 17
<212> TYPE: PRT
<213> ORGANISM: Artificial sequence
<220> FEATURE:
<223> OTHER INFORMATION: 2F12 LCDR1

<400> SEQUENCE: 14

Lys Ser Ser Gln Ser Leu Leu Asn Ser Gly Asn Gln Lys Lys Tyr Leu
1               5                   10                  15

Thr

<210> SEQ ID NO 15
<211> LENGTH: 7
<212> TYPE: PRT
<213> ORGANISM: Artificial sequence
<220> FEATURE:
<223> OTHER INFORMATION: 2F12 LCDR2

<400> SEQUENCE: 15

Trp Ala Ser Ile Arg Glu Cys
1               5

<210> SEQ ID NO 16
<211> LENGTH: 9
<212> TYPE: PRT
<213> ORGANISM: Artificial sequence
<220> FEATURE:
<223> OTHER INFORMATION: 2F12 LCDR3

<400> SEQUENCE: 16

Gln Asn Ala Tyr Ser Tyr Pro Leu Thr
1               5

<210> SEQ ID NO 17
<211> LENGTH: 118
<212> TYPE: PRT
<213> ORGANISM: Artificial sequence
<220> FEATURE:
<223> OTHER INFORMATION: 3F2 VH

<400> SEQUENCE: 17

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Glu Lys Arg Leu Glu Trp Ile
        35                  40                  45

Ala Thr Ile Asn Asp Gly Gly Thr Tyr Thr Tyr Tyr Pro Asp Asn Val
    50                  55                  60

Lys Gly Arg Phe Thr Ile Ser Arg Asp Asn Ala Lys Asn Asn Leu Tyr
65                  70                  75                  80

Leu His Met Ser His Leu Lys Ser Asp Asp Thr Ala Ile His Tyr Cys
                85                  90                  95

Thr Arg Leu Ala Arg Gly Asn Ser Met Asp Tyr Trp Gly Gln Gly Thr
            100                 105                 110

Ser Val Thr Val Ser Ser
        115

<210> SEQ ID NO 18
<211> LENGTH: 118
<212> TYPE: PRT
<213> ORGANISM: Artificial sequence
```

-continued

```
<220> FEATURE:
<223> OTHER INFORMATION: 3F2 VL

<400> SEQUENCE: 18

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Glu Lys Arg Leu Glu Trp Ile
        35                  40                  45

Ala Thr Ile Asn Asp Gly Gly Thr Tyr Thr Tyr Tyr Pro Asp Asn Val
        50                  55                  60

Lys Gly Arg Phe Thr Ile Ser Arg Asp Asn Ala Lys Asn Asn Leu Tyr
65                  70                  75                  80

Leu His Met Ser His Leu Lys Ser Asp Asp Thr Ala Ile His Tyr Cys
                85                  90                  95

Thr Arg Leu Ala Arg Gly Asn Ser Met Asp Tyr Trp Gly Gln Gly Thr
            100                 105                 110

Ser Val Thr Val Ser Ser
        115

<210> SEQ ID NO 19
<211> LENGTH: 7
<212> TYPE: PRT
<213> ORGANISM: Artificial sequence
<220> FEATURE:
<223> OTHER INFORMATION: 3F2 HCDR1

<400> SEQUENCE: 19

Gly Phe Thr Phe Ser Thr Tyr
1               5

<210> SEQ ID NO 20
<211> LENGTH: 6
<212> TYPE: PRT
<213> ORGANISM: Artificial sequence
<220> FEATURE:
<223> OTHER INFORMATION: 3F2 HCDR2

<400> SEQUENCE: 20

Asn Asp Gly Gly Thr Tyr
1               5

<210> SEQ ID NO 21
<211> LENGTH: 9
<212> TYPE: PRT
<213> ORGANISM: Artificial sequence
<220> FEATURE:
<223> OTHER INFORMATION: 3F2 HCDR3

<400> SEQUENCE: 21

Leu Ala Arg Gly Asn Ser Met Asp Tyr
1               5

<210> SEQ ID NO 22
<211> LENGTH: 17
<212> TYPE: PRT
<213> ORGANISM: Artificial sequence
<220> FEATURE:
<223> OTHER INFORMATION: 3F2 LCDR1

<400> SEQUENCE: 22

Lys Ser Ser Gln Ser Leu Leu Asn Ser Gly Asn Gln Lys Asn Tyr Leu
```

-continued

```
1               5               10              15

Thr

<210> SEQ ID NO 23
<211> LENGTH: 7
<212> TYPE: PRT
<213> ORGANISM: Artificial sequence
<220> FEATURE:
<223> OTHER INFORMATION: 3F2 LCDR2

<400> SEQUENCE: 23

Trp Ala Ser Thr Arg Glu Tyr
1               5

<210> SEQ ID NO 24
<211> LENGTH: 9
<212> TYPE: PRT
<213> ORGANISM: Artificial sequence
<220> FEATURE:
<223> OTHER INFORMATION: 3F2 LCDR3

<400> SEQUENCE: 24

Gln Asn Asn Tyr Ile Tyr Pro Leu Thr
1               5

<210> SEQ ID NO 25
<211> LENGTH: 113
<212> TYPE: PRT
<213> ORGANISM: Artificial sequence
<220> FEATURE:
<223> OTHER INFORMATION: 5F9 VH

<400> SEQUENCE: 25

Gln Val Gln Leu Gln Gln Ser Gly Ala Glu Leu Val Lys Pro Gly Ala
1               5               10              15

Ser Val Lys Leu Ser Cys Lys Ala Ser Gly Tyr Thr Phe Thr Ser Tyr
                20              25              30

Trp Met His Trp Val Lys Gln Arg Pro Gly Gln Gly Leu Glu Trp Ile
            35              40              45

Gly Met Ile His Pro Asn Ser Val Ser Thr Asn Tyr Asn Glu Lys Phe
        50              55              60

Lys Ser Lys Ala Thr Leu Thr Val Asp Lys Ser Ser Ser Thr Ala Tyr
65              70              75              80

Met Gln Leu Ser Ser Leu Thr Ser Glu Asp Ser Ala Val Tyr Tyr Cys
                85              90              95

Ala Val Tyr Phe Asp Tyr Trp Gly Gln Gly Thr Thr Leu Thr Val Ser
                100             105             110

Ser

<210> SEQ ID NO 26
<211> LENGTH: 107
<212> TYPE: PRT
<213> ORGANISM: Artificial sequence
<220> FEATURE:
<223> OTHER INFORMATION: 5F9 VL

<400> SEQUENCE: 26

Asp Ile Gln Val Thr Gln Ser Pro Ser Ser Leu Ser Ala Ser Leu Gly
1               5               10              15

Glu Arg Val Ser Leu Thr Cys Arg Ala Ser Gln Asp Ile Gly Ser Ser
                20              25              30
```

-continued

```
Leu Asn Trp Leu Gln Gln Glu Pro Asp Gly Thr Ile Lys Arg Leu Ile
        35                  40                  45

Tyr Ala Ser Ser Ser Leu Asn Ser Gly Val Pro Lys Arg Phe Ser Val
        50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Thr Ser Pro Pro
                    85                  90                  95

Thr Phe Gly Gly Gly Thr Lys Leu Glu Ile Lys
                100                 105
```

```
<210> SEQ ID NO 27
<211> LENGTH: 7
<212> TYPE: PRT
<213> ORGANISM: Artificial sequence
<220> FEATURE:
<223> OTHER INFORMATION: 5F9 HCDR1

<400> SEQUENCE: 27

Gly Tyr Thr Phe Thr Ser Tyr
1               5
```

```
<210> SEQ ID NO 28
<211> LENGTH: 6
<212> TYPE: PRT
<213> ORGANISM: Artificial sequence
<220> FEATURE:
<223> OTHER INFORMATION: 5F9 HCDR2

<400> SEQUENCE: 28

His Pro Asn Ser Val Ser
1               5
```

```
<210> SEQ ID NO 29
<211> LENGTH: 6
<212> TYPE: PRT
<213> ORGANISM: Artificial sequence
<220> FEATURE:
<223> OTHER INFORMATION: 5F9 HCDR3

<400> SEQUENCE: 29

Ala Val Tyr Phe Asp Tyr
1               5
```

```
<210> SEQ ID NO 30
<211> LENGTH: 11
<212> TYPE: PRT
<213> ORGANISM: Artificial sequence
<220> FEATURE:
<223> OTHER INFORMATION: 5F9 LCDR1

<400> SEQUENCE: 30

Arg Ala Ser Gln Asp Ile Gly Ser Ser Leu Asn
1               5                   10
```

```
<210> SEQ ID NO 31
<211> LENGTH: 7
<212> TYPE: PRT
<213> ORGANISM: Artificial sequence
<220> FEATURE:
<223> OTHER INFORMATION: 5F9 LCDR2

<400> SEQUENCE: 31

Ala Ser Ser Ser Leu Asn Ser
1               5
```

-continued

<210> SEQ ID NO 32
<211> LENGTH: 9
<212> TYPE: PRT
<213> ORGANISM: Artificial sequence
<220> FEATURE:
<223> OTHER INFORMATION: 5F9 LCDR3

<400> SEQUENCE: 32

Leu Gln Tyr Ala Thr Ser Pro Pro Thr
1               5

<210> SEQ ID NO 33
<211> LENGTH: 118
<212> TYPE: PRT
<213> ORGANISM: Artificial sequence
<220> FEATURE:
<223> OTHER INFORMATION: 9F3 VH

<400> SEQUENCE: 33

Glu Val Arg Leu Gln Gln Ser Gly Pro Glu Leu Val Lys Pro Gly Ala
1               5                   10                  15

Ser Val Lys Ile Pro Cys Lys Ala Ser Gly Tyr Lys Phe Thr Asp Tyr
            20                  25                  30

Asn Met Asp Trp Val Lys Gln Ser His Gly Lys Ser Leu Glu Trp Ile
        35                  40                  45

Gly Glu Ile Asn Pro Asn Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Ile Tyr Tyr Gly Asn Ser Phe Ala Tyr Trp Gly Gln Gly Thr
            100                 105                 110

Leu Val Thr Val Ser Ser
        115

<210> SEQ ID NO 34
<211> LENGTH: 113
<212> TYPE: PRT
<213> ORGANISM: Artificial sequence
<220> FEATURE:
<223> OTHER INFORMATION: 9F3 VL

<400> SEQUENCE: 34

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Leu Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Phe Tyr Pro Leu Thr Phe Gly Ala Gly Thr Lys Leu Glu Ile
            100                 105                 110

-continued

Lys

<210> SEQ ID NO 35
<211> LENGTH: 7
<212> TYPE: PRT
<213> ORGANISM: Artificial sequence
<220> FEATURE:
<223> OTHER INFORMATION: 9F3 HCDR1

<400> SEQUENCE: 35

Gly Tyr Lys Phe Thr Asp Tyr
1               5

<210> SEQ ID NO 36
<211> LENGTH: 6
<212> TYPE: PRT
<213> ORGANISM: Artificial sequence
<220> FEATURE:
<223> OTHER INFORMATION: 9F3 HCDR2

<400> SEQUENCE: 36

Asn Pro Asn Asn Gly Gly
1               5

<210> SEQ ID NO 37
<211> LENGTH: 9
<212> TYPE: PRT
<213> ORGANISM: Artificial sequence
<220> FEATURE:
<223> OTHER INFORMATION: 9F3 HCDR3

<400> SEQUENCE: 37

Ile Tyr Tyr Gly Asn Ser Phe Ala Tyr
1               5

<210> SEQ ID NO 38
<211> LENGTH: 17
<212> TYPE: PRT
<213> ORGANISM: Artificial sequence
<220> FEATURE:
<223> OTHER INFORMATION: 9F3 LCDR1

<400> SEQUENCE: 38

Lys Ser Ser Gln Ser Leu Leu Asn Ser Gly Asn Leu Lys Asn Tyr Leu
1               5                   10                  15

Thr

<210> SEQ ID NO 39
<211> LENGTH: 7
<212> TYPE: PRT
<213> ORGANISM: Artificial sequence
<220> FEATURE:
<223> OTHER INFORMATION: 9F3 LCDR2

<400> SEQUENCE: 39

Trp Ala Ser Thr Arg Glu Ser
1               5

<210> SEQ ID NO 40
<211> LENGTH: 9
<212> TYPE: PRT
<213> ORGANISM: Artificial sequence
<220> FEATURE:
<223> OTHER INFORMATION: 9F3 LCDR3

<400> SEQUENCE: 40

-continued

```
Gln Asn Asp Tyr Phe Tyr Pro Leu Thr
1               5

<210> SEQ ID NO 41
<211> LENGTH: 118
<212> TYPE: PRT
<213> ORGANISM: Artificial sequence
<220> FEATURE:
<223> OTHER INFORMATION: 10B11 VH

<400> SEQUENCE: 41

Gln Val Gln Met Lys Glu Ser Gly Ala Glu Leu Val Lys Pro Gly Ala
1               5                   10                  15

Ser Val Lys Ile Ser Cys Lys Ala Ser Gly Tyr Ala Phe Ser Thr Tyr
                20                  25                  30

Trp Met Asp Trp Val Lys Gln Arg Pro Gly Lys Gly Leu Glu Trp Ile
            35                  40                  45

Gly Gln Ile Tyr Pro Gly Asn Gly Asp Thr Asn Tyr Asn Gly Lys Phe
        50                  55                  60

Lys Gly Lys Ala Thr Leu Thr Ala Asp Lys Ser Ser Ser Thr Ala Asp
65                  70                  75                  80

Met Gln Leu Ser Ser Leu Thr Ser Glu Asp Ser Ala Val Tyr Phe Cys
                85                  90                  95

Ala Arg Leu Gly Tyr Gly Asn Ser Phe Thr Tyr Trp Gly Gln Gly Thr
            100                 105                 110

Leu Val Thr Val Ser Ala
        115

<210> SEQ ID NO 42
<211> LENGTH: 113
<212> TYPE: PRT
<213> ORGANISM: Artificial sequence
<220> FEATURE:
<223> OTHER INFORMATION: 10B11 VL

<400> SEQUENCE: 42

Asp Ile Gln Val Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Phe Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Ala Tyr Phe Tyr Pro Phe Thr Phe Gly Ser Gly Thr Lys Leu Glu Ile
            100                 105                 110

Lys

<210> SEQ ID NO 43
<211> LENGTH: 7
<212> TYPE: PRT
<213> ORGANISM: Artificial sequence
<220> FEATURE:
<223> OTHER INFORMATION: 10B11 HCDR1

<400> SEQUENCE: 43
```

```
Gly Tyr Ala Phe Ser Thr Tyr
1               5

<210> SEQ ID NO 44
<211> LENGTH: 6
<212> TYPE: PRT
<213> ORGANISM: Artificial sequence
<220> FEATURE:
<223> OTHER INFORMATION: 10B11 HCDR2

<400> SEQUENCE: 44

Tyr Pro Gly Asn Gly Asp
1               5

<210> SEQ ID NO 45
<211> LENGTH: 9
<212> TYPE: PRT
<213> ORGANISM: Artificial sequence
<220> FEATURE:
<223> OTHER INFORMATION: 10B11 HCDR3

<400> SEQUENCE: 45

Leu Gly Tyr Gly Asn Ser Phe Thr Tyr
1               5

<210> SEQ ID NO 46
<211> LENGTH: 17
<212> TYPE: PRT
<213> ORGANISM: Artificial sequence
<220> FEATURE:
<223> OTHER INFORMATION: 10B11 LCDR1

<400> SEQUENCE: 46

Lys Ser Ser Gln Ser Leu Leu Asn Ser Gly Asn Gln Lys Asn Tyr Leu
1               5                   10                  15

Thr

<210> SEQ ID NO 47
<211> LENGTH: 7
<212> TYPE: PRT
<213> ORGANISM: Artificial sequence
<220> FEATURE:
<223> OTHER INFORMATION: 10B11 LCDR2

<400> SEQUENCE: 47

Trp Ala Ser Thr Arg Glu Ser
1               5

<210> SEQ ID NO 48
<211> LENGTH: 9
<212> TYPE: PRT
<213> ORGANISM: Artificial sequence
<220> FEATURE:
<223> OTHER INFORMATION: 10B11 LCDR3

<400> SEQUENCE: 48

Gln Asn Ala Tyr Phe Tyr Pro Phe Thr
1               5

<210> SEQ ID NO 49
<211> LENGTH: 118
<212> TYPE: PRT
<213> ORGANISM: Artificial sequence
<220> FEATURE:
<223> OTHER INFORMATION: 27B5 VH
```

-continued

<400> SEQUENCE: 49

```
Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile His Pro Ser Asn Gly Gly Ser Asn His Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Pro Ile Tyr Tyr Gly Asn Ser Leu Ala Tyr Trp Gly His Gly Thr
            100                 105                 110

Leu Val Thr Val Ser Ala
        115
```

<210> SEQ ID NO 50
<211> LENGTH: 113
<212> TYPE: PRT
<213> ORGANISM: Artificial sequence
<220> FEATURE:
<223> OTHER INFORMATION: 27B5 VL

<400> SEQUENCE: 50

```
Asp Val Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Ser Tyr Phe Tyr Pro Phe Thr Phe Gly Ser Gly Thr Lys Leu Glu Ile
            100                 105                 110

Lys
```

<210> SEQ ID NO 51
<211> LENGTH: 7
<212> TYPE: PRT
<213> ORGANISM: Artificial sequence
<220> FEATURE:
<223> OTHER INFORMATION: 27B5 HCDR1

<400> SEQUENCE: 51

```
Gly Tyr Thr Phe Thr Ser Tyr
1               5
```

<210> SEQ ID NO 52
<211> LENGTH: 6
<212> TYPE: PRT
<213> ORGANISM: Artificial sequence
<220> FEATURE:
<223> OTHER INFORMATION: 27B5 HCDR2

-continued

```
<400> SEQUENCE: 52

His Pro Ser Asn Gly Gly
1               5

<210> SEQ ID NO 53
<211> LENGTH: 9
<212> TYPE: PRT
<213> ORGANISM: Artificial sequence
<220> FEATURE:
<223> OTHER INFORMATION: 27B5 HCDR3

<400> SEQUENCE: 53

Ile Tyr Tyr Gly Asn Ser Leu Ala Tyr
1               5

<210> SEQ ID NO 54
<211> LENGTH: 17
<212> TYPE: PRT
<213> ORGANISM: Artificial sequence
<220> FEATURE:
<223> OTHER INFORMATION: 27B5 LCDR1

<400> SEQUENCE: 54

Lys Ser Ser Gln Ser Leu Leu Asn Ser Gly Asn Gln Lys Asn Tyr Leu
1               5                   10                  15

Thr

<210> SEQ ID NO 55
<211> LENGTH: 7
<212> TYPE: PRT
<213> ORGANISM: Artificial sequence
<220> FEATURE:
<223> OTHER INFORMATION: 27B5 LCDR2

<400> SEQUENCE: 55

Trp Ala Ser Thr Arg Glu Ser
1               5

<210> SEQ ID NO 56
<211> LENGTH: 8
<212> TYPE: PRT
<213> ORGANISM: Artificial sequence
<220> FEATURE:
<223> OTHER INFORMATION: 27B5 LCDR3

<400> SEQUENCE: 56

Gln Asn Ser Tyr Phe Tyr Pro Phe
1               5

<210> SEQ ID NO 57
<211> LENGTH: 118
<212> TYPE: PRT
<213> ORGANISM: Artificial sequence
<220> FEATURE:
<223> OTHER INFORMATION: 37B1 VH

<400> SEQUENCE: 57

Glu Val Arg Leu Gln Gln Ser Gly Pro Glu Leu Val Lys Pro Gly Ala
1               5                   10                  15

Ser Val Lys Met Ser Cys Lys Ala Ser Gly Tyr Ser Phe Thr Asp Tyr
            20                  25                  30

Asn Met His Trp Val Lys Gln Ser His Gly Lys Ser Pro Glu Trp Val
        35                  40                  45
```

-continued

```
Gly Tyr Ile Asn Pro Asn Lys Gly Gly Thr Gly Tyr Asn Gln Lys Phe
    50                  55                  60

Lys Gly Lys Ala Thr Leu Thr Val Asn Lys Ser Ser Ser Thr Ala Asn
65                  70                  75                  80

Met Glu Leu Arg Ser Leu Thr Ser Glu Asp Ser Ala Val Tyr Tyr Cys
                85                  90                  95

Ala Arg Ile Trp Tyr Gly Asn Ser Phe Ala Tyr Trp Gly Gln Gly Thr
            100                 105                 110

Leu Val Thr Val Ser Ala
        115

<210> SEQ ID NO 58
<211> LENGTH: 113
<212> TYPE: PRT
<213> ORGANISM: Artificial sequence
<220> FEATURE:
<223> OTHER INFORMATION: 37B1 VL

<400> SEQUENCE: 58

Asp Val Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Phe Cys Gln Asn
                85                  90                  95

Asp Tyr Phe Tyr Pro Phe Thr Phe Gly Ser Gly Thr Lys Leu Glu Ile
            100                 105                 110

Lys

<210> SEQ ID NO 59
<211> LENGTH: 7
<212> TYPE: PRT
<213> ORGANISM: Artificial sequence
<220> FEATURE:
<223> OTHER INFORMATION: 37B1 HCDR1

<400> SEQUENCE: 59

Gly Tyr Ser Phe Thr Asp Tyr
1               5

<210> SEQ ID NO 60
<211> LENGTH: 6
<212> TYPE: PRT
<213> ORGANISM: Artificial sequence
<220> FEATURE:
<223> OTHER INFORMATION: 37B1 HCDR2

<400> SEQUENCE: 60

Asn Pro Asn Lys Gly Gly
1               5

<210> SEQ ID NO 61
<211> LENGTH: 9
<212> TYPE: PRT
<213> ORGANISM: Artificial sequence
```

-continued

<220> FEATURE:
<223> OTHER INFORMATION: 37B1 HCDR3

<400> SEQUENCE: 61

Ile Trp Tyr Gly Asn Ser Phe Ala Tyr
1               5

<210> SEQ ID NO 62
<211> LENGTH: 17
<212> TYPE: PRT
<213> ORGANISM: Artificial sequence
<220> FEATURE:
<223> OTHER INFORMATION: 37B1 LCDR1

<400> SEQUENCE: 62

Lys Ser Ser Gln Ser Leu Leu Asn Ser Gly Asn Gln Lys Asn Tyr Leu
1               5                   10                  15

Thr

<210> SEQ ID NO 63
<211> LENGTH: 7
<212> TYPE: PRT
<213> ORGANISM: Artificial sequence
<220> FEATURE:
<223> OTHER INFORMATION: 37B1 LCDR2

<400> SEQUENCE: 63

Trp Ala Ser Thr Arg Glu Ser
1               5

<210> SEQ ID NO 64
<211> LENGTH: 9
<212> TYPE: PRT
<213> ORGANISM: Artificial sequence
<220> FEATURE:
<223> OTHER INFORMATION: 37B1 LCDR3

<400> SEQUENCE: 64

Gln Asn Asp Tyr Phe Tyr Pro Phe Thr
1               5

<210> SEQ ID NO 65
<211> LENGTH: 119
<212> TYPE: PRT
<213> ORGANISM: Artificial sequence
<220> FEATURE:
<223> OTHER INFORMATION: 44A8 VH

<400> SEQUENCE: 65

Glu Val Arg Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Asn Pro Lys Asn Gly Gly Ile Arg Tyr Asn Gln Lys Phe
    50                  55                  60

Thr Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Gly Tyr Tyr Gly Asn Thr Leu Asp Asn Trp Gly Gln Gly
            100                 105                 110

-continued

Thr Ser Val Thr Val Ser Ser
        115

<210> SEQ ID NO 66
<211> LENGTH: 113
<212> TYPE: PRT
<213> ORGANISM: Artificial sequence
<220> FEATURE:
<223> OTHER INFORMATION: 44A8 VL

<400> SEQUENCE: 66

Asp Ile Val Met Thr Gln Ser Pro Ser Ser Leu Thr Leu Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Ser Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Ala Tyr Phe Tyr Pro Trp Thr Phe Gly Gly Gly Thr Lys Leu Glu Ile
            100                 105                 110

Lys

<210> SEQ ID NO 67
<211> LENGTH: 7
<212> TYPE: PRT
<213> ORGANISM: Artificial sequence
<220> FEATURE:
<223> OTHER INFORMATION: 44A8 HCDR1

<400> SEQUENCE: 67

Gly Tyr Thr Phe Thr Asp Tyr
1               5

<210> SEQ ID NO 68
<211> LENGTH: 6
<212> TYPE: PRT
<213> ORGANISM: Artificial sequence
<220> FEATURE:
<223> OTHER INFORMATION: 44A8 HCDR2

<400> SEQUENCE: 68

Asn Pro Lys Asn Gly Gly
1               5

<210> SEQ ID NO 69
<211> LENGTH: 10
<212> TYPE: PRT
<213> ORGANISM: Artificial sequence
<220> FEATURE:
<223> OTHER INFORMATION: 44A8 HCDR3

<400> SEQUENCE: 69

Gly Gly Tyr Tyr Gly Asn Thr Leu Asp Asn
1               5                   10

<210> SEQ ID NO 70
<211> LENGTH: 17

-continued

```
<212> TYPE: PRT
<213> ORGANISM: Artificial sequence
<220> FEATURE:
<223> OTHER INFORMATION: 44A8 LCDR1

<400> SEQUENCE: 70

Lys Ser Ser Gln Ser Leu Leu Asn Ser Gly Asn Gln Lys Asn Tyr Leu
1               5                   10                  15

Thr

<210> SEQ ID NO 71
<211> LENGTH: 7
<212> TYPE: PRT
<213> ORGANISM: Artificial sequence
<220> FEATURE:
<223> OTHER INFORMATION: 44A8 LCDR2

<400> SEQUENCE: 71

Trp Ala Ser Thr Ser Glu Ser
1               5

<210> SEQ ID NO 72
<211> LENGTH: 9
<212> TYPE: PRT
<213> ORGANISM: Artificial sequence
<220> FEATURE:
<223> OTHER INFORMATION: 44A8 LCDR3

<400> SEQUENCE: 72

Gln Asn Ala Tyr Phe Tyr Pro Trp Thr
1               5

<210> SEQ ID NO 73
<211> LENGTH: 119
<212> TYPE: PRT
<213> ORGANISM: Artificial sequence
<220> FEATURE:
<223> OTHER INFORMATION: 44F7 VH

<400> SEQUENCE: 73

Gln Val Gln Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Ala Pro Arg Gln Gly Leu Glu Trp Ile
        35                  40                  45

Gly Thr Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Tyr Tyr Gly Asn Ser Leu Asp Tyr Trp Gly Gln Gly
            100                 105                 110

Thr Thr Leu Thr Val Ser Ser
        115

<210> SEQ ID NO 74
<211> LENGTH: 113
<212> TYPE: PRT
<213> ORGANISM: Artificial sequence
<220> FEATURE:
<223> OTHER INFORMATION: 44F7 VL
```

-continued

<400> SEQUENCE: 74

Asp Ile Gln Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Ala Tyr Tyr Tyr Pro Phe Thr Phe Gly Ser Gly Thr Lys Leu Glu Ile
            100                 105                 110

Lys

<210> SEQ ID NO 75
<211> LENGTH: 7
<212> TYPE: PRT
<213> ORGANISM: Artificial sequence
<220> FEATURE:
<223> OTHER INFORMATION: 44F7 HCDR1

<400> SEQUENCE: 75

Gly Tyr Thr Phe Thr Ser Tyr
1               5

<210> SEQ ID NO 76
<211> LENGTH: 6
<212> TYPE: PRT
<213> ORGANISM: Artificial sequence
<220> FEATURE:
<223> OTHER INFORMATION: 44F7 HCDR2

<400> SEQUENCE: 76

Tyr Pro Gly Asn Gly Asp
1               5

<210> SEQ ID NO 77
<211> LENGTH: 10
<212> TYPE: PRT
<213> ORGANISM: Artificial sequence
<220> FEATURE:
<223> OTHER INFORMATION: 44F7 HCDR3

<400> SEQUENCE: 77

Gly Gly Tyr Tyr Gly Asn Ser Leu Asp Tyr
1               5                   10

<210> SEQ ID NO 78
<211> LENGTH: 17
<212> TYPE: PRT
<213> ORGANISM: Artificial sequence
<220> FEATURE:
<223> OTHER INFORMATION: 44F7 LCDR1

<400> SEQUENCE: 78

Lys Ser Ser Gln Ser Leu Leu Asn Ser Gly Asn Gln Lys Asn Tyr Leu
1               5                   10                  15

Thr

```
<210> SEQ ID NO 79
<211> LENGTH: 7
<212> TYPE: PRT
<213> ORGANISM: Artificial sequence
<220> FEATURE:
<223> OTHER INFORMATION: 44F7 LCDR2

<400> SEQUENCE: 79

Trp Ala Ser Thr Arg Glu Ser
1               5

<210> SEQ ID NO 80
<211> LENGTH: 9
<212> TYPE: PRT
<213> ORGANISM: Artificial sequence
<220> FEATURE:
<223> OTHER INFORMATION: 44F7 LCDR3

<400> SEQUENCE: 80

Gln Asn Ala Tyr Tyr Tyr Pro Phe Thr
1               5

<210> SEQ ID NO 81
<211> LENGTH: 330
<212> TYPE: PRT
<213> ORGANISM: Artificial sequence
<220> FEATURE:
<223> OTHER INFORMATION: human IgG1 heavy chain constant region

<400> SEQUENCE: 81

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

-continued

```
Gln Pro Arg Glu Pro Gln Val Tyr Thr Leu Pro Pro Ser Arg Asp Glu
225             230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 82
<211> LENGTH: 107
<212> TYPE: PRT
<213> ORGANISM: Artificial sequence
<220> FEATURE:
<223> OTHER INFORMATION: human kappa light chain constant region

<400> SEQUENCE: 82

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 83
<211> LENGTH: 159
<212> TYPE: DNA
<213> ORGANISM: Artificial sequence
<220> FEATURE:
<223> OTHER INFORMATION: CLDN18.2-ECL1 DNA

<400> SEQUENCE: 83
gacatgtgga gcacccagga cctgtacgac aaccccgtga ccagcgtgtt ccagtacgag      60
ggcctgtgga ggagctgcgt gaggcagagc agcggcttca ccgagtgcag gccctacttc     120
accatcctgg gcctgccgc catgctgcag gccgtgagg                             159

<210> SEQ ID NO 84
<211> LENGTH: 1128
<212> TYPE: DNA
<213> ORGANISM: Artificial sequence
<220> FEATURE:
<223> OTHER INFORMATION: CLDN18.2-ECL1-C3d DNA

<400> SEQUENCE: 84
gaccagtgga gcacccaaga cttgtacaac aaccccgtaa cagctgtttt caactaccag      60
```

```
gggctgtggc gctcctgtgt ccgagagagc tctggcttca ccgagtgccg gggctacttc      120
accctgctgg ggctgccagc catgctgcag gcagtgcgag gcagcggcag cggcggcggc      180
ggcagcggcg gcggcggcag cggcagccac ctgatcgtga ccccgccgg ctgcggcgag       240 cagaacatga tcggcatgac ccccaccgtg atcgccgtgc actacctgga ccagaccgag      300
cagtgggaga agttcggcat cgagaagagg caggaggccc tggagctgat caagaagggc      360
tacacccagc agctggcctt caagcagccc agcagcgcct acgccgcctt caacaacagg      420
ccccccagca cctggctgac cgcctacgtg gtgaaggtgt tcagcctggc cgccaacctg      480
atcgccatcg acagccacgt gctgtgcggc gccgtgaagt ggctgatcct ggagaagcag      540
aagcccgacg gcgtgttcca ggaggacggc cccgtgatcc accaggagat gatcggcggc      600
ttcaggaacg ccaaggaggc cgacgtgagc ctgaccgcct tcgtgctgat cgccctgcag      660
gaggccaggg acatctgcga gggccaggtg aacagcctgc ccggcagcat caacaaggcc      720
ggcgagtaca tcgaggccag ctacatgaac ctgcagaggc cctacaccgt ggccatcgcc      780
ggctacgccc tggccctgat gaacaagctg gaggagccct acctgggcaa gttcctgaac      840
accgccaagg acaggaacag gtgggaggag cccgaccagc agctgtacaa cgtggaggcc      900
accagctacg ccctgctggc cctgctgctg ctgaaggact cgacagcgt gcccccgtg       960 gtgaggtggc tgaacgagca gaggtactac ggcggcggct acggcagcac ccaggccacc     1020
ttcatggtgt ccaggcct ggcccagtac cagaccgacg tgcccgacca caaggacctg      1080
aacatggacg tgagcttcca cctgcccagc aggggcagcg aggagttc                 1128
```

<210> SEQ ID NO 85
<211> LENGTH: 783
<212> TYPE: DNA
<213> ORGANISM: Artificial sequence
<220> FEATURE:
<223> OTHER INFORMATION: hCLDN18.2 DNA

<400> SEQUENCE: 85

```
atggccgtga ccgcctgcca gggcctgggc ttcgtggtga gcctgatcgg catcgccggc       60
atcatcgccg ccacctgcat ggaccagtgg agcacccagg acctgtacaa caaccccgtg      120
accgccgtgt tcaactacca gggcctgtgg aggagctgcg tgagggagag cagcggcttc      180
accgagtgca ggggctactt caccctgctg ggcctgcccg ccatgctgca ggccgtgagg      240
gccctgatga tcgtgggcat cgtgctgggc gccatcggcc tgctggtgag catcttcgcc      300
ctgaagtgca tcaggatcgg cagcatggag gacagcgcca aggccaacat gaccctgacc      360
agcggcatca tgttcatcgt gagcggcctg tgcgccatcg ccggcgtgag cgtgttcgcc      420
aacatgctgt tgaccaactt ctggatgagc accgccaaca tgtacaccgg catgggcggc      480
atggtgcaga ccgtgcagac caggtacacc ttcggcgccg ccctgttcgt gggctgggtg      540
gccggcggcc tgaccctgat cggcggcgtg atgatgtgca tcgcctgcag gggcctggcc      600
cccgaggaga ccaactacaa ggccgtgagc taccacgcca gcggccacag cgtggcctac      660
aagcccggcg gcttcaaggc cagcaccggc ttcggcagca acaccaagaa caagaagatc      720
tacgacggcg gcgccaggac cgaggacgag gtgcagagct accccagcaa gcacgactac      780
gtg                                                                     783
```

<210> SEQ ID NO 86
<211> LENGTH: 261
<212> TYPE: PRT

```
<213> ORGANISM: Artificial sequence
<220> FEATURE:
<223> OTHER INFORMATION: human CLDN18.2 amino acid sequence

<400> SEQUENCE: 86

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
                260

<210> SEQ ID NO 87
<211> LENGTH: 264
<212> TYPE: PRT
<213> ORGANISM: Artificial sequence
<220> FEATURE:
<223> OTHER INFORMATION: mouse CLDN18.2 amino acid sequence

<400> SEQUENCE: 87

Met Ser Val Thr Ala Cys Gln Gly Leu Gly Phe Val Val Ser Leu Ile
1               5                   10                  15

Gly Phe Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60
```

```
Gly Tyr Phe Thr Leu Leu Gly Leu Pro Ala Met Leu Gln Ala Val Arg
65                  70                  75                  80

Ala Leu Met Ile Val Gly Ile Val Leu Gly Val Ile Gly Ile Leu Val
                    85                  90                  95

Ser Ile Phe Ala Leu Lys Cys Ile Arg Ile Gly Ser Met Asp Asp Ser
                100                 105                 110

Ala Lys Ala Lys Met Thr Leu Thr Ser Gly Ile Leu Phe Ile Ile Ser
            115                 120                 125

Gly Ile Ser Ala Ile Ile Gly Val Ser Val Phe Ala Asn Met Leu Val
            130                 135                 140

Thr Asn Phe Trp Met Ser Thr Ala Asn Met Tyr Ser Gly Met Gly Gly
145                 150                 155                 160

Met Gly Gly Met Val Gln Thr Val Gln Thr Arg Tyr Thr Phe Gly Ala
                165                 170                 175

Ala Leu Phe Val Gly Trp Val Ala Gly Gly Leu Thr Leu Ile Gly Gly
                180                 185                 190

Val Met Met Cys Ile Ala Cys Arg Gly Leu Thr Pro Asp Asp Ser Asn
                195                 200                 205

Phe Lys Ala Val Ser Tyr His Ala Ser Gly Gln Asn Val Ala Tyr Arg
        210                 215                 220

Pro Gly Gly Phe Lys Ala Ser Thr Gly Phe Gly Ser Asn Thr Arg Asn
225                 230                 235                 240

Lys Lys Ile Tyr Asp Gly Gly Ala Arg Thr Glu Asp Asp Glu Gln Ser
                245                 250                 255

His Pro Thr Lys Tyr Asp Tyr Val
                260
```

<210> SEQ ID NO 88
<211> LENGTH: 261
<212> TYPE: PRT
<213> ORGANISM: Artificial sequence
<220> FEATURE:
<223> OTHER INFORMATION: human CLDN 18.1 amino acid sequence

<400> SEQUENCE: 88

```
Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
                20                  25                  30

Gln Asp Leu Tyr Asp Asn Pro Val Thr Ser Val Phe Gln Tyr Glu Gly
            35                  40                  45

Leu Trp Arg Ser Cys Val Arg Gln Ser Ser Gly Phe Thr Glu Cys Arg
        50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                    85                  90                  95

Ser Ile Phe Ala Leu Lys Cys Ile Arg Ile Gly Ser Met Glu Asp Ser
                100                 105                 110

Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
            130                 135                 140

Thr Asn Phe Trp Met Ser Thr Ala Asn Met Tyr Thr Gly Met Gly Gly
145                 150                 155                 160
```

-continued

```
Met Val Gln Thr Val Gln Thr Arg Tyr Thr Phe Gly Ala Ala Leu Phe
            165             170             175

Val Gly Trp Val Ala Gly Gly Leu Thr Leu Ile Gly Gly Val Met Met
            180             185             190

Cys Ile Ala Cys Arg Gly Leu Ala Pro Glu Glu Thr Asn Tyr Lys Ala
            195             200             205

Val Ser Tyr His Ala Ser Gly His Ser Val Ala Tyr Lys Pro Gly Gly
            210             215             220

Phe Lys Ala Ser Thr Gly Phe Gly Ser Asn Thr Lys Asn Lys Lys Ile
225             230             235             240

Tyr Asp Gly Gly Ala Arg Thr Glu Asp Glu Val Gln Ser Tyr Pro Ser
            245             250             255

Lys His Asp Tyr Val
            260

<210> SEQ ID NO 89
<211> LENGTH: 448
<212> TYPE: PRT
<213> ORGANISM: Artificial sequence
<220> FEATURE:
<223> OTHER INFORMATION: 175D10 heavy chain amino acid sequence

<400> SEQUENCE: 89

Gln Val Gln Leu Gln Gln Pro Gly Ala Glu Leu Val Arg Pro Gly Ala
1               5               10              15

Ser Val Lys Leu Ser Cys Lys Ala Ser Gly Tyr Thr Phe Thr Ser Tyr
            20              25              30

Trp Ile Asn Trp Val Lys Gln Arg Pro Gly Gln Gly Leu Glu Trp Ile
            35              40              45

Gly Asn Ile Tyr Pro Ser Asp Ser Tyr Thr Asn Tyr Asn Gln Lys Phe
            50              55              60

Lys Asp Lys Ala Thr Leu Thr Val Asp Lys Ser Ser Ser Thr Ala Tyr
65              70              75              80

Met Gln Leu Ser Ser Pro Thr Ser Glu Asp Ser Ala Val Tyr Tyr Cys
            85              90              95

Thr Arg Ser Trp Arg Gly Asn Ser Phe Asp Tyr Trp Gly Gln Gly Thr
            100             105             110

Thr Leu Thr Val Ser Ser Ala Ser Thr Lys Gly Pro Ser Val Phe Pro
            115             120             125

Leu Ala Pro Ser Ser Lys Ser Thr Ser Gly Gly Thr Ala Ala Leu Gly
            130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
            165             170             175

Ser Ser Gly Leu Tyr Ser Leu Ser Ser Val Val Thr Val Pro Ser Ser
            180             185             190

Ser Leu Gly Thr Gln Thr Tyr Ile Cys Asn Val Asn His Lys Pro Ser
            195             200             205

Asn Thr Lys Val Asp Lys Arg Val Glu Pro Lys Ser Cys Asp Lys Thr
            210             215             220

His Thr Cys Pro Pro Cys Pro Ala Pro Glu Leu Leu Gly Gly Pro Ser
225             230             235             240

Val Phe Leu Phe Pro Pro Lys Pro Lys Asp Thr Leu Met Ile Ser Arg
            245             250             255
```

```
Thr Pro Glu Val Thr Cys Val Val Val Asp Val Ser His Glu Asp Pro
            260             265             270

Glu Val Lys Phe Asn Trp Tyr Val Asp Gly Val Glu Val His Asn Ala
            275             280             285

Lys Thr Lys Pro Arg Glu Glu Gln Tyr Asn Ser Thr Tyr Arg Val Val
            290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
            325             330             335

Ile Ser Lys Ala Lys Gly Gln Pro Arg Glu Pro Gln Val Tyr Thr Leu
            340             345             350

Pro Pro Ser Arg Glu Glu Met Thr Lys Asn Gln Val Ser Leu Thr Cys
            355             360             365

Leu Val Lys Gly Phe Tyr Pro Ser Asp Ile Ala Val Glu Trp Glu Ser
            370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
            405             410             415

Arg Trp Gln Gln Gly Asn Val Phe Ser Cys Ser Val Met His Glu Ala
            420             425             430

Leu His Asn His Tyr Thr Gln Lys Ser Leu Ser Leu Ser Pro Gly Lys
            435             440             445
```

```
<210> SEQ ID NO 90
<211> LENGTH: 220
<212> TYPE: PRT
<213> ORGANISM: Artificial sequence
<220> FEATURE:
<223> OTHER INFORMATION: 175D10 light chain amino acid sequence

<400> SEQUENCE: 90
```

```
Asp Ile Val Met Thr Gln Ser Pro Ser Ser Leu Thr Val Thr Ala Gly
1               5               10              15

Glu Lys Val Thr Met Ser Cys Lys Ser Ser Gln Ser Leu Leu Asn Ser
            20              25              30

Gly Asn Gln Lys Asn Tyr Leu Thr Trp Tyr Gln Gln Lys Pro Gly Gln
            35              40              45

Pro Pro Lys Leu Leu Ile Tyr Trp Ala Ser Thr Arg Glu Ser Gly Val
            50              55              60

Pro Asp Arg Phe Thr Gly Ser Gly Ser Gly Thr Asp Phe Thr Leu Thr
65              70              75              80

Ile Ser Ser Val Gln Ala Glu Asp Leu Ala Val Tyr Tyr Cys Gln Asn
            85              90              95

Asp Tyr Ser Tyr Pro Phe Thr Phe Gly Ser Gly Thr Lys Leu Glu Ile
            100             105             110

Lys Arg Thr Val Ala Ala Pro Ser Val Phe Ile Phe Pro Pro Ser Asp
            115             120             125

Glu Gln Leu Lys Ser Gly Thr Ala Ser Val Val Cys Leu Leu Asn Asn
            130             135             140

Phe Tyr Pro Arg Glu Ala Lys Val Gln Trp Lys Val Asp Asn Ala Leu
145             150             155             160

Gln Ser Gly Asn Ser Gln Glu Ser Val Thr Glu Gln Asp Ser Lys Asp
            165             170             175
```

-continued

```
Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 91
<211> LENGTH: 118
<212> TYPE: PRT
<213> ORGANISM: Artificial sequence
<220> FEATURE:
<223> OTHER INFORMATION: 7004-09hu15 VH

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
        20                  25                  30

Tyr Met His Trp Val Arg Gln Ala Pro Gly Gln Gly Leu Glu Trp Met
        35                  40                  45

Gly Thr Ile Tyr Pro Gly Asn Gly Asp Thr Ser Tyr Asn Gln Lys Phe
        50                  55                  60

Gln Gly Arg Val Thr Met Thr Arg Asp Lys Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg Gly Gly Tyr Tyr Gly Asn Ser Leu Asp Tyr Trp Gly Gln Gly
            100                 105                 110

Thr Leu Val Thr Val Ser
        115

<210> SEQ ID NO 92
<211> LENGTH: 113
<212> TYPE: PRT
<213> ORGANISM: Artificial sequence
<220> FEATURE:
<223> OTHER INFORMATION: 7004-09hu15 VL

<400> SEQUENCE: 92

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
        20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Tyr Tyr Pro Phe Thr Phe Gly Gln Gly Thr Lys Leu Glu Ile
            100                 105                 110

Lys

<210> SEQ ID NO 93
<211> LENGTH: 7
```

-continued

```
<212> TYPE: PRT
<213> ORGANISM: Artificial sequence
<220> FEATURE:
<223> OTHER INFORMATION: 7004-09hu15 HCDR1

<400> SEQUENCE: 93

Gly Tyr Thr Phe Thr Ser Tyr
1               5

<210> SEQ ID NO 94
<211> LENGTH: 6
<212> TYPE: PRT
<213> ORGANISM: Artificial sequence
<220> FEATURE:
<223> OTHER INFORMATION: 7004-09hu15 HCDR2

<400> SEQUENCE: 94

Tyr Pro Gly Asn Gly Asp
1               5

<210> SEQ ID NO 95
<211> LENGTH: 10
<212> TYPE: PRT
<213> ORGANISM: Artificial sequence
<220> FEATURE:
<223> OTHER INFORMATION: 7004-09hu15 HCDR3

<400> SEQUENCE: 95

Gly Gly Tyr Tyr Gly Asn Ser Leu Asp Tyr
1               5                   10

<210> SEQ ID NO 96
<211> LENGTH: 17
<212> TYPE: PRT
<213> ORGANISM: Artificial sequence
<220> FEATURE:
<223> OTHER INFORMATION: 7004-09hu15 LCDR1

<400> SEQUENCE: 96

Lys Ser Ser Gln Ser Val Leu Asn Ser Gly Asn Gln Lys Asn Tyr Leu
1               5                   10                  15

Ala

<210> SEQ ID NO 97
<211> LENGTH: 7
<212> TYPE: PRT
<213> ORGANISM: Artificial sequence
<220> FEATURE:
<223> OTHER INFORMATION: 7004-09hu15 LCDR2

<400> SEQUENCE: 97

Trp Ala Ser Thr Arg Glu Ser
1               5

<210> SEQ ID NO 98
<211> LENGTH: 9
<212> TYPE: PRT
<213> ORGANISM: Artificial sequence
<220> FEATURE:
<223> OTHER INFORMATION: 7004-09hu15 LCDR3

<400> SEQUENCE: 98

Gln Asn Ala Tyr Tyr Tyr Pro Phe Thr
1               5

<210> SEQ ID NO 99
```

-continued

```
<211> LENGTH: 118
<212> TYPE: PRT
<213> ORGANISM: Artificial sequence
<220> FEATURE:
<223> OTHER INFORMATION: 7004-09hu09 VH

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Thr Ile Tyr Pro Gly Asn Gly Asp Thr Ser Tyr Asn Gln Lys Phe
    50                  55                  60

Gln Gly Arg Val Thr Met Thr Arg Asp Lys Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg Gly Gly Tyr Tyr Gly Asn Ser Leu Asp Tyr Trp Gly Gln Gly
            100                 105                 110

Thr Leu Val Thr Val Ser
        115

<210> SEQ ID NO 100
<211> LENGTH: 113
<212> TYPE: PRT
<213> ORGANISM: Artificial sequence
<220> FEATURE:
<223> OTHER INFORMATION: 7004-09hu09 VL

<400> SEQUENCE: 100

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Tyr Tyr Pro Phe Thr Phe Gly Gln Gly Thr Lys Leu Glu Ile
            100                 105                 110

Lys

<210> SEQ ID NO 101
<211> LENGTH: 118
<212> TYPE: PRT
<213> ORGANISM: Artificial sequence
<220> FEATURE:
<223> OTHER INFORMATION: 7004-09hu10 VH

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

-continued

```
                20              25              30

Tyr Met His Trp Val Arg Gln Ala Pro Gly Gln Gly Leu Glu Trp Met
            35              40              45

Gly Thr Ile Tyr Pro Gly Asn Gly Asp Thr Ser Tyr Asn Gln Lys Phe
    50              55              60

Gln Gly Arg Val Thr Met Thr Arg Asp Lys Ser Thr Ser Thr Val Tyr
65              70              75              80

Met Glu Leu Ser Ser Leu Arg Ser Glu Asp Thr Ala Val Tyr Phe Cys
            85              90              95

Ala Arg Gly Gly Tyr Tyr Gly Asn Ser Leu Asp Tyr Trp Gly Gln Gly
            100             105             110

Thr Leu Val Thr Val Ser
        115

<210> SEQ ID NO 102
<211> LENGTH: 113
<212> TYPE: PRT
<213> ORGANISM: Artificial sequence
<220> FEATURE:
<223> OTHER INFORMATION: 7004-09hu10 VL

<400> SEQUENCE: 102

Asp Ile Val Met Thr Gln Ser Pro Asp Ser Leu Ala Val Ser Leu Gly
1               5               10              15

Glu Arg Ala Thr Ile Asn Cys Lys Ser Ser Gln Ser Leu Leu Asn Ser
            20              25              30

Gly Asn Gln Lys Asn Tyr Leu Thr Trp Tyr Gln Gln Lys Pro Gly Gln
        35              40              45

Pro Pro Lys Leu Leu Ile Tyr Trp Ala Ser Thr Arg Glu Ser Gly Val
    50              55              60

Pro Asp Arg Phe Ser Gly Ser Gly Ser Gly Thr Asp Phe Thr Leu Thr
65              70              75              80

Ile Ser Ser Leu Gln Ala Glu Asp Val Ala Val Tyr Tyr Cys Gln Asn
            85              90              95

Ala Tyr Tyr Tyr Pro Phe Thr Phe Gly Gln Gly Thr Lys Leu Glu Ile
            100             105             110

Lys

<210> SEQ ID NO 103
<211> LENGTH: 339
<212> TYPE: DNA
<213> ORGANISM: Artificial sequence
<220> FEATURE:
<223> OTHER INFORMATION: 1D10 VH encoding nucleic acid sequence

<400> SEQUENCE: 103
caggtccaac tgcagcagcc tggggctgag ctggtaaagc ctggggcttc agtgaagttg      60
tcctgcaagg cttctggcta cactttcacc agctactgga tgcactgggt gaagcagagg     120
cctggacaag gccttgagtg gattggaatg atttatccta atagtggtag cattaactac     180
aatgagaagt tcaagaacaa ggccacactg actgtagaca atcctccag cacagcctac      240 atgcaactca gcagcctgac atctgaggac tctgcggtct atttctgttc tgtctacttt     300
gactactggg gccaaggcac cactctcaca gtctcctca                           339

<210> SEQ ID NO 104
<211> LENGTH: 321
<212> TYPE: DNA
```

```
<213> ORGANISM: Artificial sequence
<220> FEATURE:
<223> OTHER INFORMATION: 1D10 VL encoding nucleic acid sequence

<400> SEQUENCE: 104
gacatccagg ggacacagtc tccatcctcc ttatctgcct ctctgggaga aagagtcagt      60
ctcacttgtc gggcaagtca ggacattggt agtagcttaa actggcttca gcaggaacca     120
gatggaacta ttaaacgcct gatctacgcc acatccagtt tagattctgg tgtccccaaa     180
aggttcagtg tcagtaggtc tgggtcagat tattctctca ccatcagcag ccttgagtct     240
gaagattttg tagactatta ctgtctacaa tatgctagtt ctcctccgac gttcggtgga     300
ggcaccaaac tggaaatcaa a                                               321

<210> SEQ ID NO 105
<211> LENGTH: 354
<212> TYPE: DNA
<213> ORGANISM: Artificial sequence
<220> FEATURE:
<223> OTHER INFORMATION: 2F12 VH encoding nucleic acid sequence

<400> SEQUENCE: 105
gaggtgcagc tggtggagtc tggggggaggc ttagtgaagc ctggagggtc cctgaaactc      60
tcctgtgctg cctctggatt cactttcagt gactatggga tccactgggt tcgtcaggct     120
ccagagaagg ggctggagtg ggttgcatac attagtagtg gcagtagtac catctactat     180
gcagacacag tgaagggccg attcaccatc tccagagaca atgccaagaa caccctgttc     240
ctgcaaatga ccagtctgag gtctgaggac acggccatat attactgtgc aaagtgggac     300
cggggtaact gctttgacta ctggggccaa ggcaccactc tcacagtctc ctca           354

<210> SEQ ID NO 106
<211> LENGTH: 339
<212> TYPE: DNA
<213> ORGANISM: Artificial sequence
<220> FEATURE:
<223> OTHER INFORMATION: 2F12 VL encoding nucleic acid sequence

<400> SEQUENCE: 106
gacattgtgt tgacccagtc tccatcctcc ctgactgtga cagcaggaga gaaggtcact      60
atgagctgca gtccagtca gagtctgtta aacagtggaa tcaaaagaa atacttgacc      120 tggtatcagc agaaagtagg gcagcctcct aaactgttga tttactgggc atccattagg     180
gaatgtgggg tccctgatcg cttcacaggc agtggatctg aaacagattt cattctcacc     240
atcagcagtg tgcaggctga agacctggca gtttattact gtcagaatgc ttatagttat     300
ccgctcacgt tcggtgctgg gaccaagctg gagctgaaa                            339

<210> SEQ ID NO 107
<211> LENGTH: 354
<212> TYPE: DNA
<213> ORGANISM: Artificial sequence
<220> FEATURE:
<223> OTHER INFORMATION: 3F2 VH encoding nucleic acid sequence

<400> SEQUENCE: 107
gaggtgatgc tggtggagtc tggggggaggc ttagtgaagc ctggagggtc cctgaaactc      60
tcctgtgcag cctctggatt cactttcagt acctatgcca tgtcttgggt tcgccagact     120
ccggaaaaga ggctggagtg gatcgcaacc attaatgatg gtggtactta cacctactat     180
ccagacaatg taaagggccg attcaccatc tccagagaca atgccaagaa caacctgtac     240
```
ctacacatga gccatctgaa gtctgacgac acagccatcc attactgtac aagactagcg        300 aggggggaatt ctatggacta ctggggtcaa ggaacctcag tcaccgtctc ctca            354

<210> SEQ ID NO 108
<211> LENGTH: 354
<212> TYPE: DNA
<213> ORGANISM: Artificial sequence
<220> FEATURE:
<223> OTHER INFORMATION: 3F2 VL encoding nucleic acid sequence

<400> SEQUENCE: 108
gaggtgatgc tggtggagtc tggggggaggc ttagtgaagc ctggagggtc cctgaaactc        60
tcctgtgcag cctctggatt cactttcagt acctatgcca tgtcttgggt tcgccagact        120
ccggaaaaga ggctggagtg gatcgcaacc attaatgatg gtggtactta cacctactat        180
ccagacaatg taaagggccg attcaccatc tccagagaca atgccaagaa caacctgtac        240
ctacacatga gccatctgaa gtctgacgac acagccatcc attactgtac aagactagcg        300 aggggggaatt ctatggacta ctggggtcaa ggaacctcag tcaccgtctc ctca            354

<210> SEQ ID NO 109
<211> LENGTH: 339
<212> TYPE: DNA
<213> ORGANISM: Artificial sequence
<220> FEATURE:
<223> OTHER INFORMATION: 5F9 VH encoding nucleic acid sequence

<400> SEQUENCE: 109
caggtccaac tgcagcagtc tggggctgag ctggtaaagc ctggggcttc agtgaagttg        60
tcctgcaagg cttctggcta cactttcacc agctactgga tgcactgggt gaagcagagg        120
cctggacaag gccttgagtg gattggaatg attcatccta atagtgttag tactaactac        180
aatgagaagt tcaagagcaa ggccacactg actgtagaca atcctccag cacagcctac        240 atgcaactca gcagcctgac atctgaggac tctgcggtct attactgtgc tgtctacttt        300
gactactggg gccaaggcac cactctcaca gtctcctca                              339

<210> SEQ ID NO 110
<211> LENGTH: 321
<212> TYPE: DNA
<213> ORGANISM: Artificial sequence
<220> FEATURE:
<223> OTHER INFORMATION: 5F9 VL encoding nucleic acid sequence

<400> SEQUENCE: 110
gacatccagg tgacacagtc tccatcctcc ttatctgcct ctctgggaga aagagtcagt        60
ctcacttgtc gggcaagtca ggacattggt agtagcttaa actggcttca gcaggaacca        120
gatggaacta ttaaacgcct gatctacgcc tcatccagtt aaattctgg tgtccccaaa        180 aggttcagtg tcagtaggtc tgggtcagat tattctctca ccatcagcag ccttgagtct        240
gaagattttg tagactatta ctgtctacaa tatgctactt ctcctccgac gttcggtgga        300
ggcaccaagc tggaaatcaa a                                                  321

<210> SEQ ID NO 111
<211> LENGTH: 354
<212> TYPE: DNA
<213> ORGANISM: Artificial sequence
<220> FEATURE:
<223> OTHER INFORMATION: 9F3 VH encoding nucleic acid sequence

<400> SEQUENCE: 111
gaggttcggc tgcaacagtc tggacctgag ctggtgaagc ctgggggcttc agtgaagata      60 ccctgcaagg cttctggata caaattcact gactacaaca tggactgggt gaagcagagc     120
catggaaaga gccttgagtg gattggagaa attaatccta caatggtgg tactatctac      180 aaccagaagt tcaagggcaa ggccacattg actgtagaca agtcctccag cacagcctac     240
atggagctcc gcagcctgac atctgaggac actgcagtct attactgtgc aagaatttac     300
tatggtaact cctttgctta ctgggggccaa gggactctgg tcactgtctc ttca          354

<210> SEQ ID NO 112
<211> LENGTH: 339
<212> TYPE: DNA
<213> ORGANISM: Artificial sequence
<220> FEATURE:
<223> OTHER INFORMATION: 9F3 VL encoding nucleic acid sequence

<400> SEQUENCE: 112
gacattgtga tgacacagtc tccatcctcc ctgactgtga cagcaggaga gaaggtcact      60
atgagctgca agtccagtca gagtctgtta aacagtggaa atctaaagaa ctacttgacc     120
tggtaccagc agaaaccagg gcagcctcct aaacttttga tctactgggc atccactagg     180
gaatctgggg tccctgatcg cttcacaggc agtggatctg gaacagattt cactctcacc     240
atcagcagtg tgcaggctga agacctggca gtttattact gtcagaatga ttattttttat    300 ccgctcacgt tcggtgctgg gaccaagctg gaaatcaaa                            339

<210> SEQ ID NO 113
<211> LENGTH: 354
<212> TYPE: DNA
<213> ORGANISM: Artificial sequence
<220> FEATURE:
<223> OTHER INFORMATION: 10B11 VH encoding nucleic acid sequence

<400> SEQUENCE: 113
caggtgcaaa tgaaggagtc tggggctgag ctggtgaagc ctgggggcctc agtgaagatt      60 tcctgcaaag cttctggcta cgcattcagt acctactgga tggactgggt gaagcagagg     120
cctggaaagg gtcttgagtg gattggacag atttatcctg aaatggtga tactaactac      180 aacggaaagt tcaagggcaa ggccacactg actgcagaca atcctccag cacagccgac      240 atgcagctca gcagcctgac ctctgaggac tctgcggtct atttctgtgc aagattgggg     300
tatggtaact cgtttactta ctggggccaa gggactctgg tcactgtctc tgca           354

<210> SEQ ID NO 114
<211> LENGTH: 339
<212> TYPE: DNA
<213> ORGANISM: Artificial sequence
<220> FEATURE:
<223> OTHER INFORMATION: 10B11 VL encoding nucleic acid sequence

<400> SEQUENCE: 114
gacatccagg tgacacagtc tccatcctcc ctgactgtga cagcaggaga gaaggtcact      60
atgagctgca agtccagtca gagtctgtta aacagtggaa atcaaaagaa ctacttgacc     120
tggtaccagc agaaaccagg gcagcctcct aaactgttga tctactgggc atccactagg     180
gaatctgggg tccctgatcg cttcacaggc agtggatttg gaacagattt cactctcacc     240
atcagcagtg tgcaggctga agacctggca gtttattact gtcagaatgc ttattttttat    300 ccattcacgt tcggctcggg gacaaagctg gaaatcaaa                            339

<210> SEQ ID NO 115
<211> LENGTH: 354
<212> TYPE: DNA
<213> ORGANISM: Artificial sequence
<220> FEATURE:
<223> OTHER INFORMATION: 27B5 VH encoding nucleic acid sequence

<400> SEQUENCE: 115

```
caggtccaac tgcagcagcc tgggaccgag ctggtgaagc ctggggcttc agtgaagctg        60
tcctgcaagg cttctggcta caccttcacc agctactgga tgcactgggt gaagcagagg       120
cctggacaag gccttgagtg gattggaaat attcatccta gcaatggtgg tagtaaccac       180
aatgagaagt tcaagagcaa ggccacactg actgtagaca atcctccag cacagcctac        240 atgcagctca gcagcctgac atctgaggac tctgcggtct attattgtgc gcctatctac       300
tatggtaact cgcttgctta ttggggccac gggactctgg tcactgtctc tgca             354
```

<210> SEQ ID NO 116
<211> LENGTH: 339
<212> TYPE: DNA
<213> ORGANISM: Artificial sequence
<220> FEATURE:
<223> OTHER INFORMATION: 27B5 VL encoding nucleic acid sequence

<400> SEQUENCE: 116

```
gatgttgtga tgacccagtc tccatcctcc ctgactgtga cagcaggaga gaaggtcact        60
atgagctgca gtccagtca gagtctgtta aacagtggaa tcaaaagaa ctacttgacc         120 tggtaccagc agaaaccagg gcagcctcct aaactattgc tctactgggc atccactagg       180
gaatctgggg tccctgatcg cttcacaggc agtggatctg gaacagattt cactctcacc       240
atcagcagtg tgcaggctga agacctggca gtttattact gtcagaatag ttattttttat      300 ccattcacgt tcggctcggg gacaaagctg gaaatcaaa                               339
```

<210> SEQ ID NO 117
<211> LENGTH: 354
<212> TYPE: DNA
<213> ORGANISM: Artificial sequence
<220> FEATURE:
<223> OTHER INFORMATION: 37B1 VH encoding nucleic acid sequence

<400> SEQUENCE: 117

```
gaggttcggc tgcaacagtc tggacctgag ctggtgaagc ctggggcttc agtgaagatg        60
tcctgcaagg cttctggata ctcattcact gactacaaca tgcactgggt gaagcagagc       120
catggaaaga gccctgagtg ggttggatat attaacccta caagggtgg tactggctac        180 aaccagaagt tcaagggcaa ggccacattg actgtaaaca gtcctccag cacagccaac        240 atggagctcc gcagcctgac atcggaggat tccgcagtct attactgtgc acggatatgg       300
tatggtaatt cgtttgctta ctggggccaa gggactctgg tcactgtctc agca             354
```

<210> SEQ ID NO 118
<211> LENGTH: 339
<212> TYPE: DNA
<213> ORGANISM: Artificial sequence
<220> FEATURE:
<223> OTHER INFORMATION: 37B1 VL encoding nucleic acid sequence

<400> SEQUENCE: 118

```
gatgttgtga tgacacagtc tccatcctcc ctgactgtga cagcaggaga gaaggtcact        60
```

-continued

```
atgagctgca agtccagtca gagtctgtta aacagtggaa atcaaaagaa ctacttgacc     120
tggtaccagc agaaaccagg gcagcctcct aaactgttga tctactgggc atccactagg     180
gaatctgggg tccctgatcg cttcacaggc agtggatctg gaacagattt cactctcacc     240
atcagcagtg tgcaggctga agacctggca gtttatttct gtcagaatga ttattttat      300 ccattcacgt tcggctcggg gacaaagttg gaaataaaa                            339

<210> SEQ ID NO 119
<211> LENGTH: 357
<212> TYPE: DNA
<213> ORGANISM: Artificial sequence
<220> FEATURE:
<223> OTHER INFORMATION: 44A8 VH encoding nucleic acid sequence

<400> SEQUENCE: 119
gaggttcggc tgcaacagtc tggacctgag ctggtgaagc ctggggcttc agtgaagatg      60
tcctgcaagg cttctggata cacattcact gactacaaca tgcactgggt gaaacagagc     120
catggaaaga gccttgagtg gattggatat attaacccta gaaatggtgg tattagatac     180
aaccagaagt tcacgggcaa ggccacattg actgtaaaca gtcctccag cacagcctac      240 atggagctcc gcagcctgac atcggaggat tctgcagtct attactgtgc aagaggggggt     300 tactacggta atactttgga caactggggt caaggaacct cagtcaccgt ctcctca        357

<210> SEQ ID NO 120
<211> LENGTH: 339
<212> TYPE: DNA
<213> ORGANISM: Artificial sequence
<220> FEATURE:
<223> OTHER INFORMATION: 44A8 VL encoding nucleic acid sequence

<400> SEQUENCE: 120
gacattgtga tgacacagtc tccatcctcc ctgactctga cagcaggaga gaaggtcact      60
atgagctgca agtccagtca gagtctgtta aacagtggaa atcaaaagaa ctacttgacc     120
tggtaccagc agaaaccagg gcagcctcct aaactgttga tctactgggc atccactagt     180
gaatctgggg tccctgatcg cttcacaggc agtggatctg gaacagattt cactctcacc     240
atcagcagtg tgcaggctga agacctggca atttattact gtcagaatgc ttattttat      300 ccgtggacgt tcggtggagg caccaaactg gagatcaaa                            339

<210> SEQ ID NO 121
<211> LENGTH: 357
<212> TYPE: DNA
<213> ORGANISM: Artificial sequence
<220> FEATURE:
<223> OTHER INFORMATION: 44F7 VH encoding nucleic acid sequence

<400> SEQUENCE: 121
caggtccaac tgcagcagtc tggggctgag ctggtgaggc ctggggcctc agtgaagatg      60
tcctgcaagg cttctggcta cacatttacc agttacaata tgcactgggt aaagcaggca     120
cctagacagg gcctggaatg gattggaact atttatccag gaaatggtga tacttcctac     180
aatcagaagt tcaagggcaa ggccacactg actgtagaca atcctccag cacagcctac      240 atgcagctca gcagcctgac atctgaggac tctgcggtct atttctgtgc aagagggggc     300
tactatggta actctcttga ctactggggc caaggcacca ctctcacagt ctcctca        357

<210> SEQ ID NO 122
<211> LENGTH: 339
```

-continued

```
<212> TYPE: DNA
<213> ORGANISM: Artificial sequence
<220> FEATURE:
<223> OTHER INFORMATION: 44F7 VL encoding nucleic acid sequence

<400> SEQUENCE: 122
gacatccaga tgacacagtc tccatcctcc ctgactgtga cagcaggaga gaaggtcact      60
atgagctgca agtccagtca gagtctgtta aacagtggaa atcaaaagaa ctacttgacc     120
tggtaccagc agaaaccagg acagcctcct aaactgttga tctactgggc atccactagg     180
gaatctgggg tccctgatcg cttcacaggc agtggatctg aacagattt cactctcacc      240 atcagcagtg tgcaggctga gacctggca gtttattact gtcagaatgc ttattattat      300
ccattcacgt tcggctcggg gacaaagctg gagatcaaa                           339

<210> SEQ ID NO 123
<211> LENGTH: 354
<212> TYPE: DNA
<213> ORGANISM: Artificial sequence
<220> FEATURE:
<223> OTHER INFORMATION: 7004-09hu15 VH encoding nucleic acid sequence

<400> SEQUENCE: 123
caggtgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag ggcttgagtg gatgggaact atctatcctg gtaatggtga tacaagctac     180
aaccagaagt tccagggcag agtcaccatg accagggaca gtccacgag cacagtctac      240 atggagctga gcagcctgag atctgaggac acggccgtgt atttctgtgc gagaggcggg     300
tattatggga acagtcttga ctactgggggc cagggaaccc tggtcaccgt ctcc          354

<210> SEQ ID NO 124
<211> LENGTH: 339
<212> TYPE: DNA
<213> ORGANISM: Artificial sequence
<220> FEATURE:
<223> OTHER INFORMATION: 7004-09hu15 VL encoding nucleic acid sequence

<400> SEQUENCE: 124
gacatcgtga tgacccagtc tccagactcc ctggctgtgt ctctgggcga gagggccacc      60
atcaactgca agtccagcca gagtgtttta aacagcggca accagaagaa ctacttagct     120
tggtaccagc agaaaccagg acagcctcct aagttgctca tttactgggc gtctacccgg     180
gaatccgggg tccctgaccg attcagtggc agcgggtctg ggacagatt cactctcacc      240 attagcagcc tgcaggctga agatgtggca gtttattact gtcagaatgc atattactac      300 ccttcactt ttggccaggg gaccaagctg gagatcaaa                            339

<210> SEQ ID NO 125
<211> LENGTH: 354
<212> TYPE: DNA
<213> ORGANISM: Artificial sequence
<220> FEATURE:
<223> OTHER INFORMATION: The nucleic acid sequence encoding VH of
        7004-09hu09

<400> SEQUENCE: 125
caggtgcagc tggtgcagtc tggggctgag gtgaagaagc ctggggcctc agtgaaggtt      60
tcctgcaagg catctggata caccttcacc agctacaaca tgcactgggt gcgacaggcc     120
cctggacaag ggcttgagtg gatgggaact atctatcctg gtaatggtga tacaagctac     180
```

-continued

```
aaccagaagt tccagggcag agtcaccatg accagggaca agtccacgag cacagtctac      240
atggagctga gcagcctgag atctgaggac acggccgtgt atttctgtgc gagaggcggg      300
tattatggga acagtcttga ctactggggc cagggaaccc tggtcaccgt ctcc            354
```

<210> SEQ ID NO 126
<211> LENGTH: 339
<212> TYPE: DNA
<213> ORGANISM: Artificial sequence
<220> FEATURE:
<223> OTHER INFORMATION: The nucleic acid sequence encoding VL of
      7004-09hu09

<400> SEQUENCE: 126

```
gacatcgtga tgacccagtc tccagactcc ctggctgtgt ctctgggcga gagggccacc       60
atcaactgca agtccagcca gagtctttta aacagtggca accagaagaa ctatttaact      120
tggtaccagc agaaaccagg acagcctcct aagttgctca tttactgggc atctacccgg      180
gaatccgggg tccctgaccg attcagtggc agcgggtcag gaacagactt cactctcacc      240
atcagcagcc tgcaggctga agatgtggca gtttattact gtcagaatgc atattactac      300
ccgttcactt ttggccaggg gaccaagctg gagatcaaa                             339
```

<210> SEQ ID NO 127
<211> LENGTH: 354
<212> TYPE: DNA
<213> ORGANISM: Artificial sequence
<220> FEATURE:
<223> OTHER INFORMATION: The nucleic acid sequence encoding VH of
      7004-09hu10

<400> SEQUENCE: 127

```
caggtgcagc tggtgcagtc tggggctgag gtgaagaagc ctggggcctc agtgaaggtt       60
tcctgcaagg catctggata caccttcacc agctactata tgcactgggt gcgacaggcc      120
cctggacaag ggcttgagtg gatgggaact atctatcctg gtaatggtga tacaagctac      180
aaccagaagt tccagggcag agtcaccatg accagggaca agtccacgag cacagtctac      240
atggagctga gcagcctgag atctgaggac acggccgtgt atttctgtgc gagaggcggg      300
tattatggga acagtcttga ctactggggc cagggaaccc tggtcaccgt ctcc            354
```

<210> SEQ ID NO 128
<211> LENGTH: 339
<212> TYPE: DNA
<213> ORGANISM: Artificial sequence
<220> FEATURE:
<223> OTHER INFORMATION: The nucleic acid sequence encoding VL of
      7004-09hu10

<400> SEQUENCE: 128

```
gacatcgtga tgacccagtc tccagactcc ctggccgtgt ctctgggcga gagggccacc       60
atcaactgca agtccagcca gagtctttta aacagcggca accagaagaa ctacttaact      120
tggtaccagc agaaaccagg acagcctcct aagttgctca tttactgggc gtctacccgg      180
gaatccgggg tccctgaccg attcagtggc tccgggtctg ggacagattt cactctcacc      240
atcagcagcc tgcaggctga agatgtggca gtttattact gtcaaaatgc atactactac      300
ccgttcactt ttggccaggg gaccaagctg gagatcaaa                             339
```